(12) United States Patent
Leo

(10) Patent No.: US 10,058,080 B2
(45) Date of Patent: *Aug. 28, 2018

(54) INSECT PRODUCTION SYSTEMS AND METHODS

(71) Applicant: Daniel Michael Leo, Baltimore, MD (US)

(72) Inventor: Daniel Michael Leo, Baltimore, MD (US)

(*) Notice: Subject to any disclaimer, the term of this patent is extended or adjusted under 35 U.S.C. 154(b) by 178 days.

This patent is subject to a terminal disclaimer.

(21) Appl. No.: 15/242,582

(22) Filed: Aug. 21, 2016

(65) Prior Publication Data

US 2018/0049416 A1 Feb. 22, 2018

(51) Int. Cl.
| | |
|---|---|
| A01K 67/033 | (2006.01) |
| A21D 2/34 | (2006.01) |
| A23K 20/20 | (2016.01) |
| A23K 20/174 | (2016.01) |
| A23K 20/163 | (2016.01) |

(52) U.S. Cl.
CPC .............. *A01K 67/033* (2013.01); *A21D 2/34* (2013.01); *A23K 20/163* (2016.05); *A23K 20/174* (2016.05); *A23K 20/20* (2016.05)

(58) Field of Classification Search
USPC .......................................... 426/656; 119/6.5
See application file for complete search history.

(56) References Cited

U.S. PATENT DOCUMENTS

| | | | |
|---|---|---|---|
| 2,515,684 A | 7/1950 | Ambrette | |
| 2,539,633 A | 1/1951 | Morrill | |
| 2,732,627 A | 1/1956 | Farva | |
| 2,804,697 A | 9/1957 | Coffaro | |
| 2,901,090 A | 8/1959 | Marchetti | |
| 3,339,530 A | 9/1967 | Gillette | |
| 3,397,991 A | 8/1968 | Johnson | |
| 3,750,625 A | 8/1973 | Edwards | |

(Continued)

FOREIGN PATENT DOCUMENTS

| | | |
|---|---|---|
| CN | 101406295 A  *  4/2009 | |
| WO | WO2014046529 A2   3/2014 | |

(Continued)

OTHER PUBLICATIONS

Banas et al. Reasonable guidance values for THC (Tetrahydrocannabinol) in food products. EIHA Jan. 2017 (Year: 2017).*

(Continued)

*Primary Examiner* — Nina Bhat

(57) ABSTRACT

Variable-scale, modular, easily manufacturable, energy efficient, reliable, and computer operated Insect Production Superstructure Systems (IPSS) may be used to produce insects for human and animal consumption, and for the extraction and use of lipids for applications involving medicine, nanotechnology, consumer products, and chemical production with minimal water, feedstock, and environmental impact. An IPSS may comprise modules including feedstock mixing, feedstock splitting, insect feeding, insect breeding, insect collection, insect grinding, pathogen removal, multifunctional flour mixing, and lipid extraction. An IPSS may be configured to be constructed out of a plurality of containerized modules.

26 Claims, 47 Drawing Sheets

(56) References Cited

U.S. PATENT DOCUMENTS

| | | | |
|---|---|---|---|
| 3,805,946 | A | 4/1974 | Yateman et al. |
| 4,411,220 | A | 10/1983 | Voegele et al. |
| 4,765,274 | A | 8/1988 | Pizzol et al. |
| 5,186,310 | A | 2/1993 | Winchester |
| 5,369,908 | A | 12/1994 | Morales |
| 5,970,918 | A | 10/1999 | Bargy |
| 5,996,769 | A | 12/1999 | Winchip |
| 6,003,659 | A | 12/1999 | Uranaka et al. |
| 6,235,528 | B1 | 5/2001 | Cohen |
| 6,293,223 | B1 | 9/2001 | Blossey et al. |
| 6,474,259 | B1 | 11/2002 | Gaugler |
| 6,506,597 | B2 | 1/2003 | Cohen |
| 6,517,856 | B1 | 2/2003 | Roe et al. |
| 6,532,891 | B2 | 3/2003 | Gaugler et al. |
| 6,561,125 | B1 | 5/2003 | Lohsomboon |
| 6,877,269 | B2 | 4/2005 | Schultz |
| 6,938,574 | B2 | 9/2005 | Zhang |
| 7,174,847 | B1 | 2/2007 | Hulteen |
| 7,444,956 | B2 | 11/2008 | Vadis |
| 7,444,957 | B2 | 11/2008 | Vadis |
| 7,464,664 | B2 | 12/2008 | Vadis |
| 7,500,446 | B2 | 3/2009 | Vadis |
| 7,523,716 | B2 | 4/2009 | Vadis |
| 7,549,391 | B2 | 6/2009 | Vadis |
| 7,878,146 | B2 | 2/2011 | Vadis |
| 8,683,944 | B2 | 4/2014 | Jo et al. |
| 8,720,804 | B1 | 5/2014 | Pearson |
| 8,816,518 | B2 | 8/2014 | Campion et al. |
| 9,210,916 | B2 | 12/2015 | Finke |
| 9,254,960 | B2 | 2/2016 | Pribyl |
| 9,480,278 | B2 | 11/2016 | Finke |
| 9,855,562 | B2* | 1/2018 | Bates ............... B02C 23/10 |
| 9,937,147 | B2* | 4/2018 | DeGeeter ............. A61K 31/352 |
| 2004/0151818 | A1* | 8/2004 | Cockerum ............. A23L 7/183 |
| | | | 426/559 |
| 2006/0266292 | A1 | 11/2006 | Duckworth |
| 2007/0116846 | A1 | 5/2007 | Singh-Meneghini |
| 2007/0148202 | A1 | 6/2007 | Yufera et al. |
| 2007/0245587 | A1 | 10/2007 | Cottam |
| 2008/0075818 | A1* | 3/2008 | Papadoyianis ......... A23K 50/80 |
| | | | 426/416 |
| 2009/0285937 | A1* | 11/2009 | Vadis ..................... A23K 40/20 |
| | | | 426/62 |
| 2011/0139075 | A1 | 6/2011 | Shapiro Ilan et al. |
| 2012/0148712 | A1* | 6/2012 | Guilfoyle ............. A23L 1/0035 |
| | | | 426/231 |
| 2013/0319334 | A1 | 12/2013 | Newton et al. |
| 2013/0330444 | A1* | 12/2013 | Barbosa Senra Lopes ................. A23G 1/50 |
| | | | 426/104 |
| 2014/0026063 | A1 | 1/2014 | Courtright |
| 2014/0093611 | A1 | 4/2014 | Karcher et al. |
| 2015/0132433 | A1 | 5/2015 | Dossey |
| 2015/0223508 | A1* | 8/2015 | Arsiwalla ............... A23L 33/00 |
| | | | 426/7 |
| 2015/0296760 | A1 | 10/2015 | Perednia |
| 2016/0037808 | A1* | 2/2016 | Miller ................... A23L 1/1041 |
| | | | 426/622 |
| 2016/0066552 | A1 | 3/2016 | Arsiwalla et al. |
| 2017/0196923 | A1* | 7/2017 | Moore ................. A61K 36/185 |

FOREIGN PATENT DOCUMENTS

| | | |
|---|---|---|
| WO | WO2015023178 A1 | 2/2015 |
| WO | WO2016062979 A1 | 4/2016 |

OTHER PUBLICATIONS

Aman et al. "Grasshoppers as a food source? A Review", Universite de liege, Jan. 12, 2016 (Year: 2016).*

Nuts .com Cricket Flour, compositional ingredients (Year: 1999).*

"Eating Bugs" by Aletheia Price (Year: 2001).*

* cited by examiner

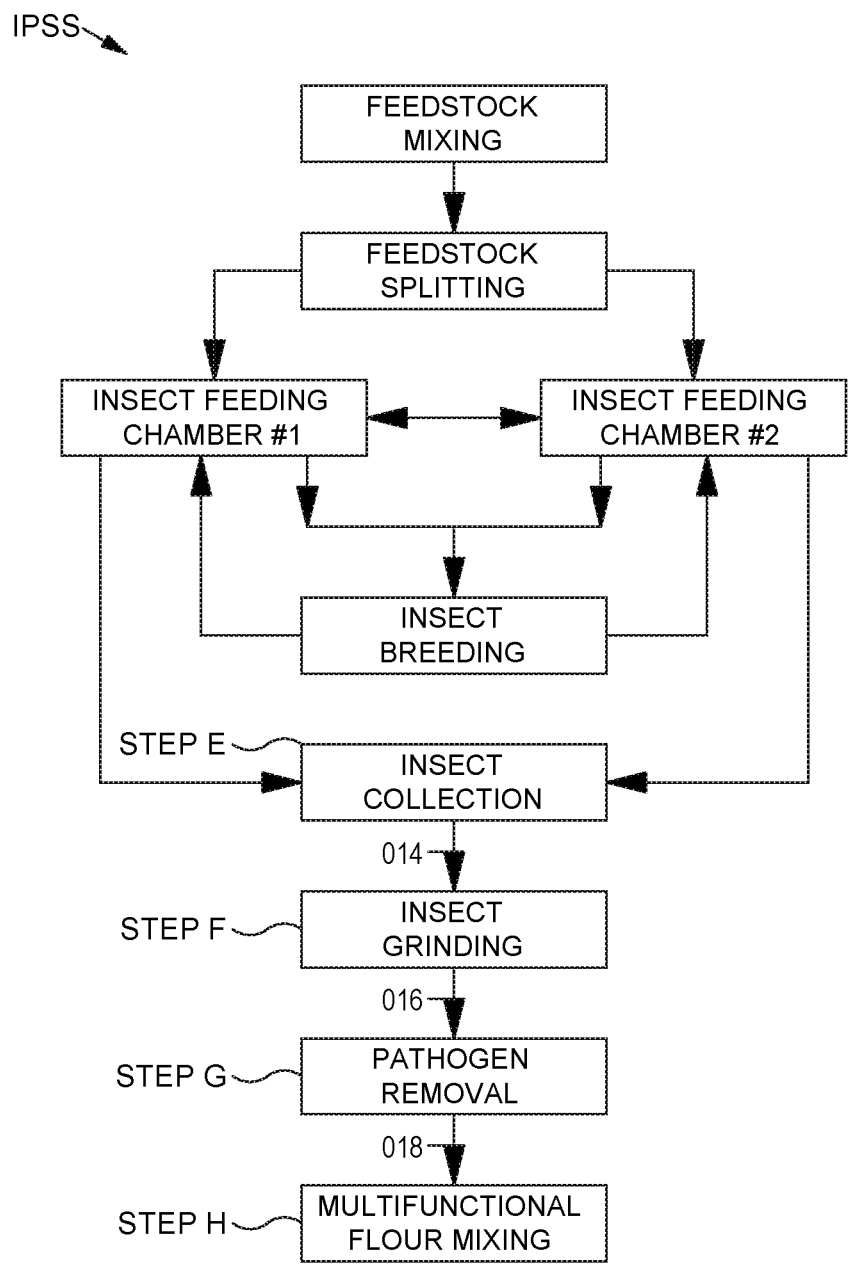

INSECT GRINDING MODULE

LIPID EXTRACTION MODULE

PATHOGEN REMOVAL MODULE

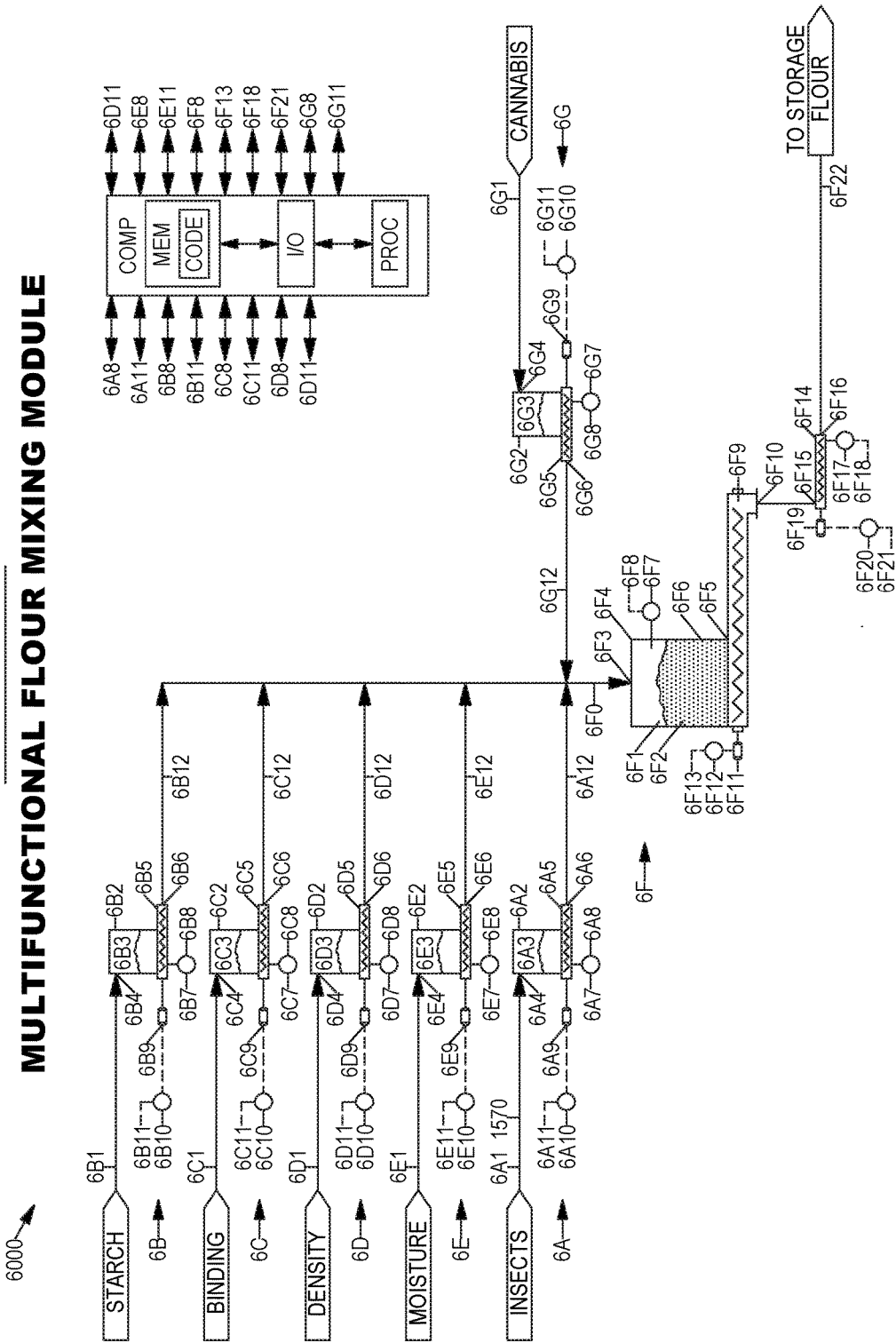

MULTIFUNCTIONAL FLOUR MIXING MODULE

MODULAR INSECT PRODUCTION SUPERSTRUCTURE SYSTEM (IPSS)

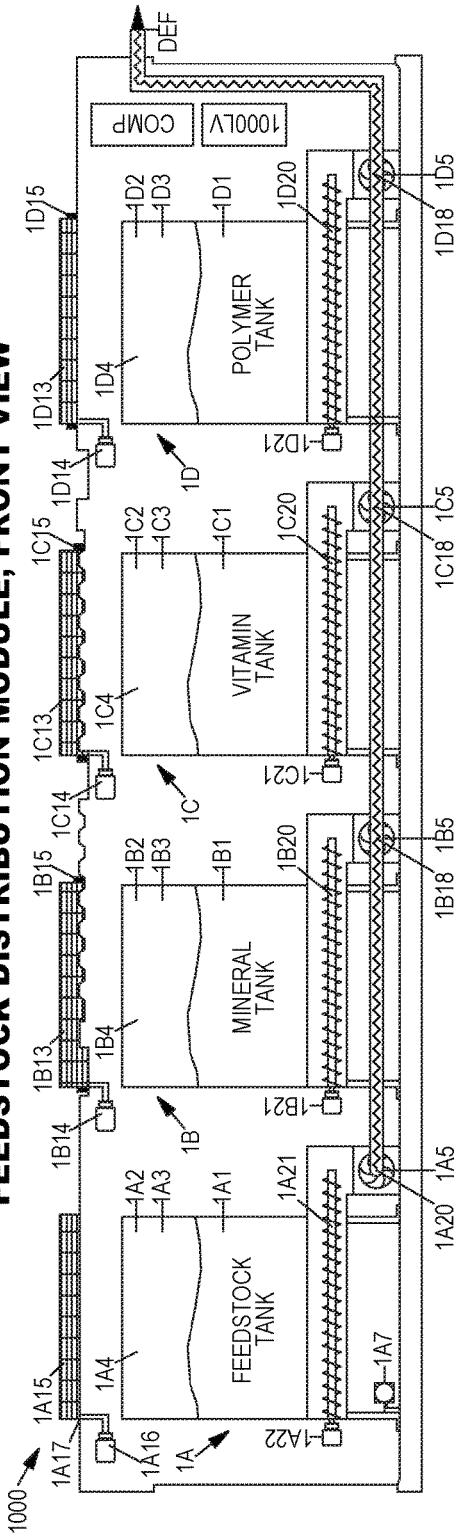

FEEDSTOCK DISTRIBUTION MODULE, SIDE VIEW

WATER DISTRIBUTION MODULE, FRONT VIEW

WATER DISTRIBUTION MODULE, TOP VIEW

WATER DISTRIBUTION MODULE, SIDE VIEW

ENHANCED FEEDSTOCK DISTRIBUTION MODULE, FRONT VIEW

ENHANCED FEEDSTOCK DISTRIBUTION MODULE, TOP VIEW

ENHANCED FEEDSTOCK DISTRIBUTION MODULE, SIDE VIEW

INSECT FEEDING MODULE, FRONT VIEW

INSECT FEEDING MODULE, TOP VIEW

INSECT FEEDING MODULE, SIDE VIEW

INSECT EVACUATION MODULE, FRONT VIEW

INSECT EVACUATION MODULE, TOP VIEW

INSECT EVACUATION MODULE, SIDE VIEW

INSECT BREEDING MODULE, FRONT VIEW

INSECT BREEDING MODULE, TOP VIEW

INSECT BREEDING MODULE, CONVEYOR SIDE VIEW (CSV)

INSECT BREEDING MODULE, CONVEYOR SIDE VIEW (CSV)

HATCHED INSECT SEPARATION MODULE, FRONT VIEW

HATCHED INSECT SEPARATION MODULE, TOP VIEW

HATCHED INSECT SEPARATION MODULE, SIDE VIEW

FIGURE 40

| | TABLE 1 | | |
|---|---|---|---|
| | COLUMN 1 (C1) | COLUMN 2 (C2) | COLUMN 3 (C3) |
| ROW 1 (R1) | Feedstock Mineral Enhancers | lb/ton of feed | lb/ton of feed |
| ROW 2 (R2) | potassium | 0.5 | 250 |
| ROW 3 (R3) | chloride | 0.5 | 250 |
| ROW 4 (R4) | sodium | 0.5 | 250 |
| ROW 5 (R5) | calcium | 0.5 | 250 |
| ROW 6 (R6) | phosphorous | 0.5 | 250 |
| ROW 7 (R7) | magnesium | 0.5 | 150 |
| ROW 8 (R8) | zinc | 0.5 | 150 |
| ROW 9 (R9) | iron | 0.5 | 150 |
| ROW 10 (R10) | manganese | 0.5 | 150 |
| ROW 11 (R11) | copper | 0.5 | 150 |
| ROW 12 (R12) | iodine | 0.5 | 150 |
| ROW 13 (R13) | selenium | 0.5 | 150 |
| ROW 14 (R14) | molybdenum | 0.5 | 150 |
| ROW 15 (R15) | | | |
| ROW 16 (R16) | Feedstock Vitamin Enhancers | lb/ton of feed | lb/ton of feed |
| ROW 17 (R17) | B1 | 5 | 750 |
| ROW 18 (R18) | B2 | 5 | 750 |
| ROW 19 (R19) | E | 5 | 750 |
| ROW 20 (R20) | | | |
| ROW 21 (R21) | | lb/lb of feed | lb/lb of feed |
| ROW 22 (R22) | A | 10 | 950 |
| ROW 23 (R23) | | | |
| ROW 24 (R24) | Feedstock Fiber Enhancers | lb/ton of feed | lb/ton of feed |
| ROW 25 (R25) | fiber | 15 | 100 |
| ROW 26 (R26) | | | |
| ROW 27 (R27) | Other 'Energy Insect' Enhancers | lb/ton of feed | lb/ton of feed |
| ROW 28 (R28) | niacin | 5 | 300 |
| ROW 29 (R29) | taurine | 5 | 300 |
| ROW 30 (R30) | glucuronic acid | 5 | 300 |
| ROW 31 (R31) | malic acid | 5 | 300 |
| ROW 32 (R32) | N-acetyl L tyrosine | 5 | 300 |
| ROW 33 (R33) | L-phenylalanine | 5 | 300 |
| ROW 34 (R34) | caffeine | 5 | 750 |
| ROW 35 (R35) | citicoline | 5 | 300 |

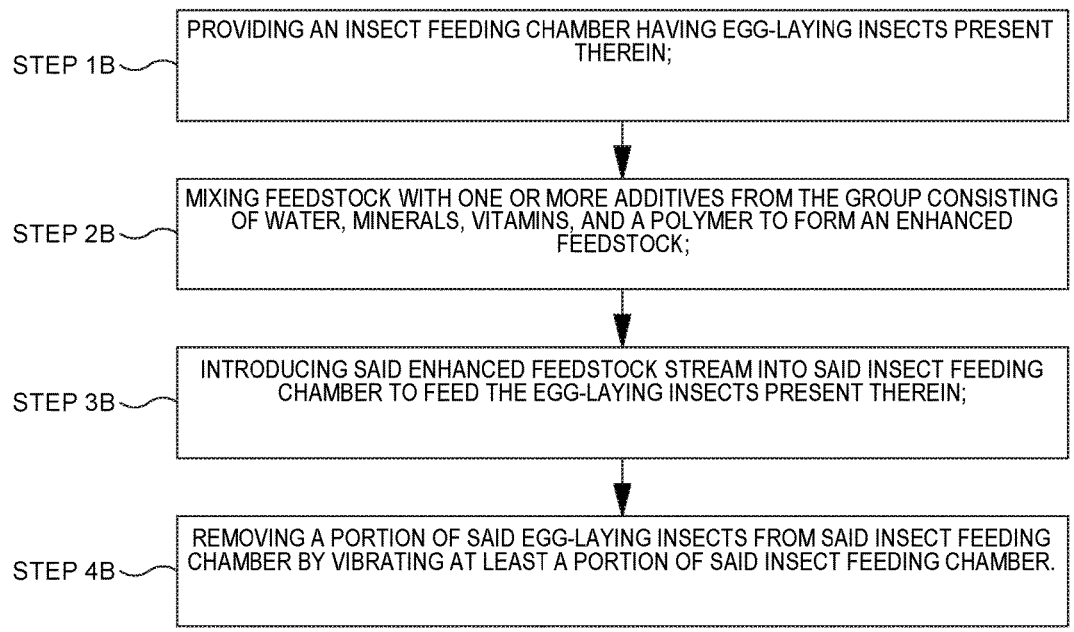

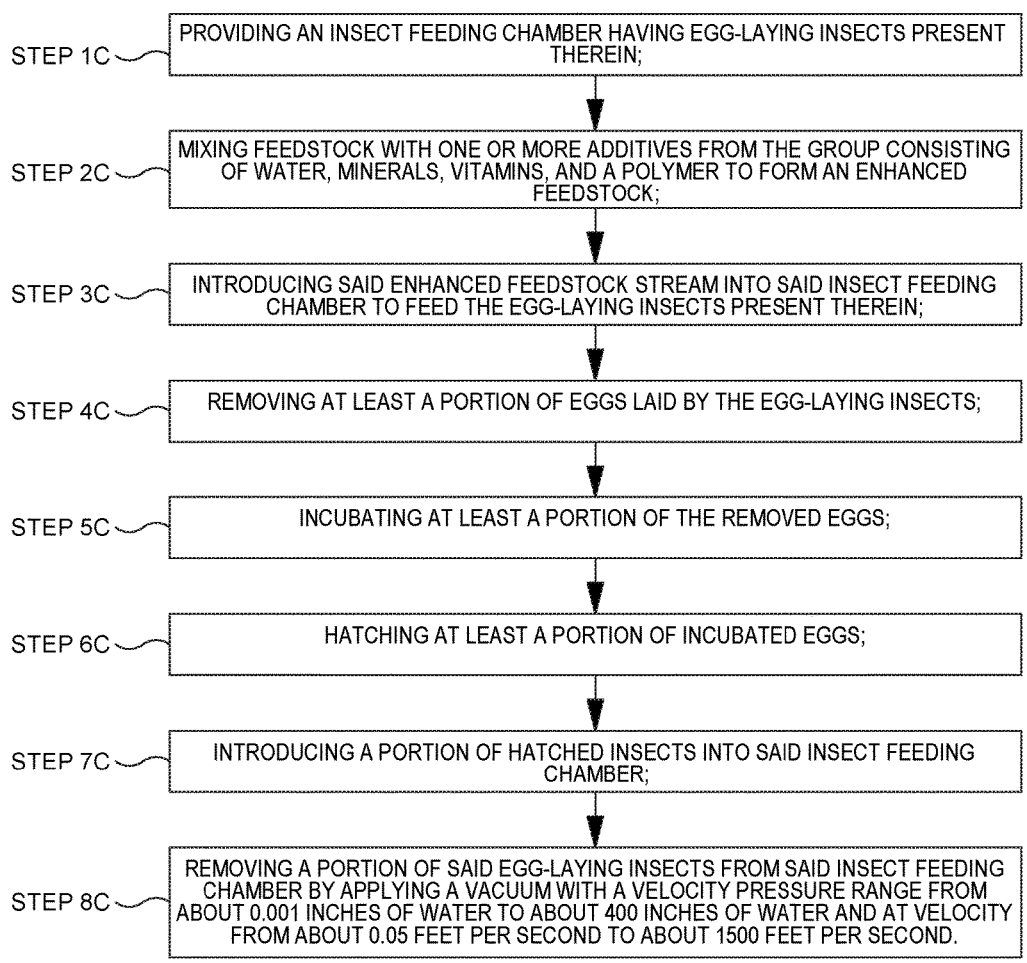

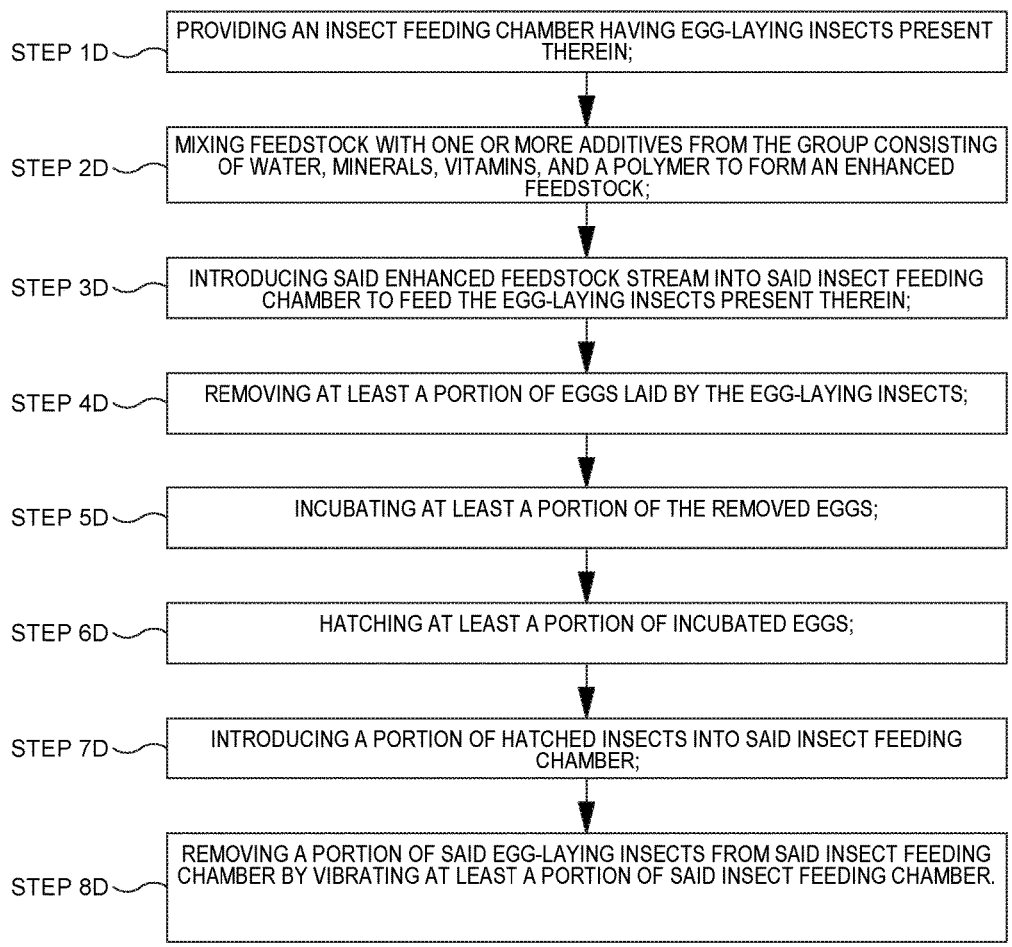

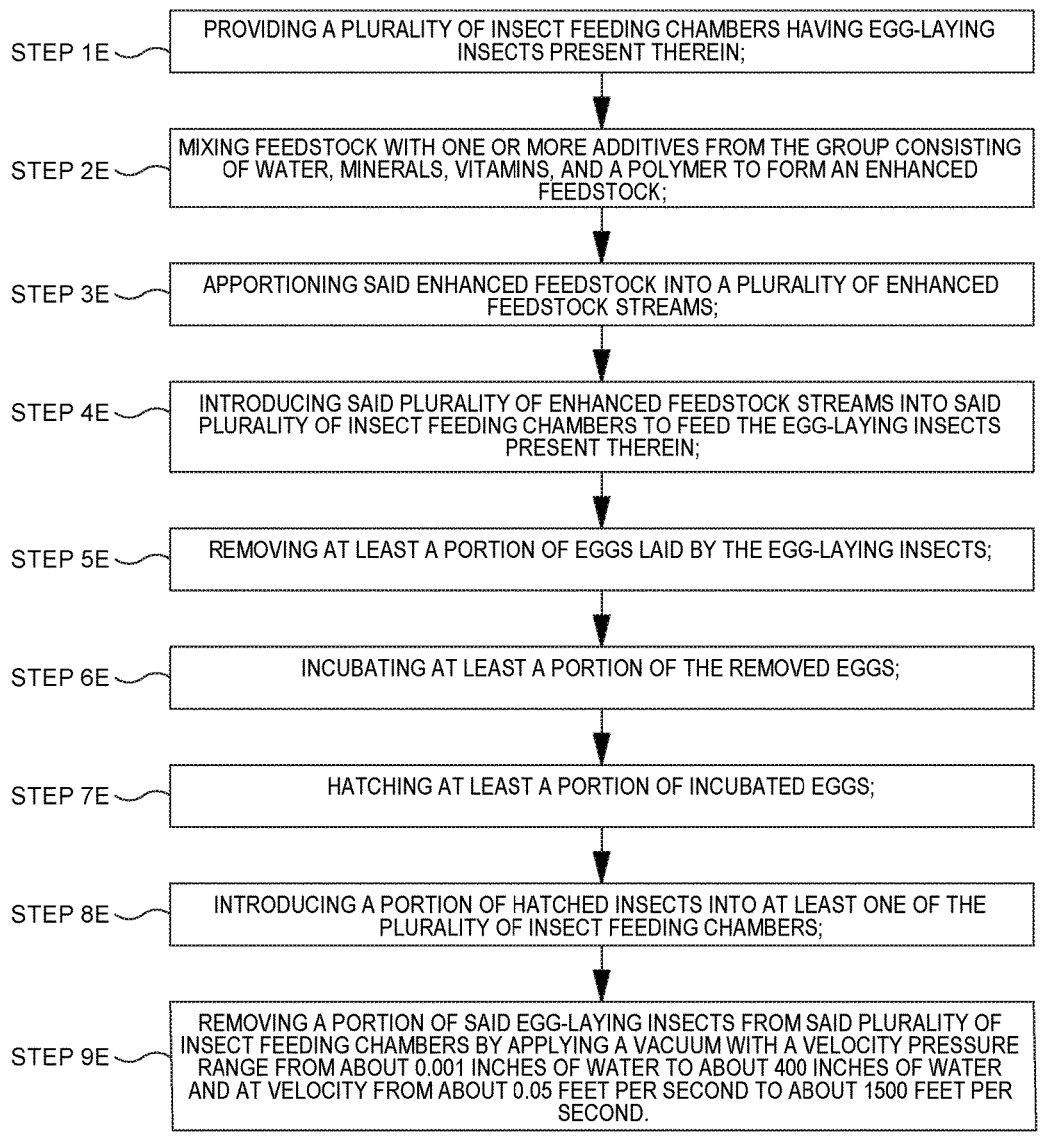

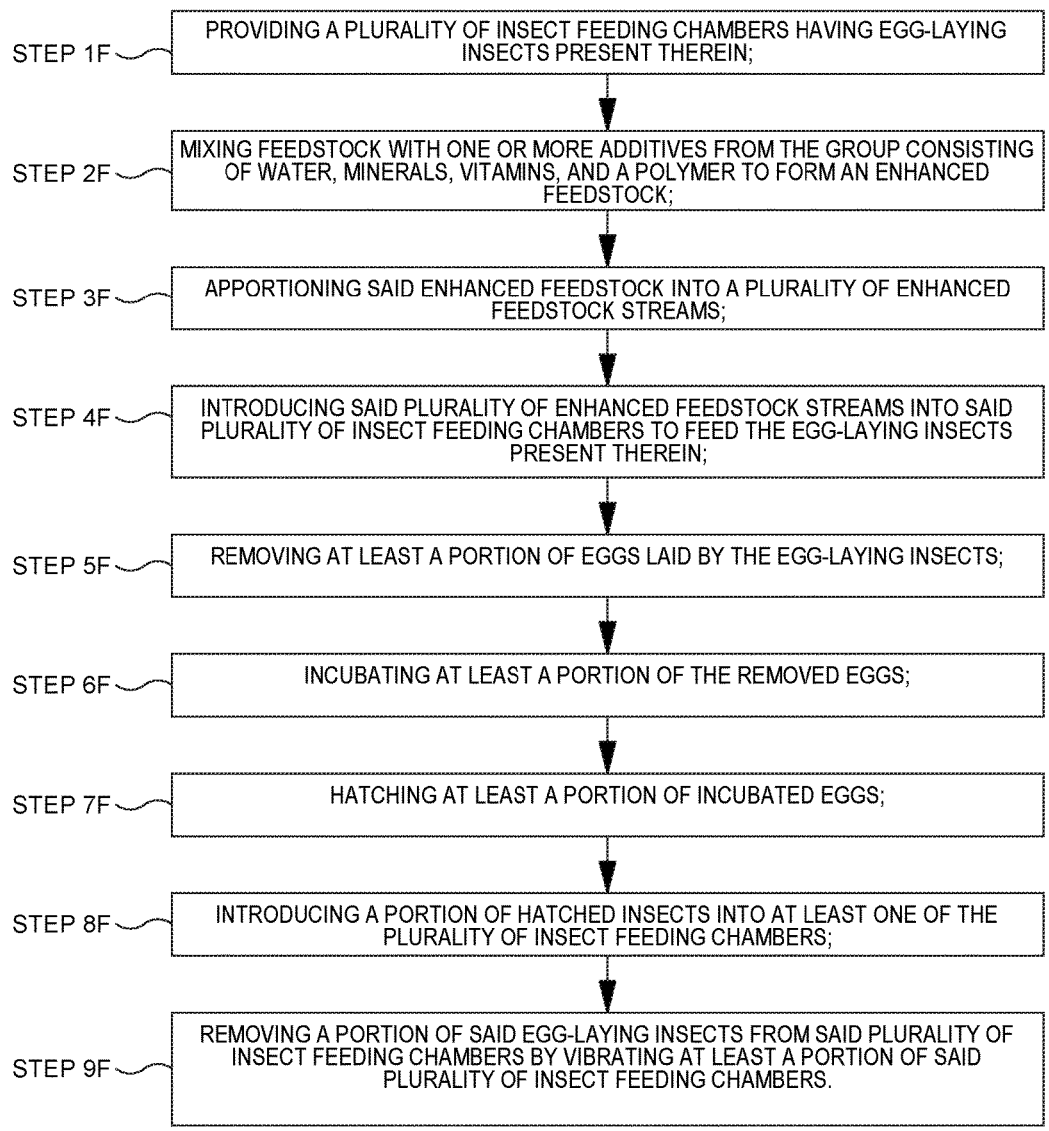

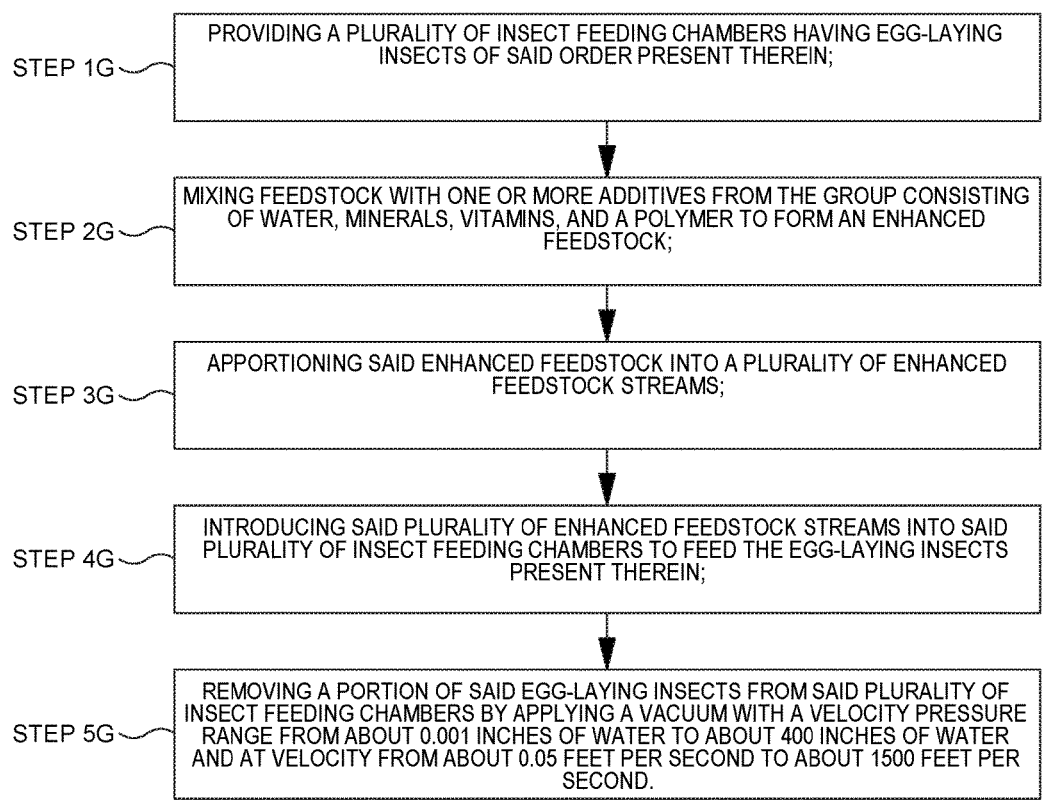

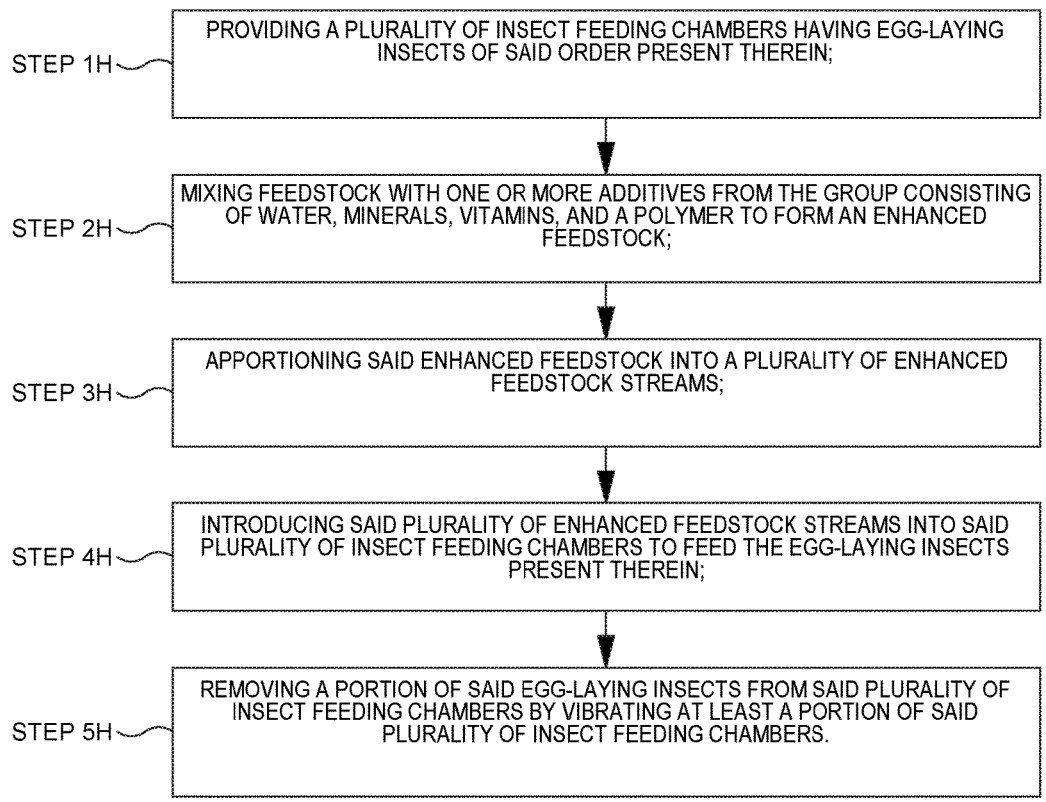

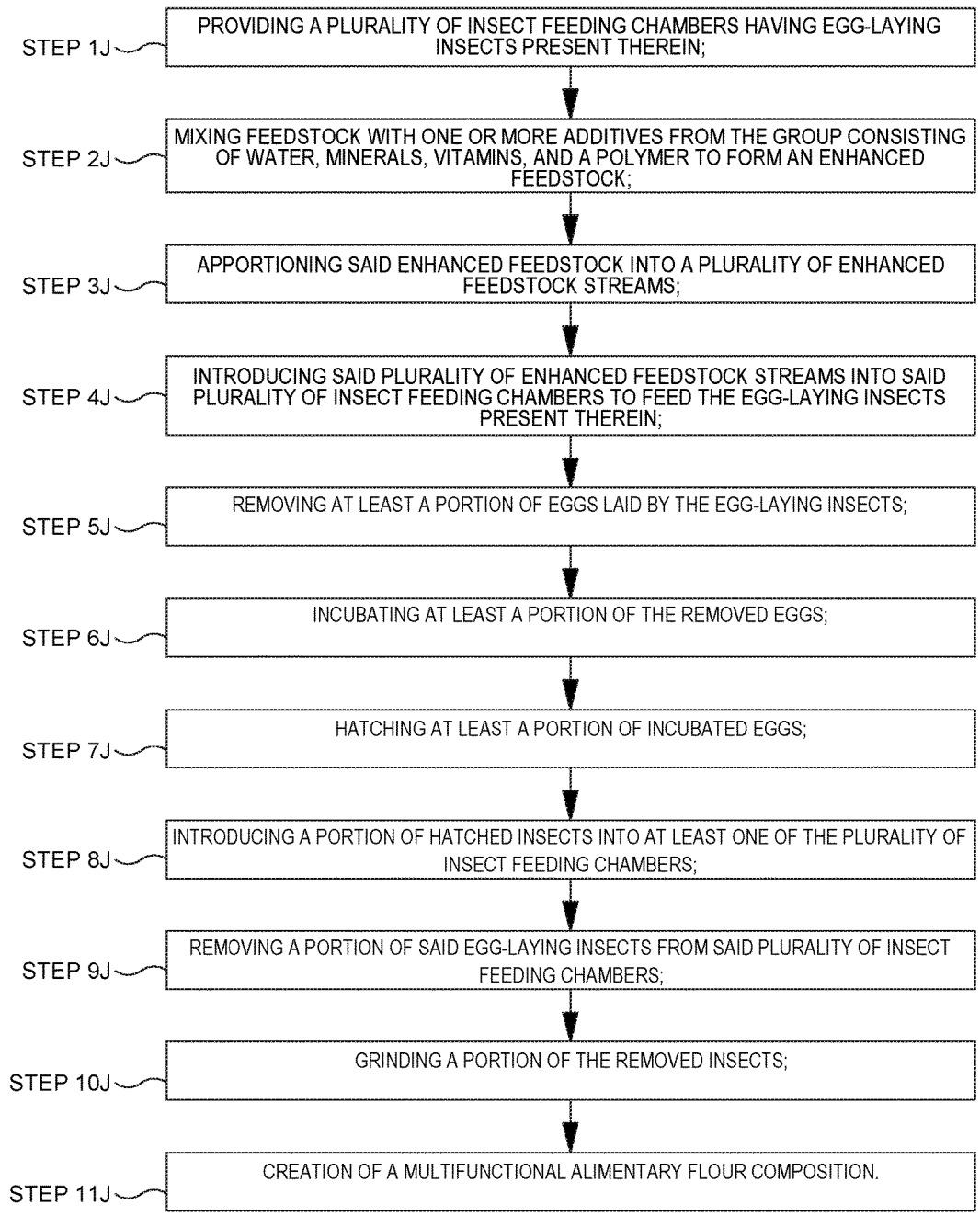

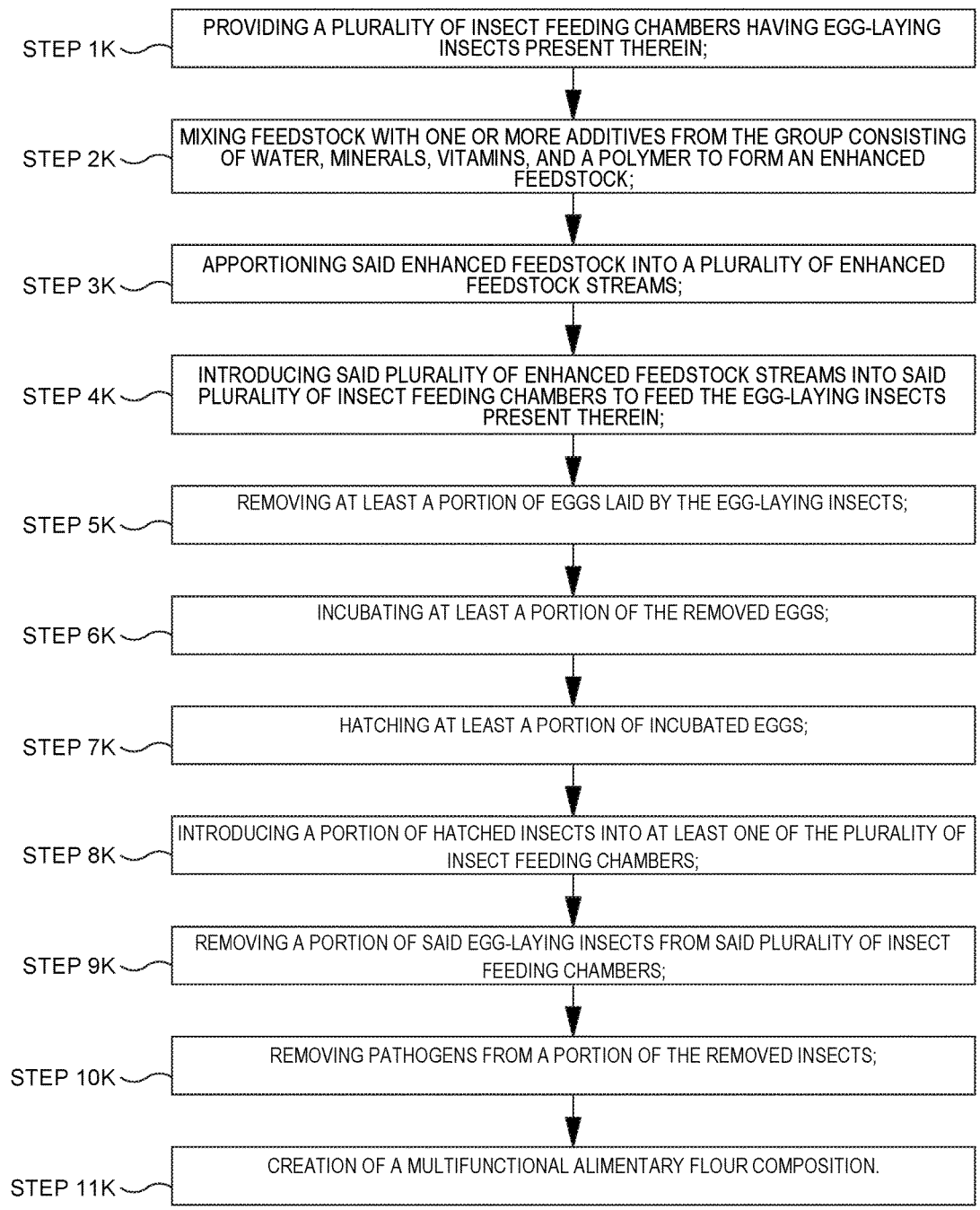

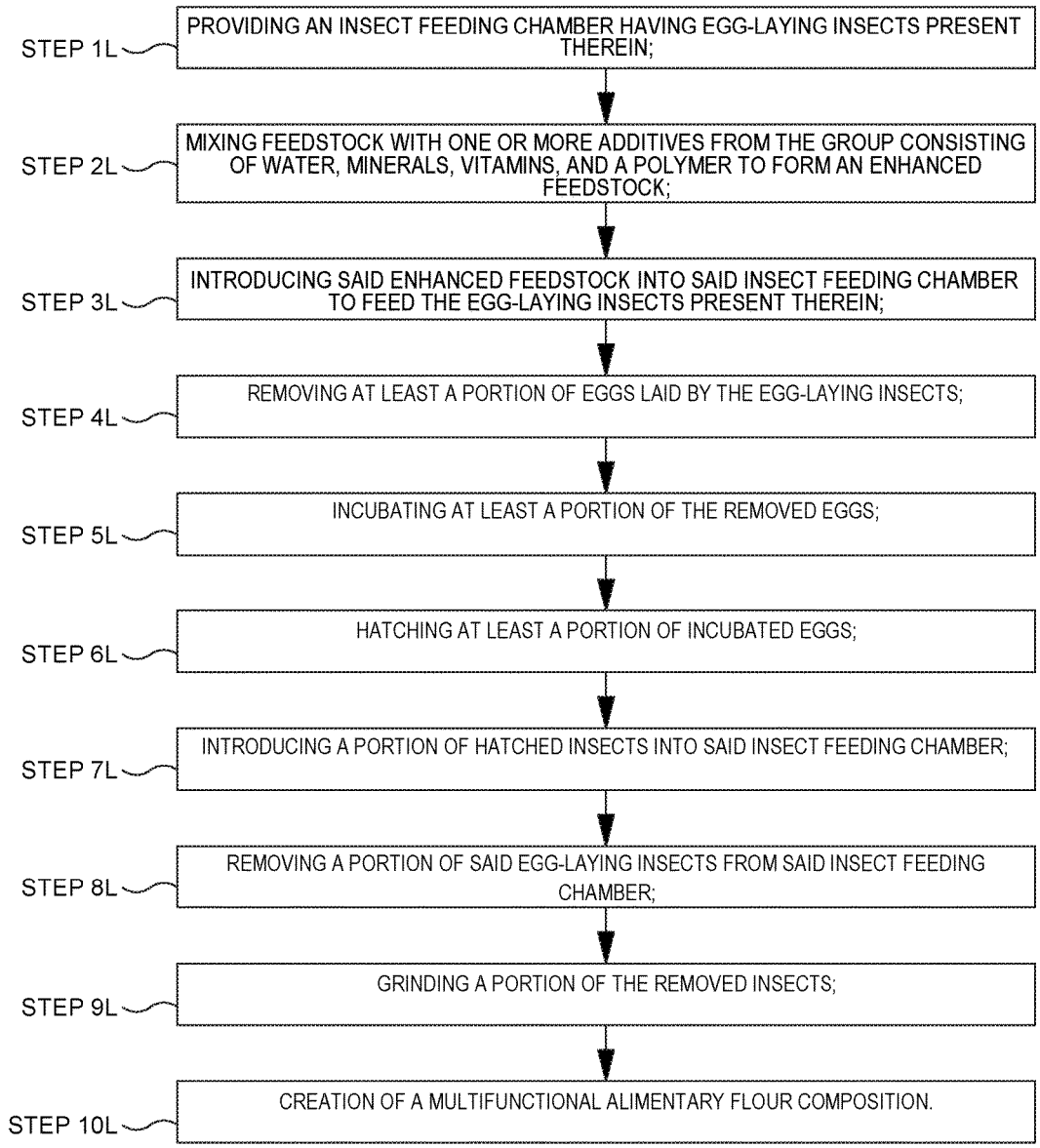

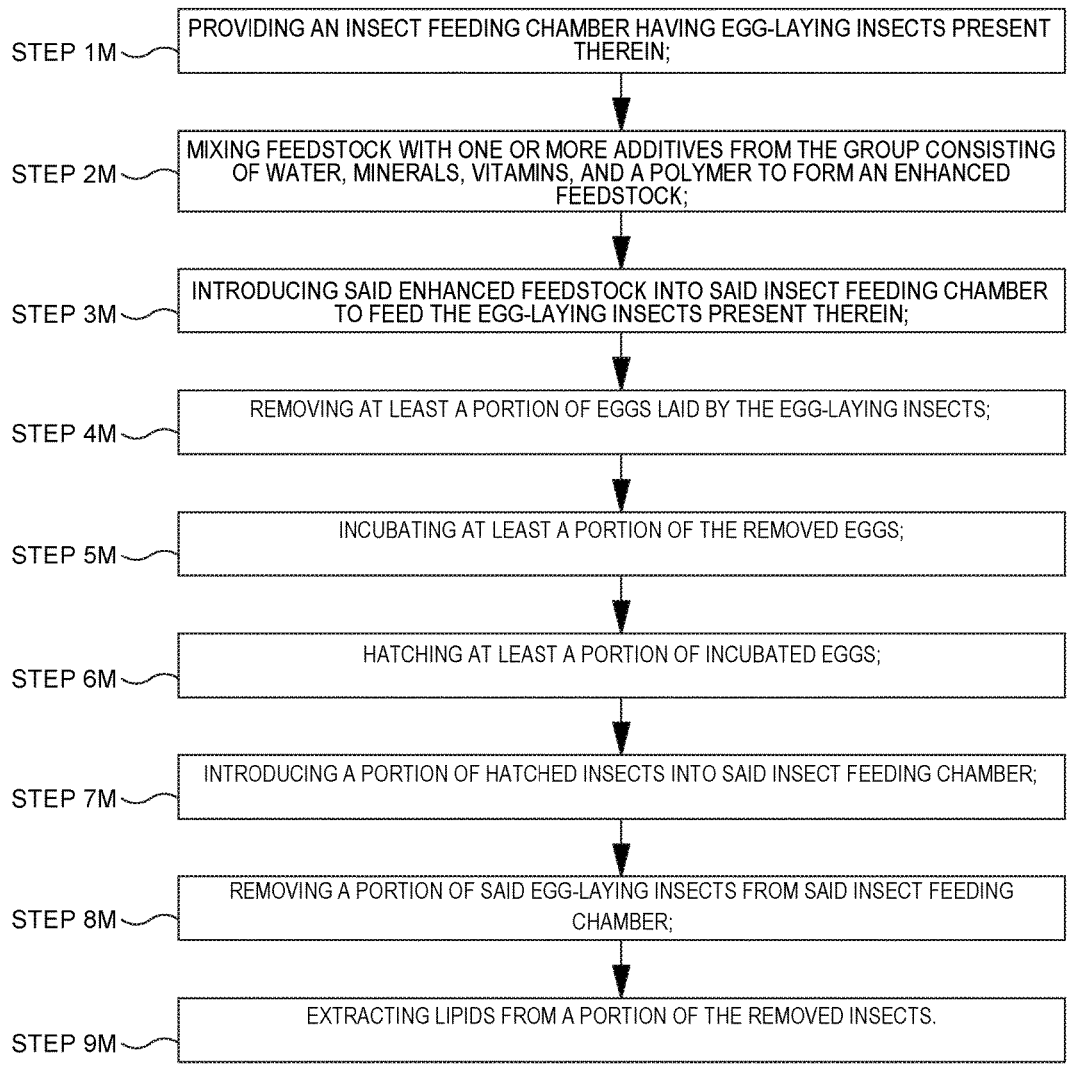

INSECT PRODUCTION SYSTEMS AND METHODS

TECHNICAL FIELD

The present disclosure relates to the field of commercial scale production of Orthoptera order of insects.

BACKGROUND

Efficient, reliable, and consistent computer operated insect rearing facilities are needed to meet the insect production demands of society. In recent years, there has been an increasing demand for insect protein for human and animal consumption. There is also promise for the extraction and use of lipids from insects for applications involving medicine, nanotechnology, consumer products, and chemical production. Large scale insect production systems must be designed responsibly to make sure that the insects are freed from hunger, thirst, discomfort, pain, injury, disease, fear and distress. These systems must be precisely sized and situated to be able to provide systematically timed and controlled computer operated methods to maintain a sufficient amount of nutrition, to prevent disease, cannibalism, and injury. A need exists for mass insect production facilities that maximize insect production on a small physical outlay while providing adequate space for high density insect rearing.

The ability to grow insects on a continuous basis with minimal human interaction has been long regarded as desirable or needed to facilitate widespread use for human and animal or consumption or for use as an intermediate lipid-based product for the production of food and chemicals. In demographics, the world population is the total number of humans currently living. As of March 2016, it was estimated at 7.4 billion, an all-time record high. The United Nations estimates it will further increase to 11.2 billion in the year 2100. World population has experienced continuous growth since the end of the Great Famine of 1315-17 and the Black Death in 1350, when it was near 370 million.

In coming years, nuclear proliferation, food shortages, water scarcity, economic agendas and corruption, and diminishing petroleum reserves may result in a constraint on access to food, water, chemicals, and other resources. Famine may result causing millions of deaths over an extended number of years which will mark a clear end to the period of growth and prosperity for the human civilization, industrialization, and globalization.

The global population is expected to reach between 8.3 and 10.9 billion by 2050 which will be met with famine, malnutrition, and shortages of clean drinking water. Further, the succession of major wars, famines, and other disasters may result in large-scale population losses if no alternate source or food and chemicals is immediately put in place.

Thus, it is of paramount importance that large-scale, modular, easily manufacturable, energy efficient, reliable, computer operated insect production facilities are extensively deployed to produce insects for human and animal consumption, and for the extraction and use of lipids for applications involving medicine, nanotechnology, consumer products, and chemical production with minimal water, feedstock, and environmental impact.

There is a need for systems and methods that can clean and decontaminate water from the most-harshest of environmental conditions and provide a clean water source suitable to feed and grow insects for human, animal, and chemical production. There is a need to develop and vastly implement large-scale, systematic insect feeding and breeding facilities that can accommodate the protein and fatty acid demands of society. There is a need to re-use old containerized shipping containers to promote the implementation of widespread commercial production of insects to promote regional, rural, and urban, job opportunities that maximizes the quality of living the insects that are farmed.

SUMMARY

Herein disclosed are innovative and advanced systems and methods related to the production of minilivestock with a specific focus on commercial scale production of Orthoptera order of insects.

In embodiments, the present disclosure describes a method for raising Orthoptera order of insects to generate a multifunctional alimentary flour composition, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into said insect feeding chamber; (h) removing a portion of said egg-laying insects from said insect feeding chamber; (i) grinding a portion of the removed insects to form a stream of ground insects; and, (j) creating of a multifunctional alimentary flour composition by mixing ground insects of step (i) with one or more ingredients from the group consisting of *cannabis* enhancers, fiber-starch materials, binding agents, density improving textural supplements, and moisture improving textural supplements.

In embodiments, the insect feeding chamber operates at a water to insect ratio ranging from between about 0.1 ton of water per ton of insects produced to about 20 tons of water per ton of insects produced. In embodiments, the insect feeding chamber operates at a feedstock to insect ratio ranging from between about 1 ton of feedstock per ton of insects produced to about 5 tons of feedstock per ton of insects produced.

In embodiments, the feedstock is comprised of one or more from the group consisting of agriculture residue, alcohol production coproducts, animal waste, animal waste, bio-waste, compost, crop residues, energy crops, fermentation waste, fermentative process wastes, food processing residues, food waste, garbage, industrial waste, livestock waste, municipal solid waste, plant matter, poultry wastes, rice straw, sewage, spent grain, spent microorganisms, urban waste, vegetative material, and wood waste.

In embodiments, the feeding chamber produces insects with a fat content ranging from between 5% to about 60%. In embodiments, the feeding chamber produces insects having fatty acids comprised of one or more from the group consisting of palmitoleic acid, linoleic acid, alpha-linoleic acid, oleic acid, gamma-linoleic acid, and stearic acid.

In embodiments, the feeding chamber grows insects within it over a time duration ranging from between about 1 week to about 15 weeks. In embodiments, pathogen may be removed from a portion of the insects removed after step (i) and before step (j). In embodiments, pathogens are removed by heating said removed insects to a temperature ranging from between about 110 degrees Fahrenheit to about 550 degrees Fahrenheit. In embodiments, pathogens are removed by the application of microwave radiation.

In embodiments, the egg-laying insects are removed from the feeding chamber in step (h) by applying a vacuum with a velocity pressure range from about 0.001 inches of water to about 400 inches of water and at velocity from about 0.05 feet per second to about 1500 feet per second. In embodiments, a portion of said egg-laying insects are removed in step (h) by vibrating at least a portion of said insect feeding chamber. In embodiments, eggs laid by the egg-laying insects may be removed by transferring said eggs into a breeding material that is provided by a conveyor. In embodiments, at least a portion of the removed eggs are incubated at a temperature ranging from between about 60 degrees Fahrenheit to about 90 degrees Fahrenheit. In embodiments, at least a portion of the removed eggs are incubated over a time duration ranging from between about 1 week to about 3 weeks.

In embodiments, the fiber-starch materials are comprised of one or more from the group consisting of cereal-grain-based materials, grass-based materials, nut-based materials, powdered fruit materials, root-based materials, tuber-based materials, and vegetable-based materials. In embodiments, the binding agents are comprised of one or more from the group consisting of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugars, syrups, tapioca, vegetable gums, and xanthan gum. In embodiments, the density improving textural supplements are comprised of one or more from the group consisting of extracted arrowroot starch, extracted corn starch, extracted lentil starch, extracted potato starch, and extracted tapioca starch. In embodiments, the moisture improving textural supplements are comprised of one or more from the group consisting of almonds, brazil nuts, cacao, cashews, chestnuts, coconut, filberts, hazelnuts, indian nuts, macadamia nuts, nut butters, nut oils, nut powders, peanuts, pecans, pili nuts, pine nuts, pinon nuts, pistachios, soy nuts, sunflower seeds, tiger nuts, and walnuts. In embodiments, the minerals are comprised of one or more from the group consisting of a potassium, chloride, sodium, calcium, phosphorous, magnesium, zinc, iron, manganese, copper, iodine, selenium, and molybdenum. In embodiments, the vitamins are comprised of one or more from the group consisting of vitamin B1, vitamin B2, vitamin E, and vitamin A. In embodiments, enhancers are added to the enhanced feedstock said enhancers are comprised of one or more from the group consisting of niacin, taurine, glucuronic acid, malic acid, N-acetyl L tyrosine, L-phenylalanine, caffeine, citicoline, and insect growth hormones.

In embodiments, the multifunctional alimentary flour created in step (j) ranges from between about 25 pounds of *cannabis* enhancer per ton of multifunctional alimentary flour to about 1800 pounds of *cannabis* enhancer per ton of multifunctional alimentary flour. In embodiments, the *cannabis* enhancer includes volatile feedstock components.

In embodiments, the feedstock may be mixed with one or more additives is comprised of one or more from the group consisting of: mixing polymer with the feedstock at a polymer to feedstock ratio ranging from between about 15 pounds of polymer per pound of feedstock to about 100 pounds of polymer per pound of feed, mixing potassium with the feedstock at a potassium to feedstock ratio ranging from between about 0.5 pounds of potassium per ton of feedstock to about 250 pounds of potassium per ton of feedstock, mixing chloride with the feedstock at a chloride to feedstock ratio ranging from between about 0.5 pounds of chloride per ton of feedstock to about 250 pounds of chloride per ton of feedstock, mixing sodium with the feedstock at a sodium to feedstock ratio ranging from between about 0.5 pounds of sodium per ton of feedstock to about 250 pounds of sodium per ton of feedstock, mixing calcium with the feedstock at a calcium to feedstock ratio ranging from between about 0.5 pound of calcium per ton of feedstock to about 250 pounds of calcium per ton of feedstock, mixing phosphorous with the feedstock at a phosphorous to feedstock ratio ranging from between about 0.5 pounds of phosphorous per ton of feedstock to about 250 pounds of phosphorous per ton of feedstock, mixing magnesium with the feedstock at a magnesium to feedstock ratio ranging from between about 0.5 pound of magnesium per ton of feedstock to about 150 pounds of magnesium per ton of feedstock, mixing zinc with the feedstock at a zinc to feedstock ratio ranging from between about 0.5 pounds of zinc per ton of feedstock to about 150 pounds of zinc per ton of feedstock, mixing iron with the feedstock at an iron to feedstock ratio ranging from between about 0.5 pounds of iron per ton of feedstock to about 150 pounds of iron per ton of feedstock, mixing manganese with the feedstock at a manganese to feedstock ratio ranging from between about 0.5 pounds of manganese per ton of feedstock to about 150 pounds of manganese per ton of feedstock, mixing copper with the feedstock at a copper to feedstock ratio ranging from between about 0.5 pounds of copper per ton of feedstock to about 150 pounds of copper per ton of feedstock, mixing vitamin B1 with the feedstock at a vitamin B1 to feedstock ratio ranging from between about 5 pounds of vitamin B1 per ton of feedstock to about 750 pounds of vitamin B1 per ton of feed, mixing vitamin B2 with the feedstock at a vitamin B2 to feedstock ratio ranging from between about 5 pounds of vitamin B2 per ton of feedstock to about 750 pounds of vitamin B2 per ton of feed, mixing vitamin E with the feedstock at a vitamin E to feedstock ratio ranging from between about 5 pounds of vitamin E per ton of feedstock to about 750 pounds of vitamin E per ton of feed, mixing vitamin A with the feedstock at a vitamin A to feedstock ratio ranging from between about 10 pounds of vitamin A per pound of feedstock to about 750 pounds of vitamin A per pound of feed, mixing niacin with the feedstock at a niacin to feedstock ratio ranging from between about 5 pounds of niacin per pound of feedstock to about 300 pounds of niacin per pound of feedstock, mixing taurine with the feedstock at a taurine to feedstock ratio ranging from between about 5 pounds of taurine per pound of feedstock to about 300 pounds of taurine per pound of feedstock, mixing glucuronic acid with the feedstock at a glucuronic acid to feedstock ratio ranging from between about 5 pounds of glucuronic acid per pound of feedstock to about 300 pounds of glucuronic acid per pound of feedstock, mixing malic acid with the feedstock at a malic acid to feedstock ratio ranging from between about 5 pounds of malic acid per pound of feedstock to about 300 pounds of malic acid per pound of feedstock, mixing N-acetyl L tyrosine with the feedstock at a N-acetyl L tyrosine to feedstock ratio ranging from between about 5 pounds of N-acetyl L tyrosine per pound of feedstock to about 300 pounds of N-acetyl L tyrosine per pound of feedstock, mixing L-phenylalanine with the feedstock at a L-phenylalanine to feedstock ratio ranging from between about 5 pounds of L-phenylalanine per pound of feedstock to about 300 pounds of L-phenylalanine per pound of feedstock, mixing caffeine is mixed with the feedstock at a caffeine to feedstock ratio ranging from between about 5 pounds of caffeine per pound of feedstock to about 750 pounds of caffeine per pound of feedstock, and, mixing citicoline is mixed with the feedstock at a citicoline to feedstock ratio ranging from between about 5 pounds of citicoline per pound of feedstock to about 300 pounds of citicoline per pound of feedstock.

BRIEF DESCRIPTION OF THE DRAWINGS

Reference will now be made in detail to various embodiments of the disclosure. Each embodiment is provided by way of explanation of the disclosure, not limitation of the disclosure. In fact, it will be apparent to those skilled in the art that modifications and variations can be made in the disclosure without departing from the teaching and scope thereof. For instance, features illustrated or described as part of one embodiment to yield a still further embodiment derived from the teaching of the disclosure. Thus, it is intended that the disclosure or content of the claims cover such derivative modifications and variations to come within the scope of the disclosure or claimed embodiments described herein and their equivalents.

Additional objects and advantages of the disclosure will be set forth in part in the description which follows, and in part will be obvious from the description, or may be learned by practice of the claims. The objects and advantages of the disclosure will be attained by means of the instrumentalities and combinations and variations particularly pointed out in the appended claims.

Figure 1A:
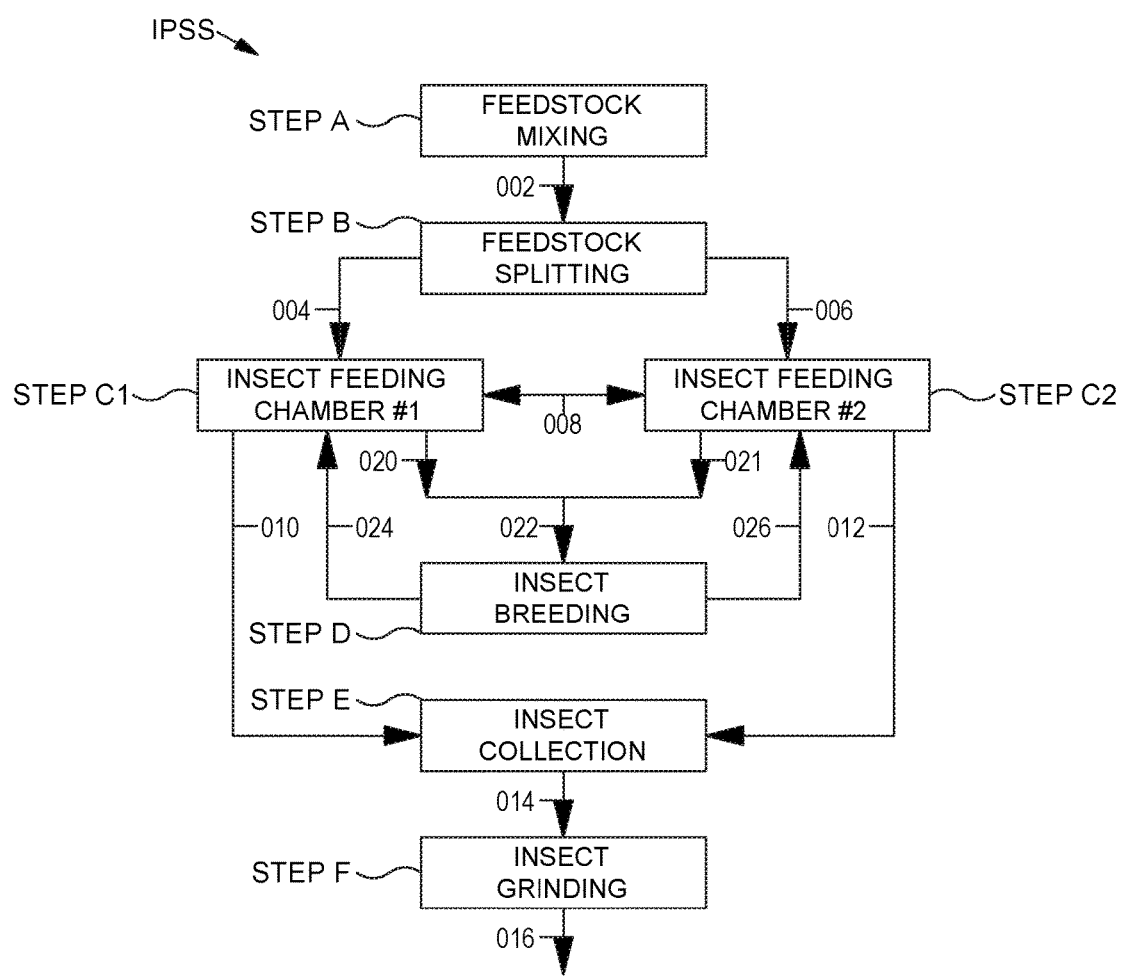

The accompanying figures show schematic process flowcharts of preferred embodiments and variations thereof. A full and enabling disclosure of the content of the accompanying claims, including the best mode thereof to one of ordinary skill in the art, is set forth more particularly in the remainder of the specification, including reference to the accompanying figures showing how the preferred embodiments and other non-limiting variations of other embodiments described herein may be carried out in practice, in which:

FIG. 1A shows a simplistic block flow diagram of one embodiment of an Insect Production Superstructure System (IPSS) including the sequence steps of feedstock mixing (step A), feedstock splitting (step B), insect feeding (step C1, C2), insect breeding (step D), insect collection (step E), and insect grinding (step F).

FIG. 1B elaborates upon the non-limiting embodiment of FIG. 1 further including the sequence steps of pathogen removal (step G) and multifunctional flour mixing (step H).

Figure 1C:
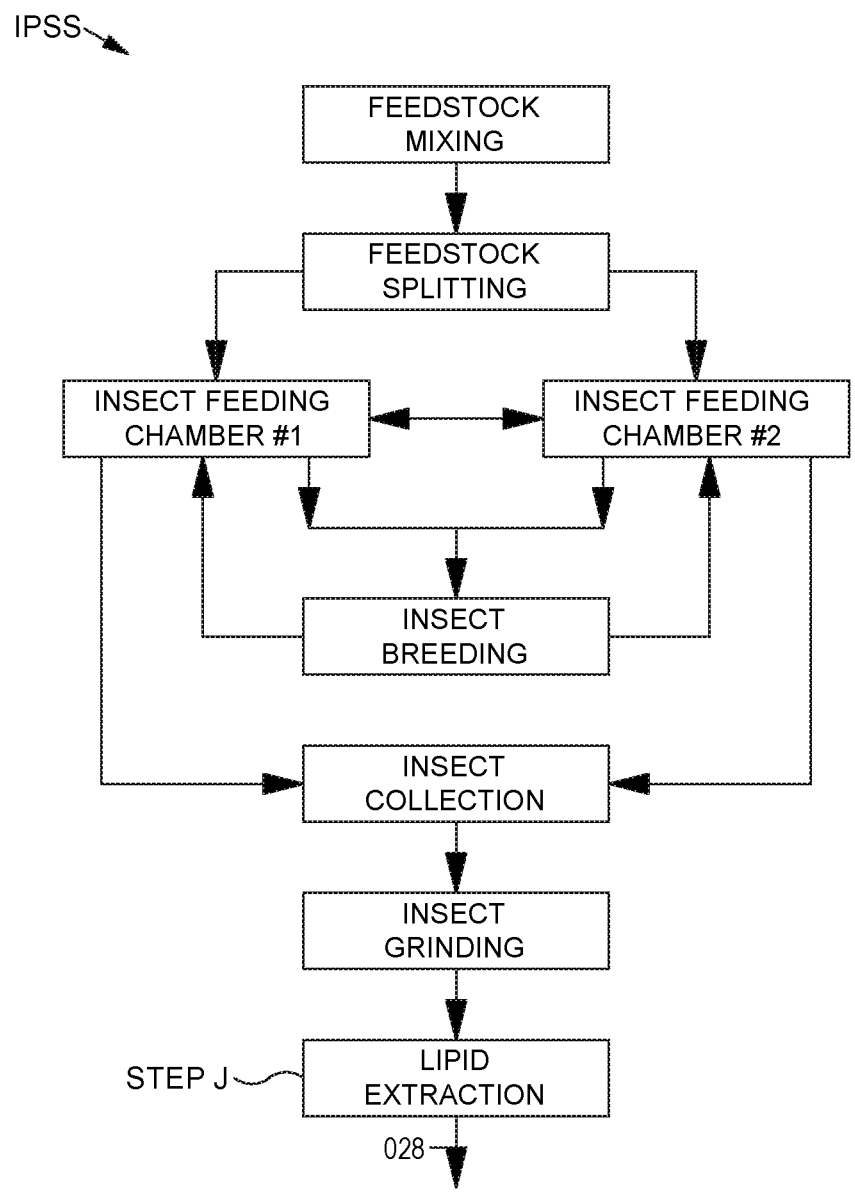

FIG. 1C elaborates upon the non-limiting embodiment of FIG. 1 further including the sequence step of lipid extraction (step J).

Figure 2:
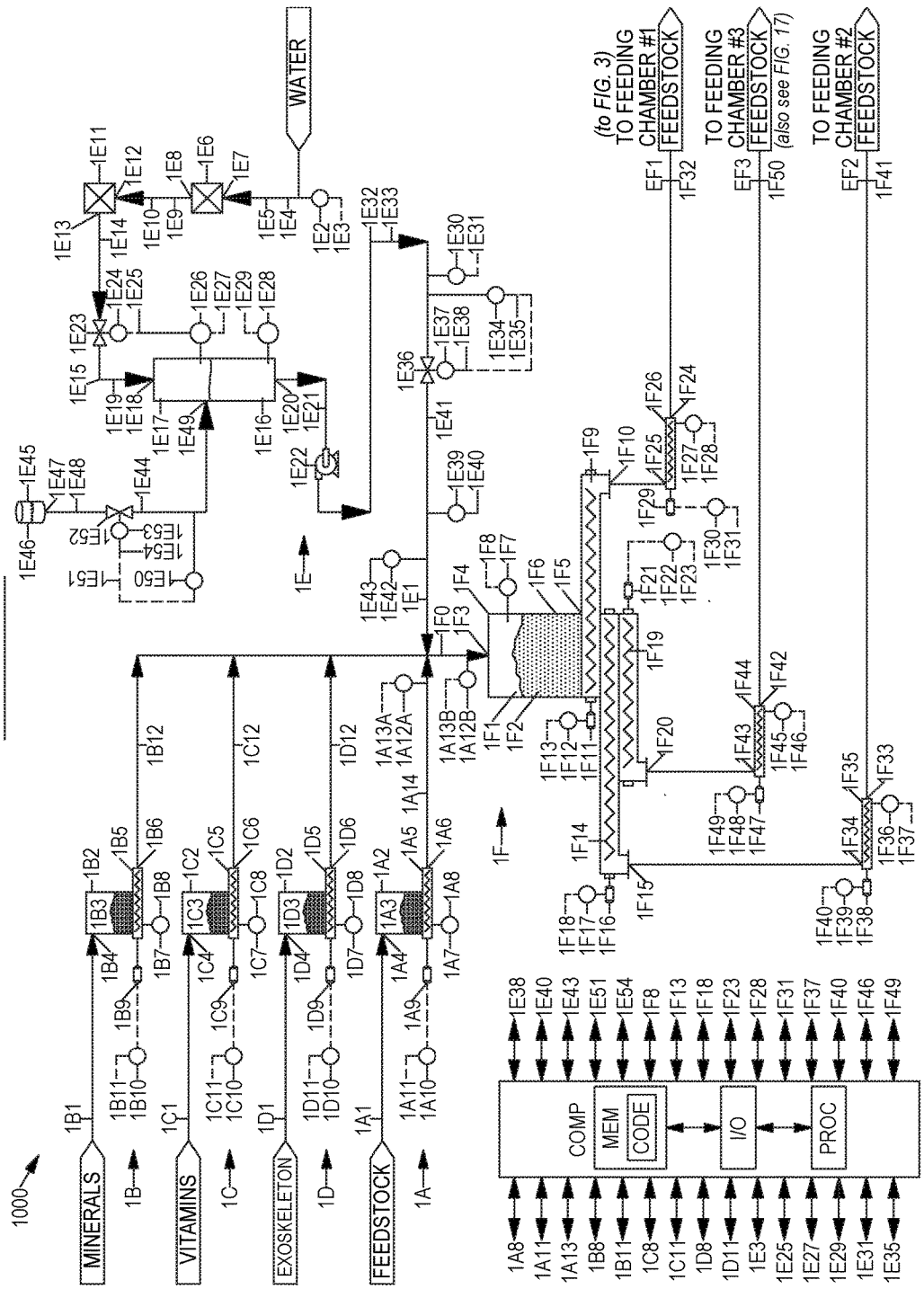

FIG. 2 shows a non-limiting embodiment of an enhanced feedstock mixing module (1000) including a feedstock distribution module (1A), mineral distribution module (1B), vitamin distribution module (1C), polymer distribution module (1D), water distribution module (1E), and an enhanced feedstock distribution module (1F).

Figure 3:
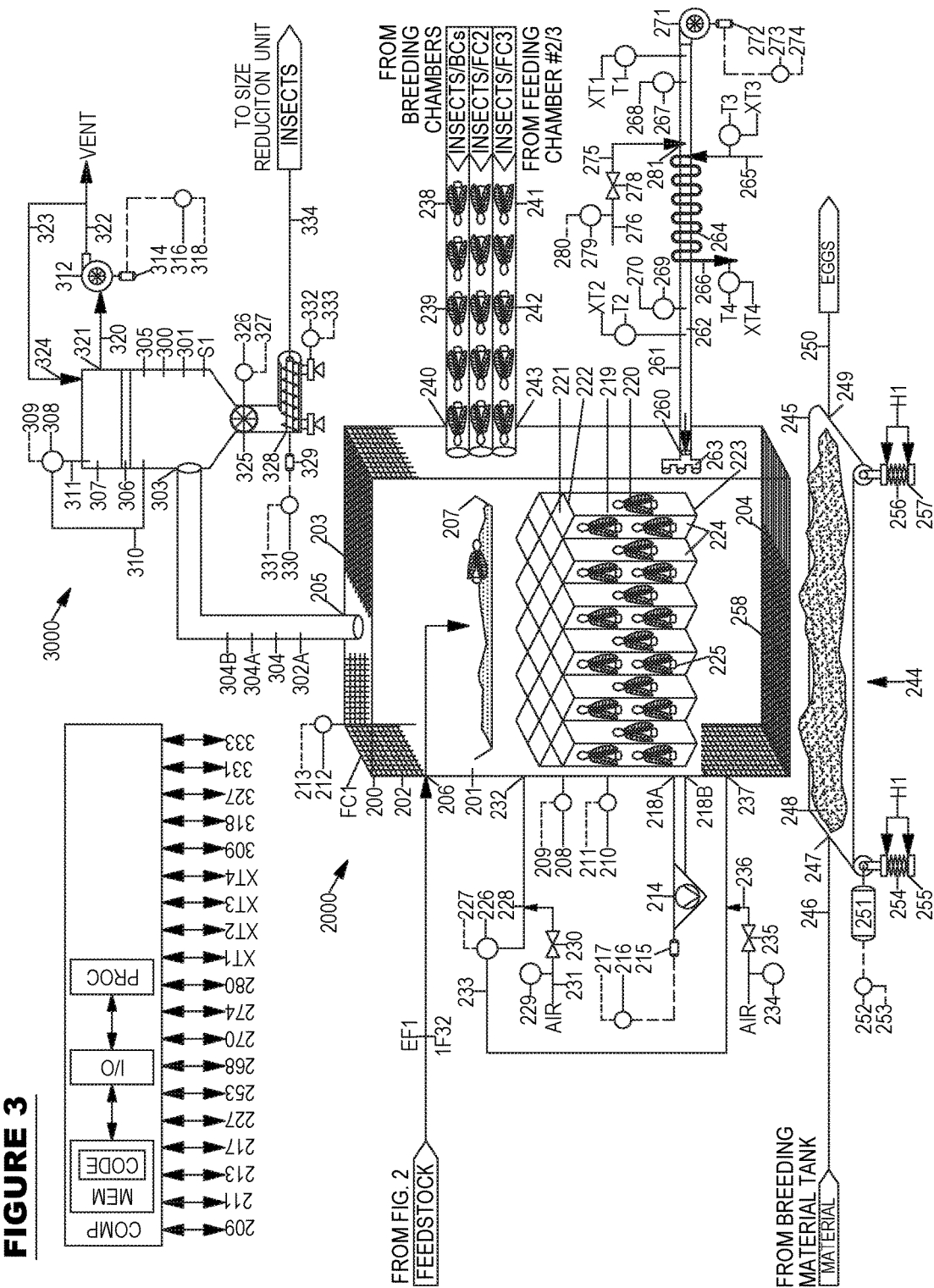

FIG. 3 shows a non-limiting embodiment of an insect feeding module (2000) integrated with an insect evacuation module (3000) operating in a first mode of operation wherein the egg transfer system (244) of the insect feeding module (2000) is at a first state in a first retracted height (H1).

Figure 4:
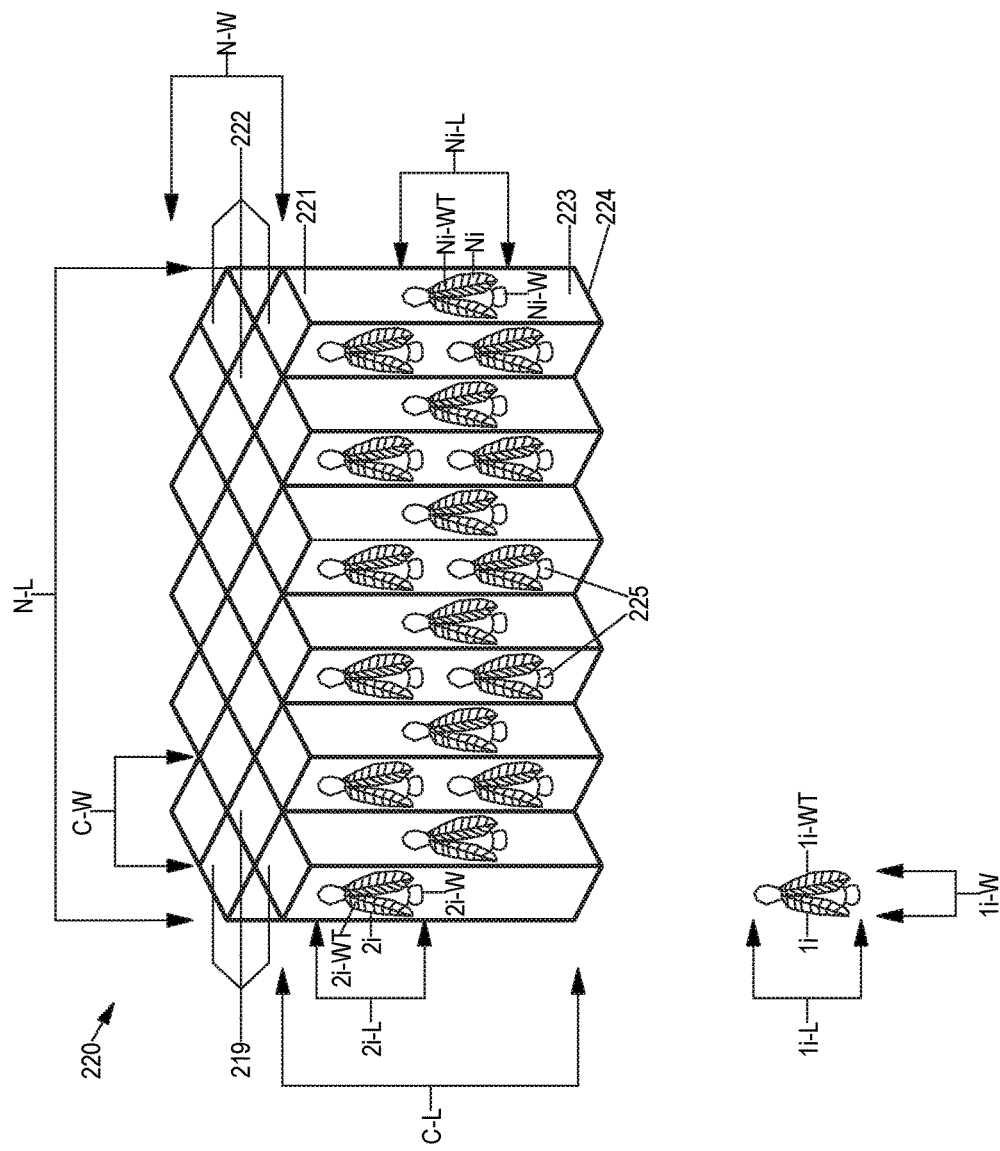

FIG. 4 shows one non-limiting embodiment of a network (220) of cells (219) for growing insects within a feeding chamber (200) of the insect feeding module (2000) shown in FIG. 3.

Figure 5:
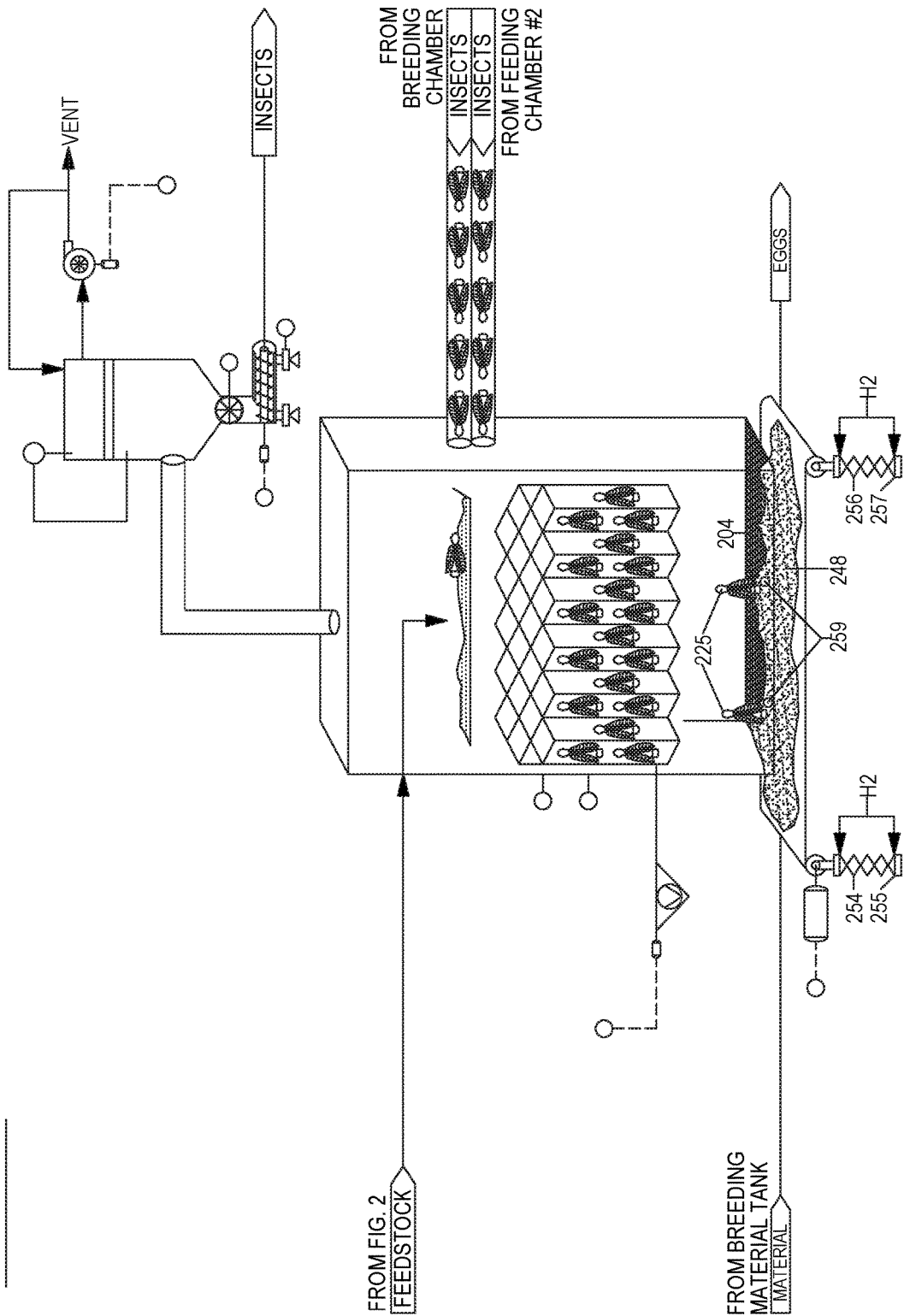

FIG. 5 elaborates upon the non-limiting embodiment of FIG. 3 but shows the insect feeding module (2000) operating in a second mode of operation wherein the egg transfer system (244) of the insect feeding module (2000) is at a second state at a second elevated height (H2) so as to permit insects (225) to lay eggs (259) within a provided breeding material (248).

Figure 6:
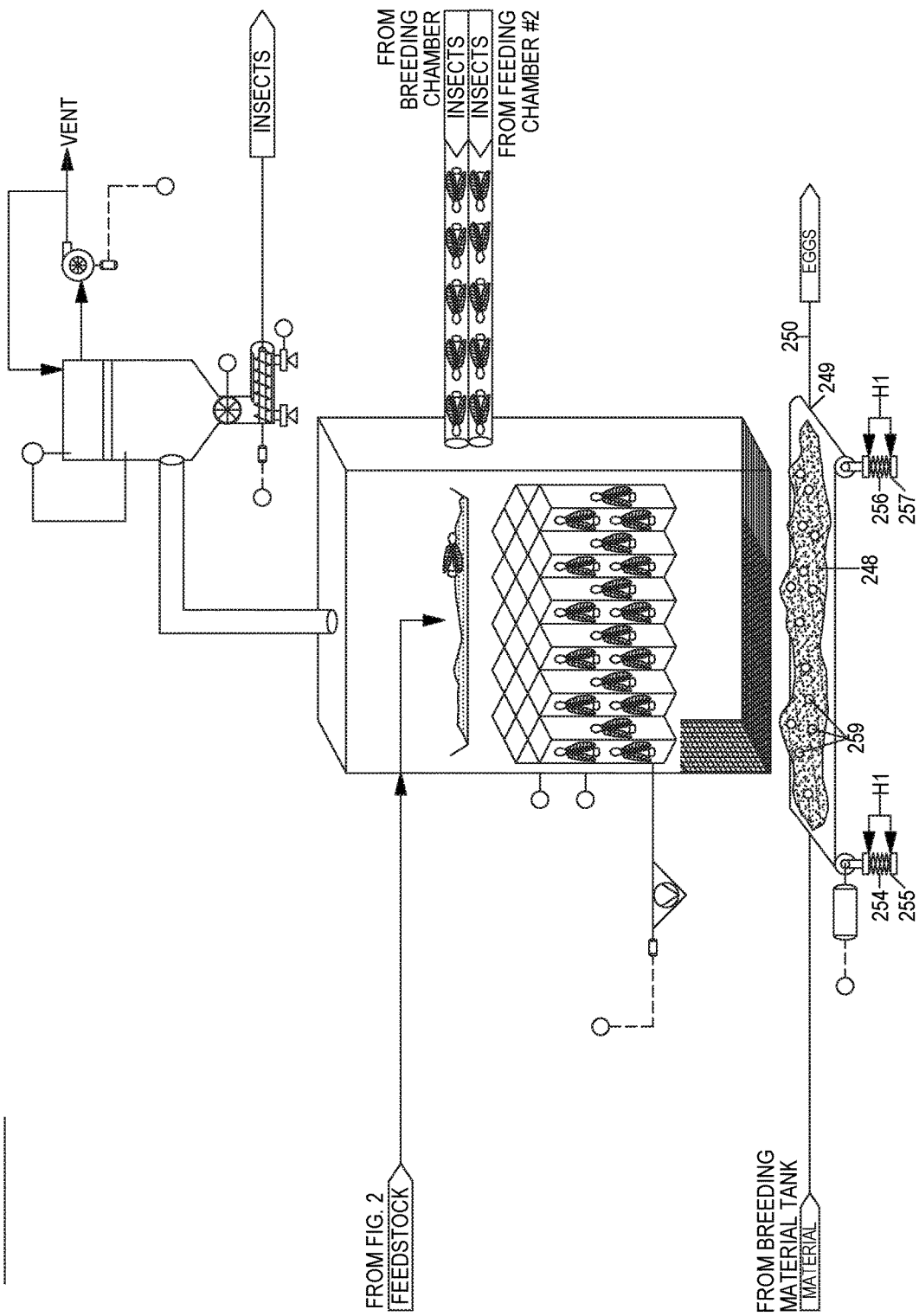

FIG. 6 elaborates upon the non-limiting embodiment of FIG. 3 but shows the insect feeding module (2000) operating in a third mode of operation wherein the egg transfer system (244) of the insect feeding module (2000) is at a first state in a first retracted height (H1) so as to discontinue insects (225) from laying eggs (259) within the provided breeding material (248).

Figure 7:
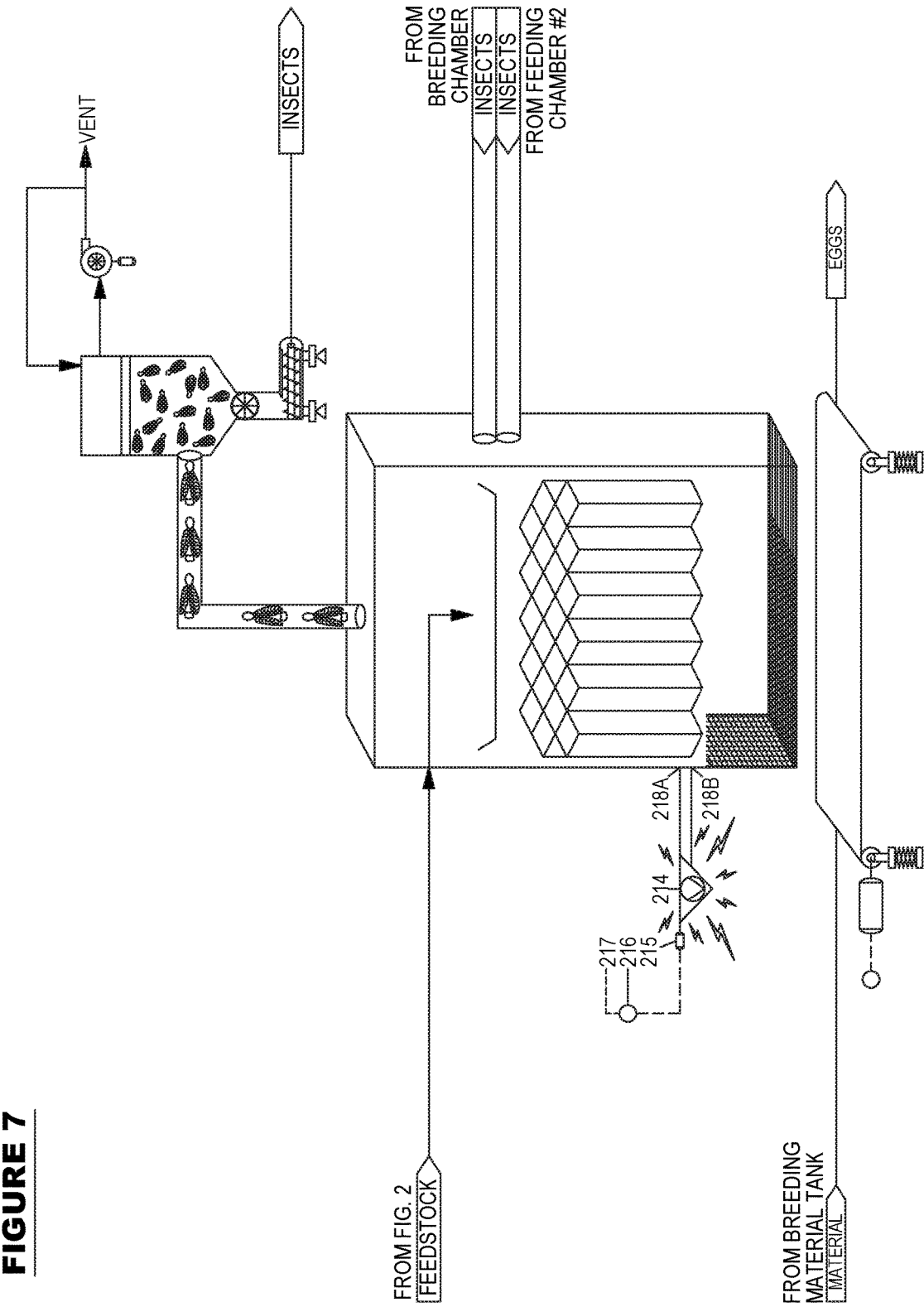

FIG. 7 elaborates upon the non-limiting embodiment of FIG. 3 but shows the insect feeding module (2000) and insect evacuation module (3000) operating in a fourth mode of operation wherein a vibration unit (214) is activated to permit the removal of insects (225) from the network (220) of cells (219) and wherein the insect evacuation module (3000) separates insects from gas while a vacuum is pulled on the insect feeding module (2000) via an insect evacuation fan (312)

Figure 8:
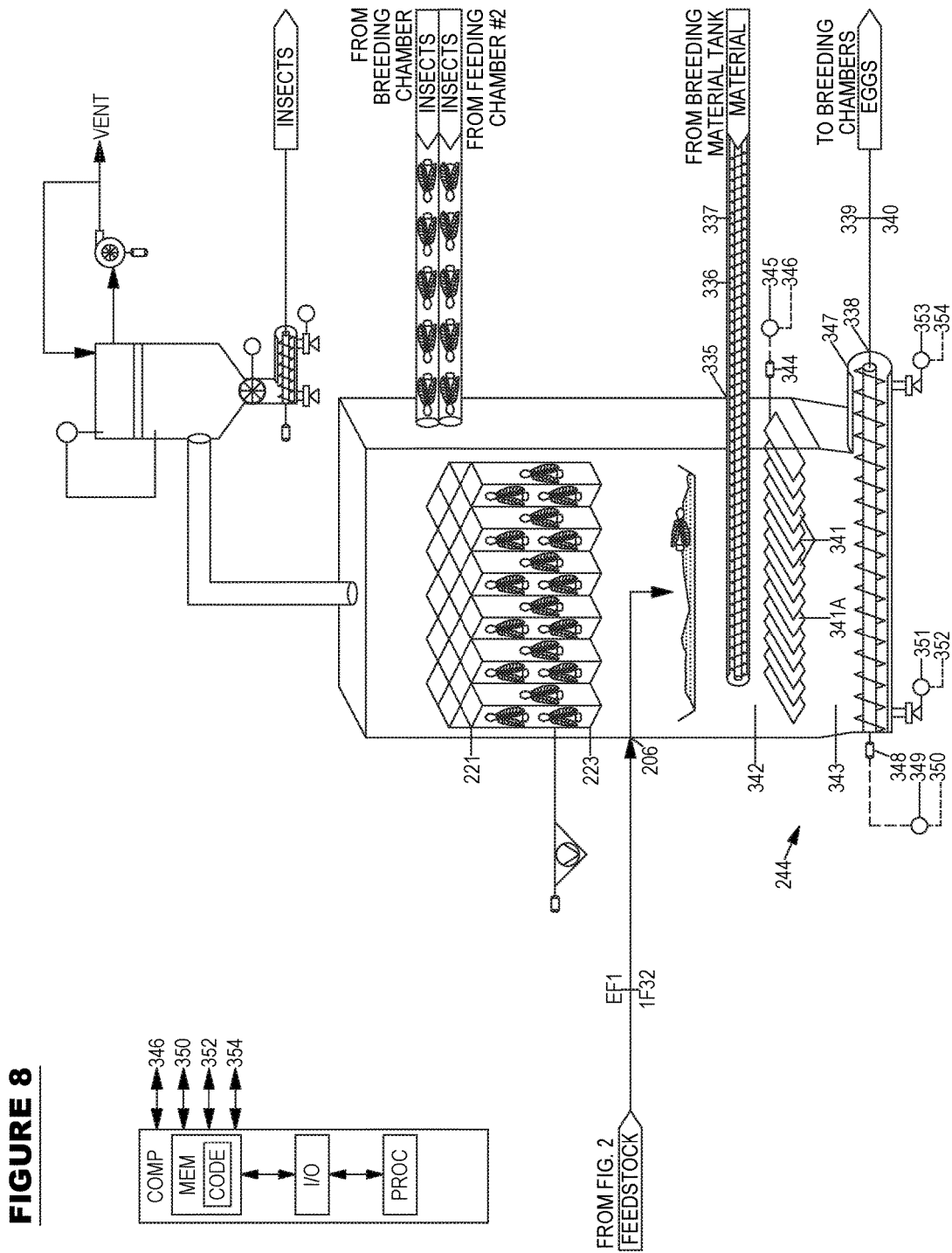

FIG. 8 shows a non-limiting embodiment of an insect feeding module (2000) integrated with an insect evacuation module (3000) operating in a first mode of operation wherein a plurality of slats (341) of an egg transfer system (244) of the insect feeding module (2000) are in first closed state (341A).

Figure 9:
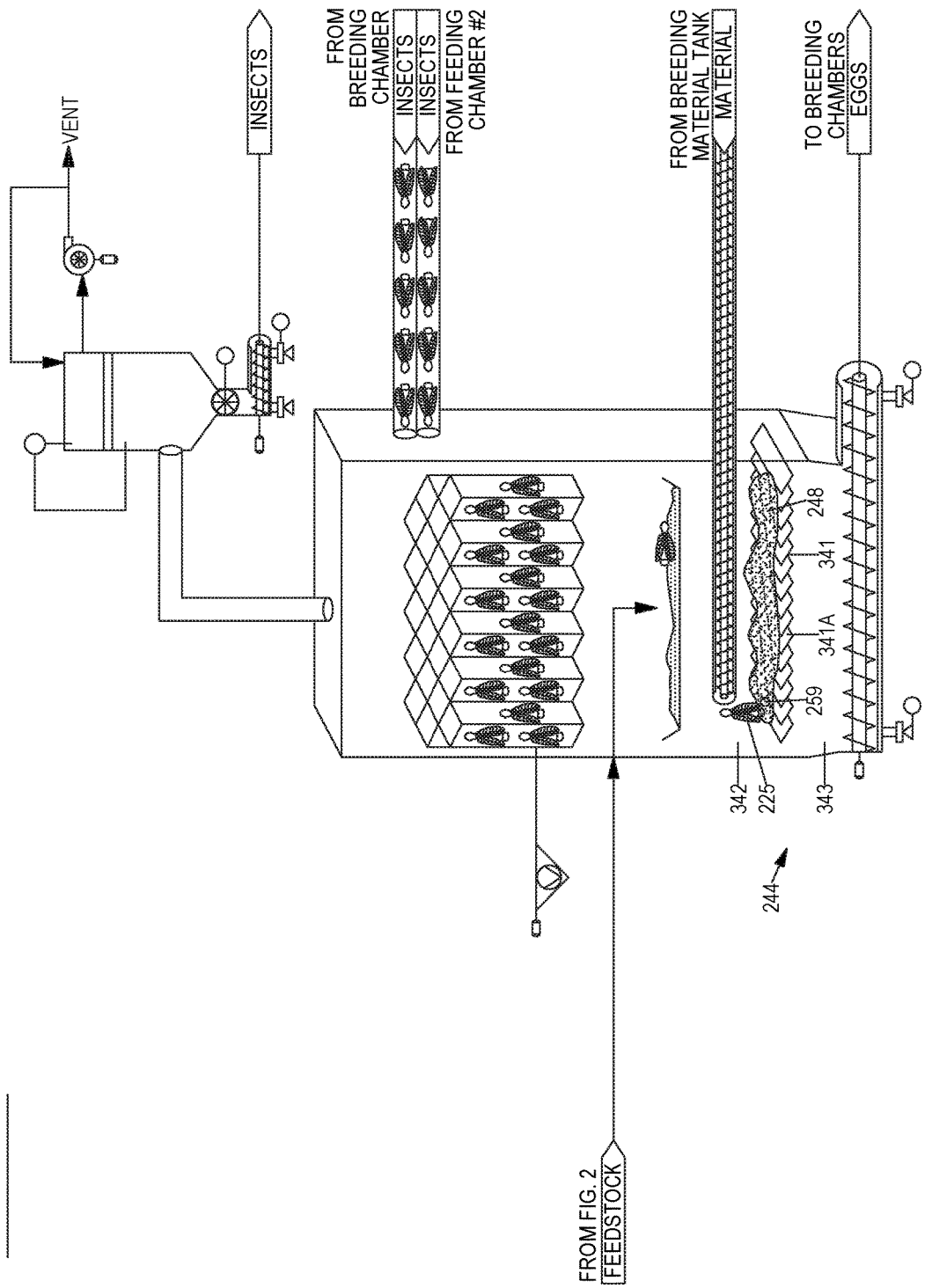

FIG. 9 elaborates upon the non-limiting embodiment of FIG. 8 and shows breeding material (248) resting upon the surface of the plurality of slats (341) of the egg transfer system (244) so as to permit insects (225) to lay eggs (259) within the breeding material (248).

Figure 10:
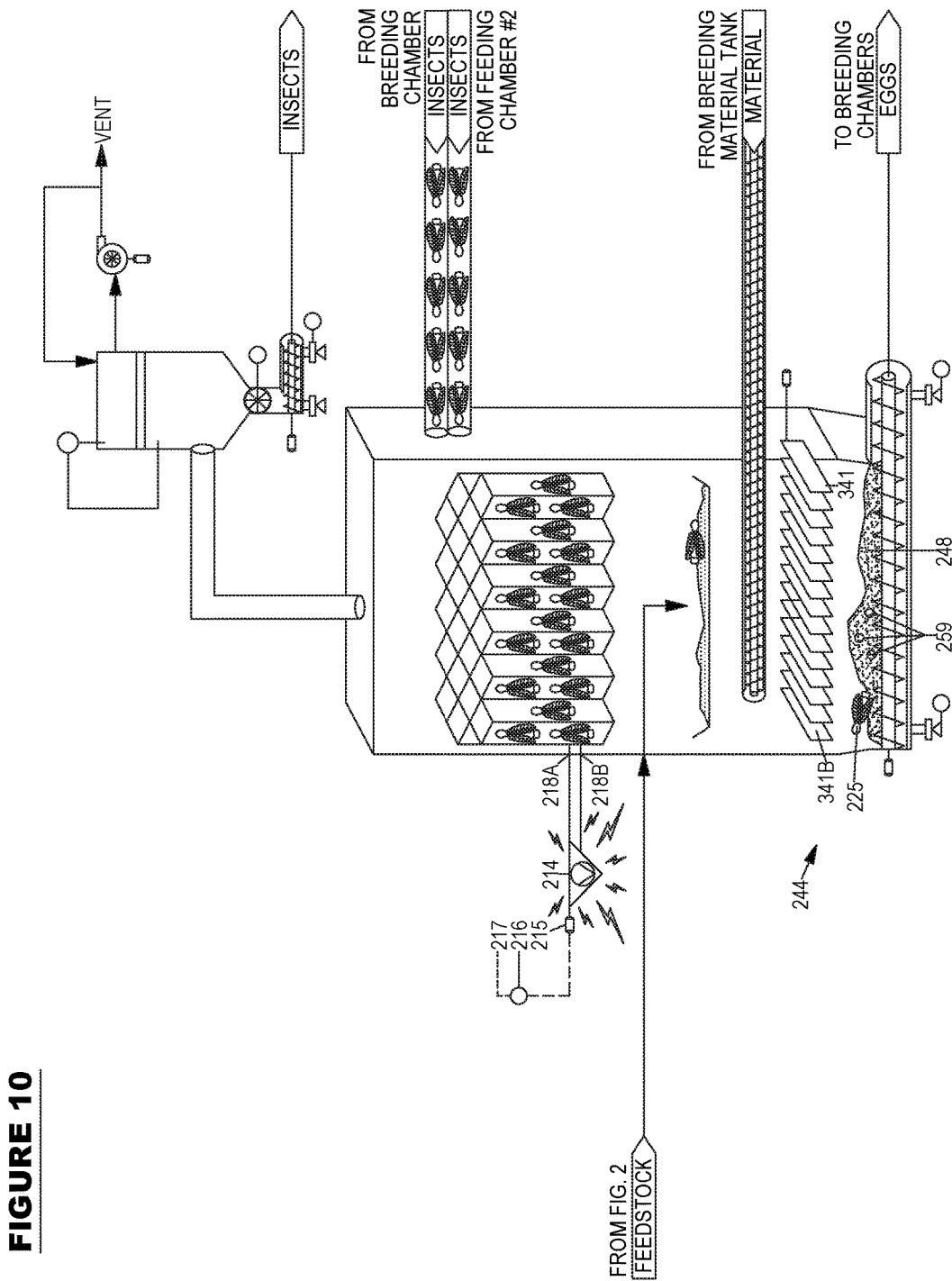

FIG. 10 elaborates upon the non-limiting embodiment FIG. 8 but shows the egg transfer system (244) in a second open state (341A) so as to permit egg-laden breeding material (248) to pass through the plurality of slats (341) while the vibration unit (214) is activated, some insects (225) may pass through the open slats (341) as well.

Figure 11:
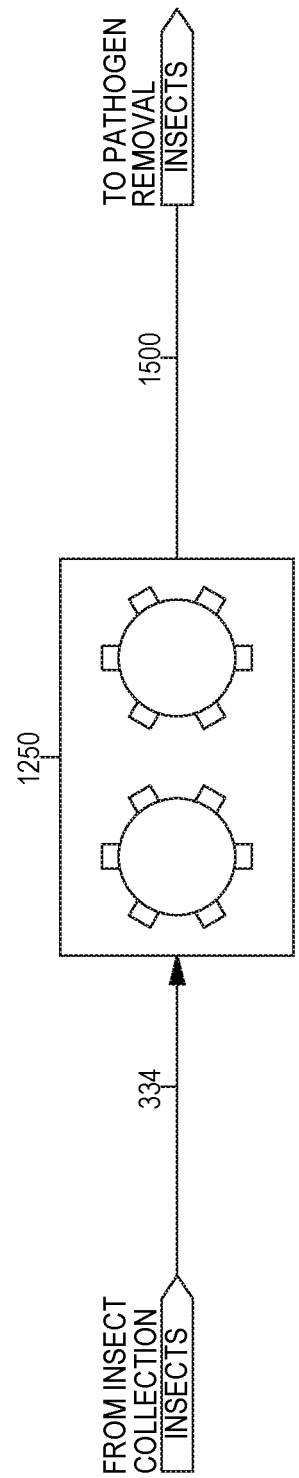

FIG. 11 shows a simplistic diagram illustrating an insect grinding module that is configured to grind at least a portion of the insects transferred from the insect evacuation module (3000).

Figure 12:
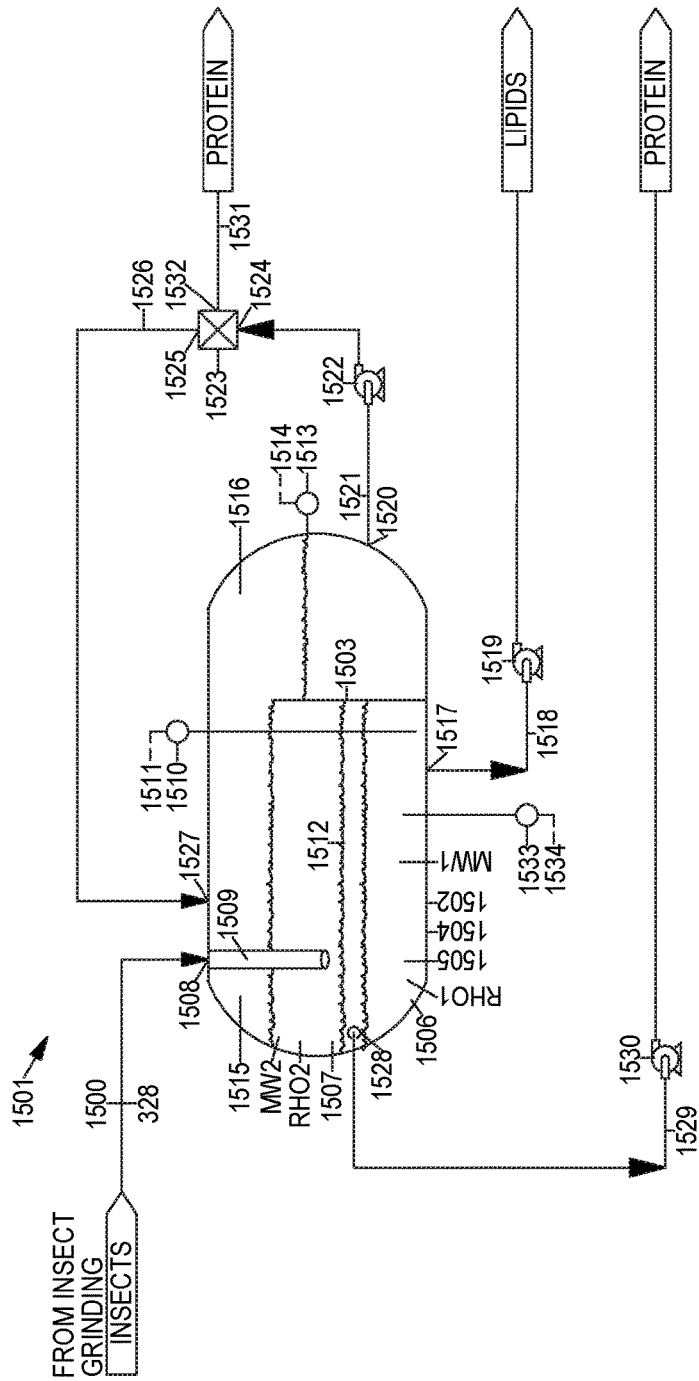

FIG. 12 shows a simplistic diagram illustrating a lipid extraction module that is configured to extract lipids from at least a portion of the insects transferred from the insect evacuation module (3000).

Figure 13:
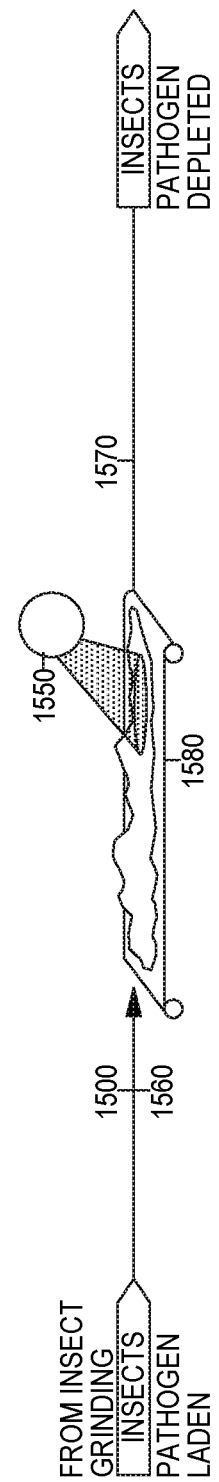

FIG. 13 shows a simplistic diagram illustrating a pathogen removal module that is configured to remove pathogens from at least a portion of the insects transferred from the insect evacuation module (3000).

FIG. 14A shows a simplistic diagram illustrating a multifunctional flour mixing module that is configured to generate a multifunctional alimentary flour from at least a portion of the insects transferred from the pathogen removal module and including the sequence steps or sub-modules including an insect distribution module (6A), fiber-starch distribution module (6B), binding agent distribution module (6C), density improving textural supplement distribution module (6D), moisture improving textural supplement distribution module (6E), multifunctional flour mixing module (6F).

Figure 14B:
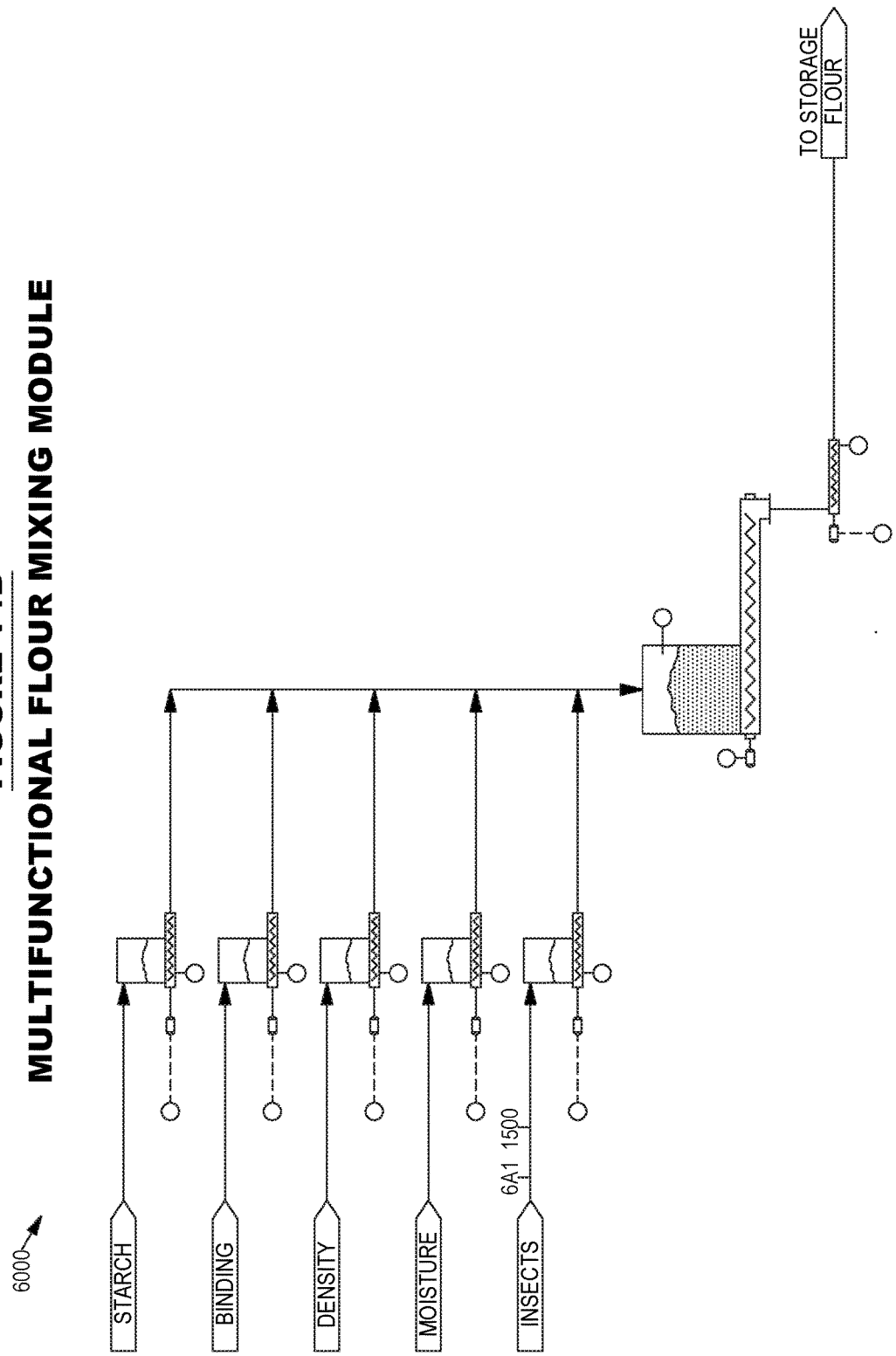

FIG. 14B shows a simplistic diagram illustrating a multifunctional flour mixing module that is configured to generate a multifunctional alimentary flour as described in FIG. 14A however instead from at least a portion of the insects transferred from the insect grinding module.

Figure 15:
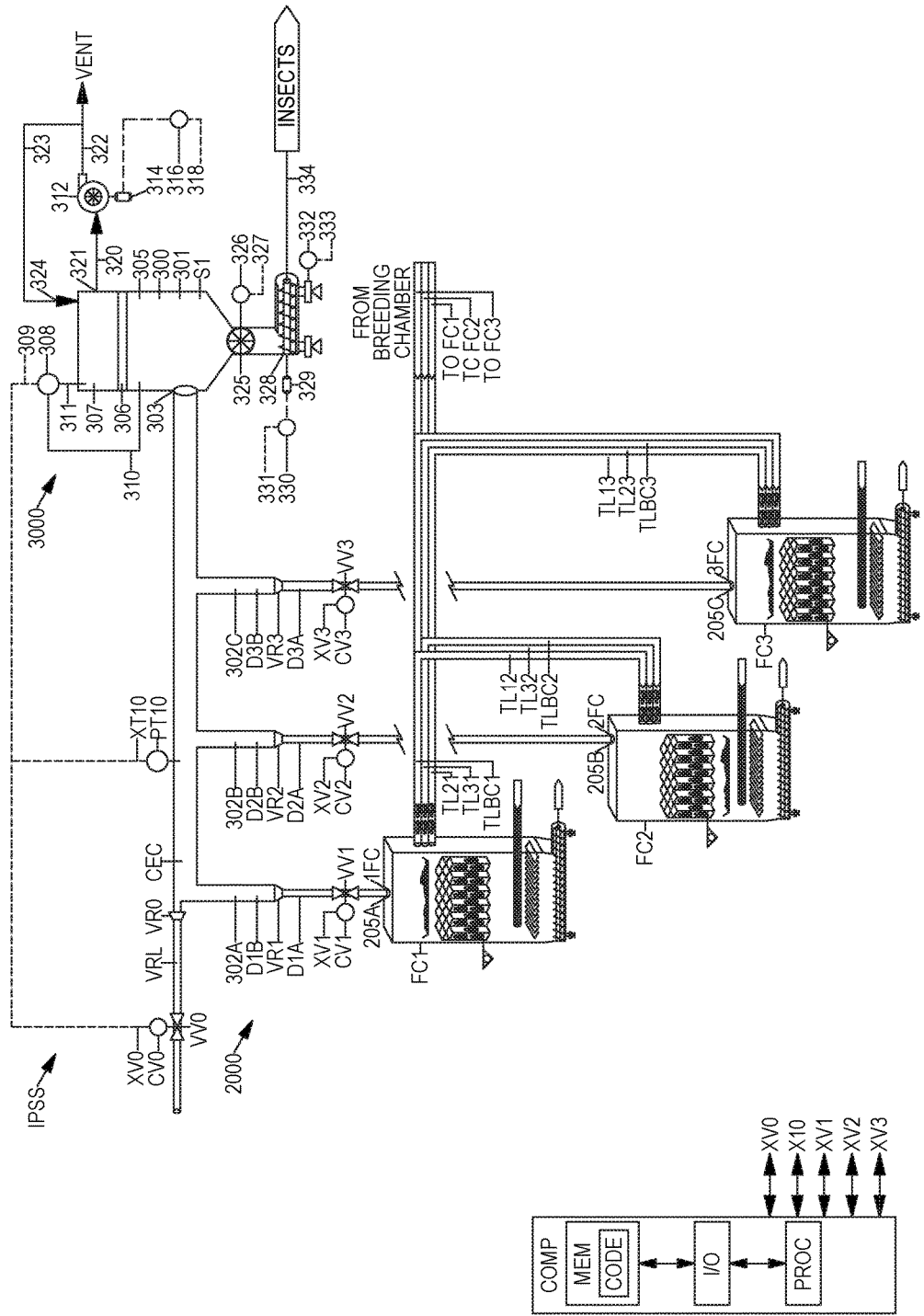

FIG. 15 shows a simplistic diagram illustrating a plurality of feeding chambers (FC1, FC2, FC3) of an insect feeding module (2000) integrated within one common separator (300) of an insect evacuation module (3000).

Figure 16:
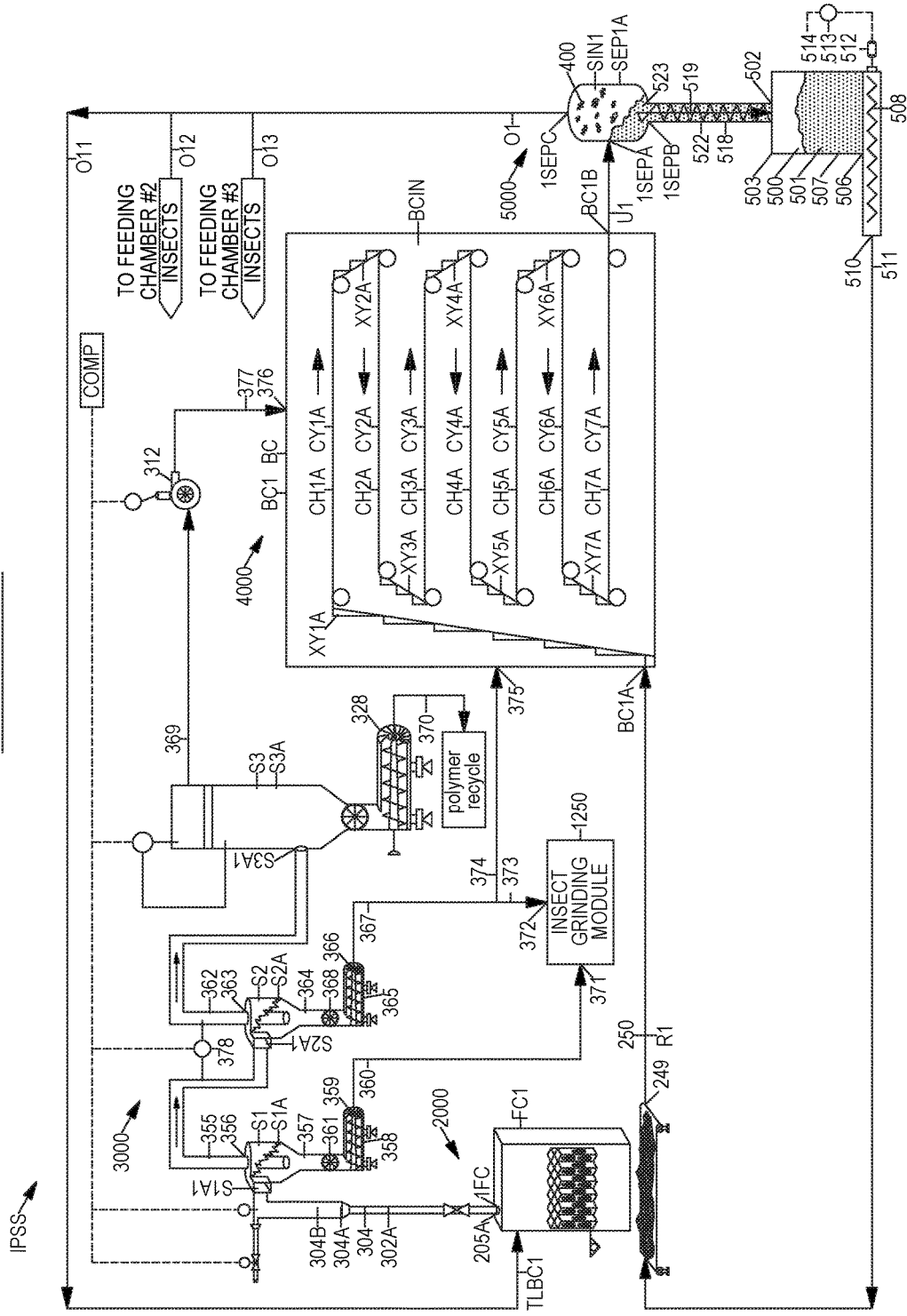

FIG. 16 shows a simplistic diagram illustrating a plurality of separators (S1, S2, S3) integrated with one common feeding chamber (FC1), and wherein the feeding chamber (FC1) and second separator (S2) are in fluid communication with one common breeding chamber (BC), and wherein the breeding chamber (BC) is in fluid communication with one common breeding material and insect separator (SEP1A), and wherein the breeding material and insect separator (SEP1A) is in fluid communication with at least one of a plurality of feeding chambers (FC1, FC2, FC3).

Figure 17:
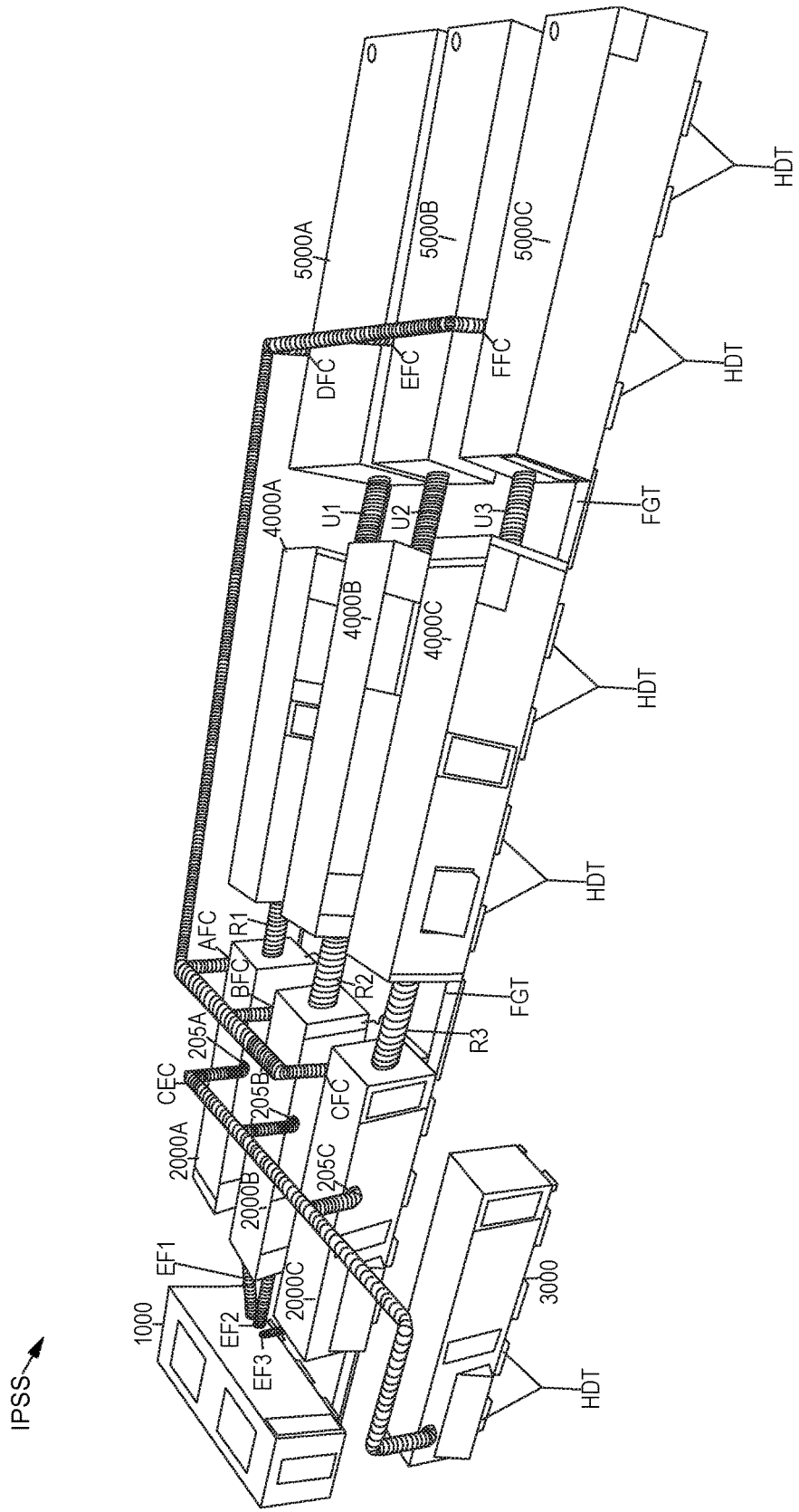

FIG. 17 shows a perspective view of one embodiment of a scalable portable modular Insect Production Superstructure System (IPSS) designed with: one enhanced feedstock mixing module (1000); three insect feeding modules (2000A, 2000B, 2000C); one insect evacuation module (3000); three insect breeding modules (4000A, 4000B, 4000C), and three insect separation modules (5000).

FIG. 18 shows a front view of one embodiment of an enhanced feedstock mixing module (1000) module including a feedstock distribution module (1A), mineral distribution module (1B), vitamin distribution module (1C), and a polymer distribution module (1D).

FIG. 19 shows a top view of one embodiment of an enhanced feedstock mixing module (1000) including a feedstock distribution module (1A), mineral distribution module (1B), vitamin distribution module (1C), and a polymer distribution module (1D).

Figure 20:
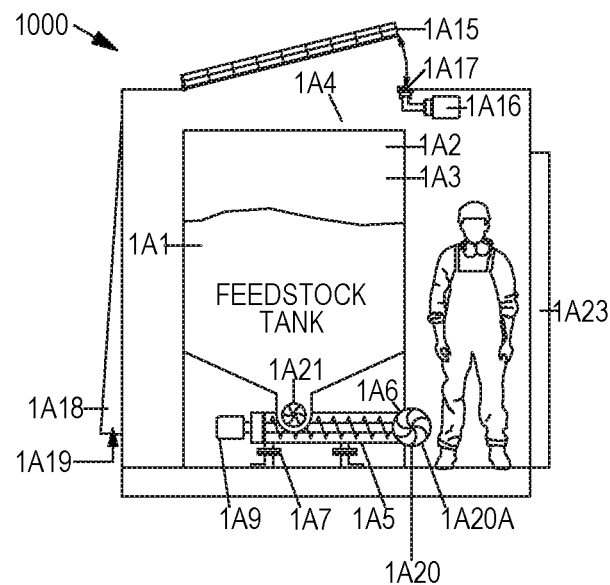

FIG. 20 shows a first side view of one embodiment of an enhanced feedstock mixing module (1000).

Figure 21:
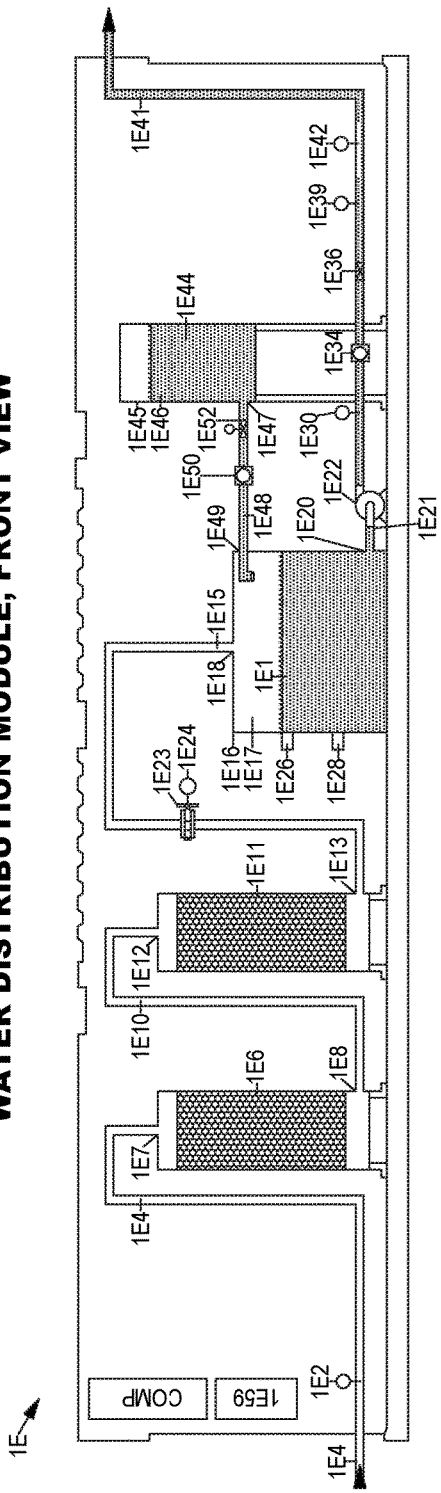

FIG. 21 shows a front view of one embodiment of a water distribution module (1E).

Figure 22:
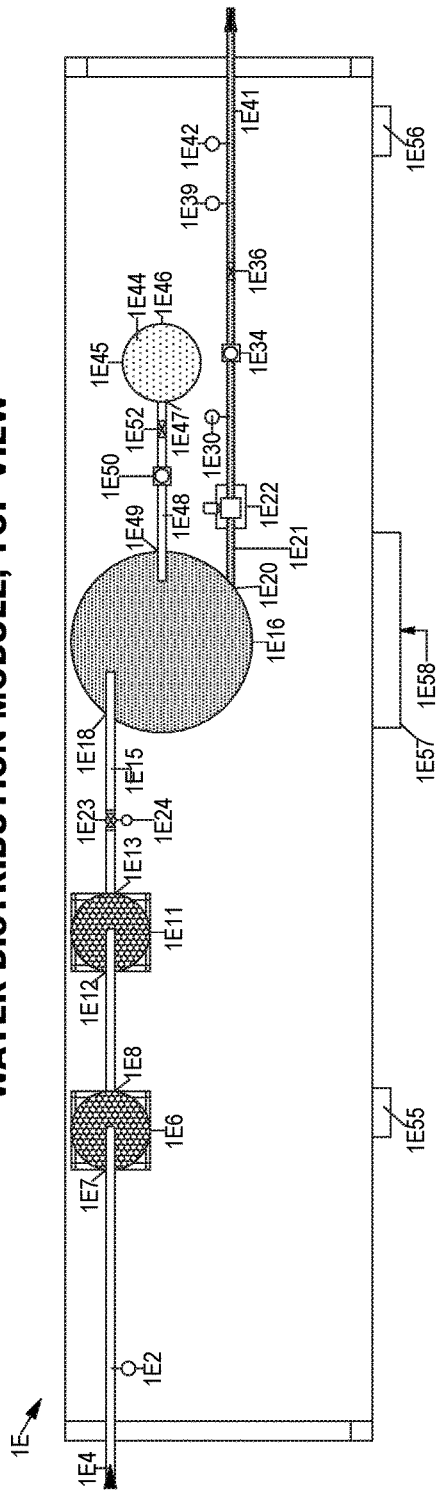

FIG. 22 shows a top view of one embodiment of a water distribution module (1E).

Figure 23:
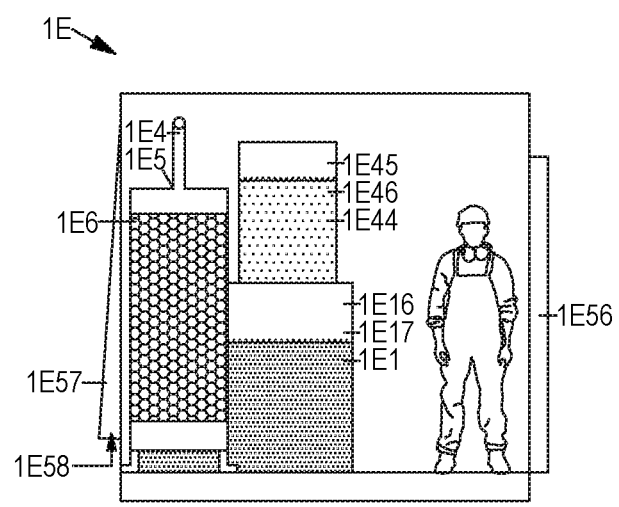

FIG. 23 shows a first side view of one embodiment of a water distribution module (1E).

Figure 24:
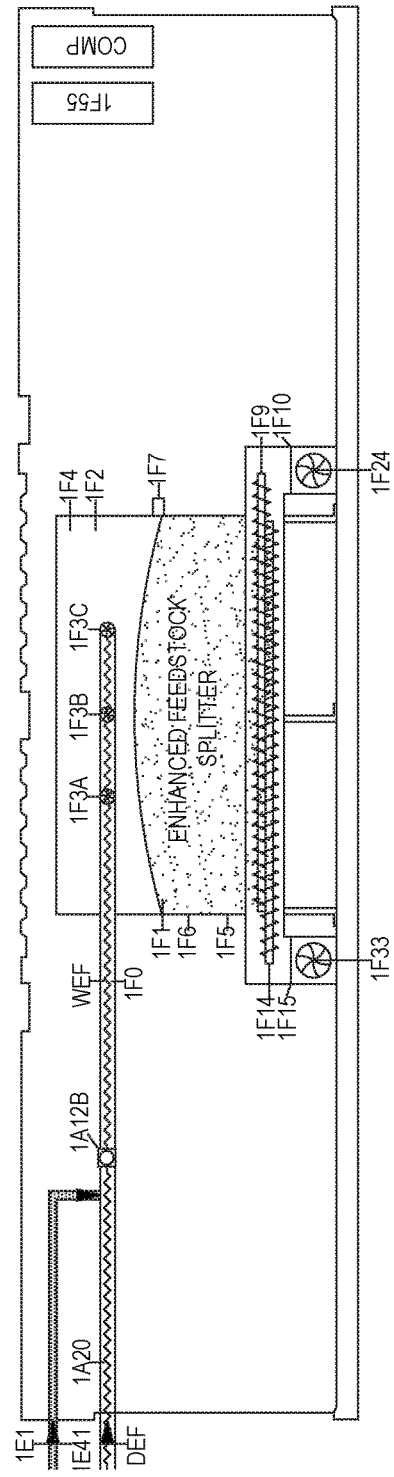

FIG. 24 shows a front view of one embodiment of an enhanced feedstock distribution module (1F).

Figure 25:
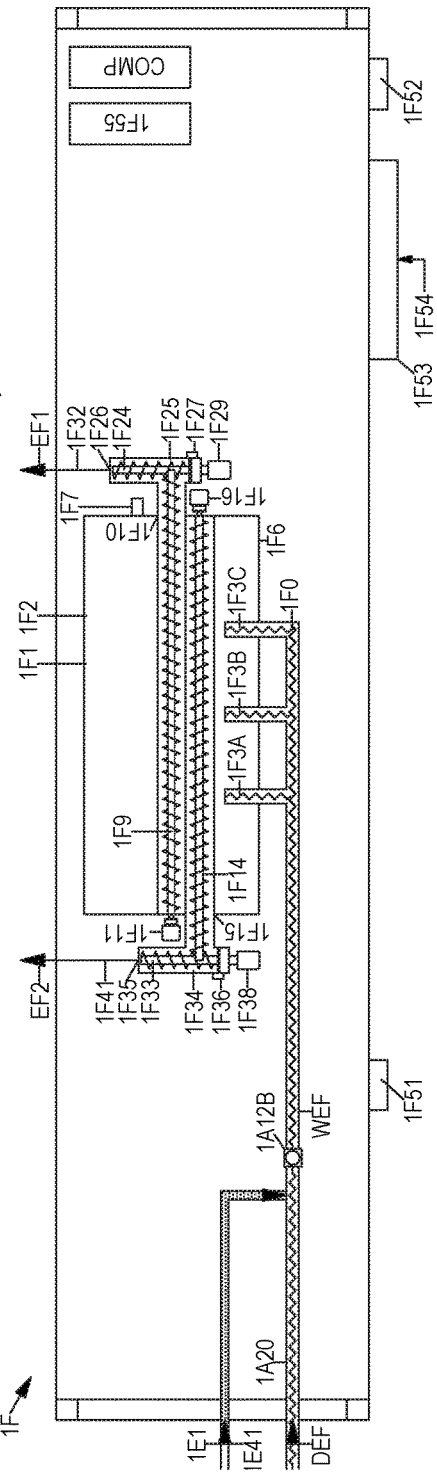

FIG. 25 shows a top view of one embodiment of an enhanced feedstock distribution module (1F).

Figure 26:
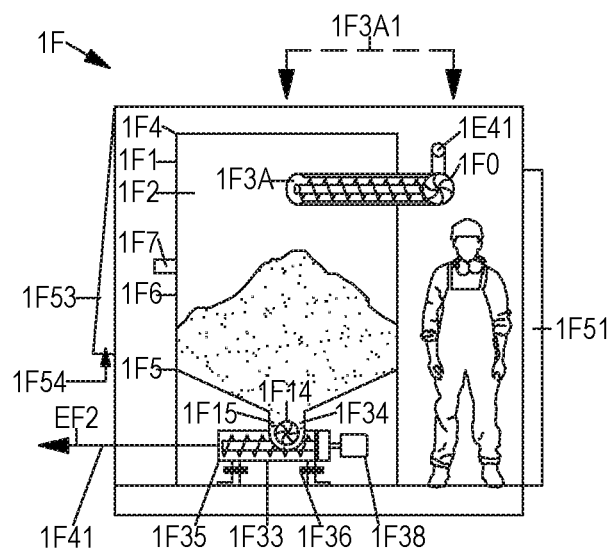

FIG. 26 shows a first side view of one embodiment of an enhanced feedstock distribution module (1F).

Figure 27:
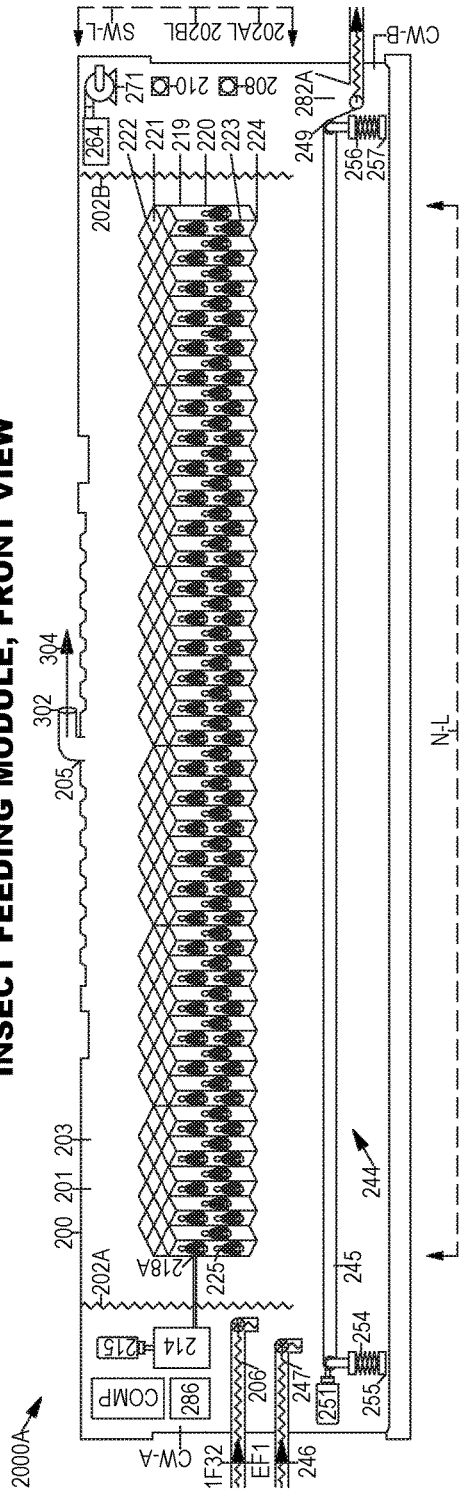

FIG. 27 shows a front view of one embodiment of an insect feeding module (2000, 2000A, 2000B, 2000C).

Figure 28:
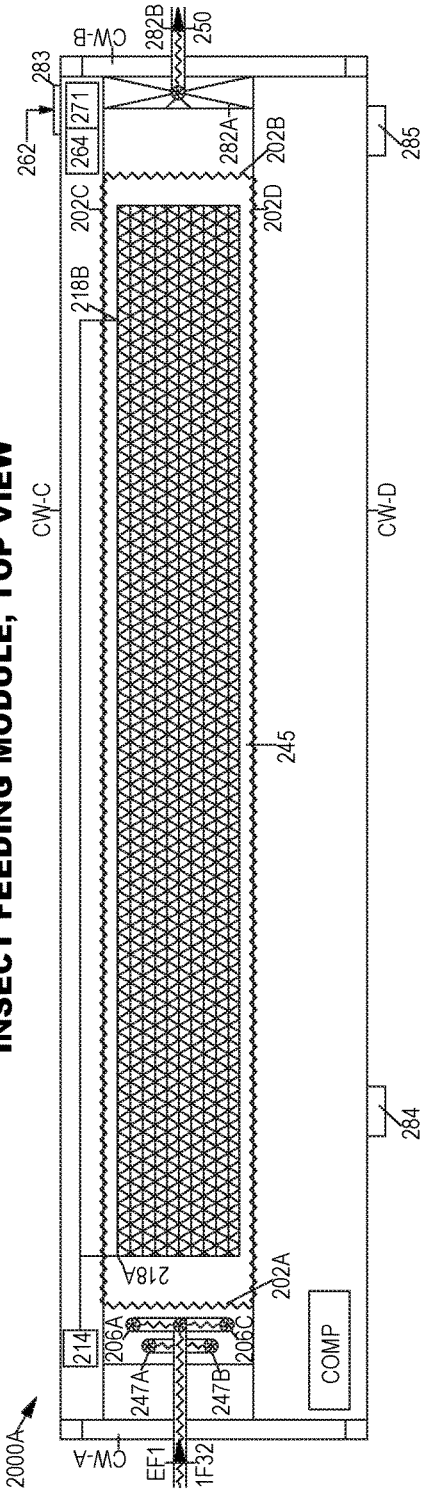

FIG. 28 shows a top view of one embodiment of an insect feeding module (2000, 2000A, 2000B, 2000C).

Figure 29:
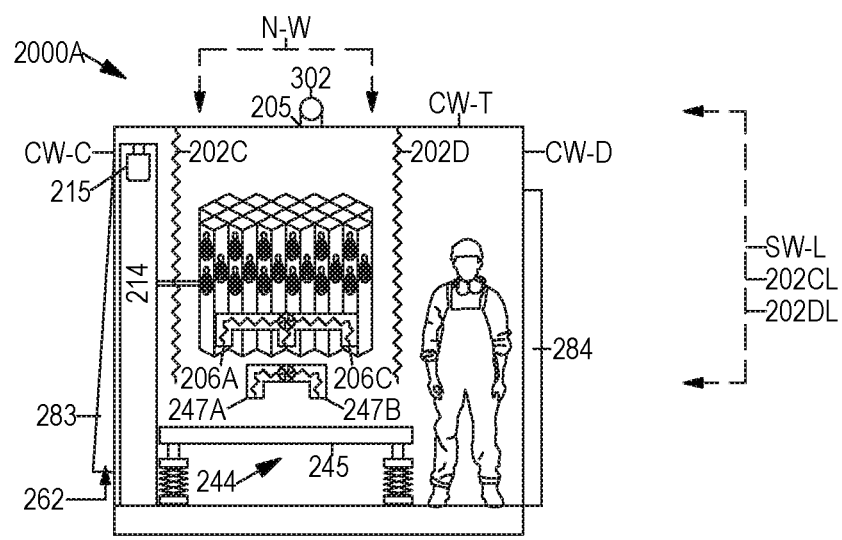

FIG. 29 shows a first side view of one embodiment of an insect feeding module (2000, 2000A, 2000B, 2000C).

Figure 30:
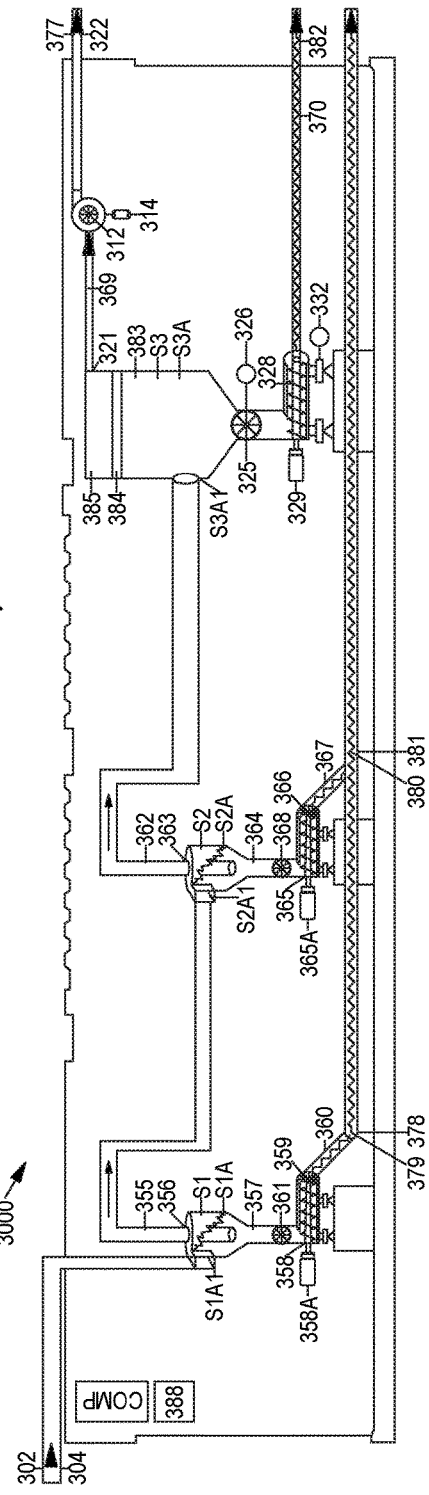

FIG. 30 shows a front view of one embodiment of an insect evacuation module (3000).

Figure 31:
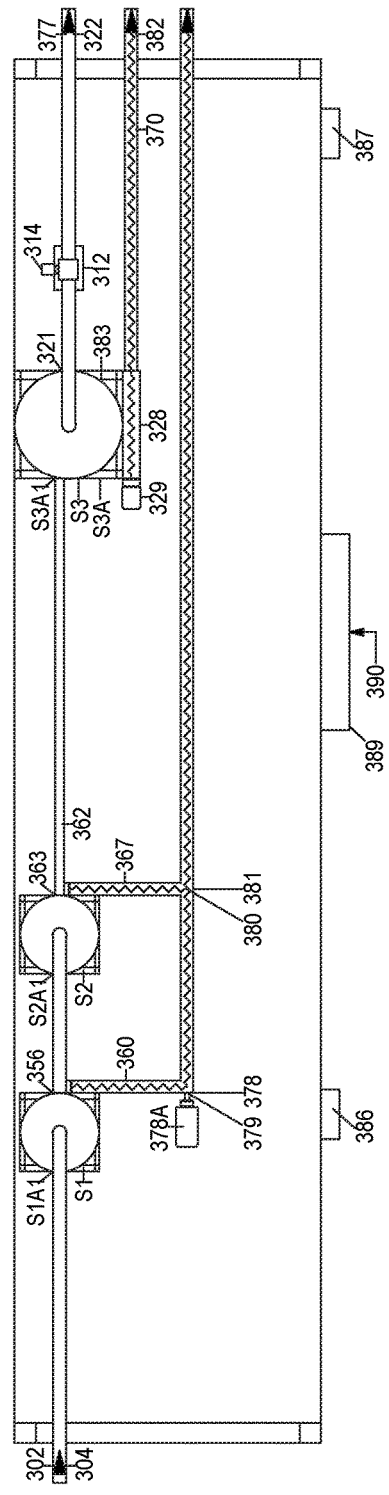

FIG. 31 shows a top view of one embodiment of an insect evacuation module (3000).

Figure 32:
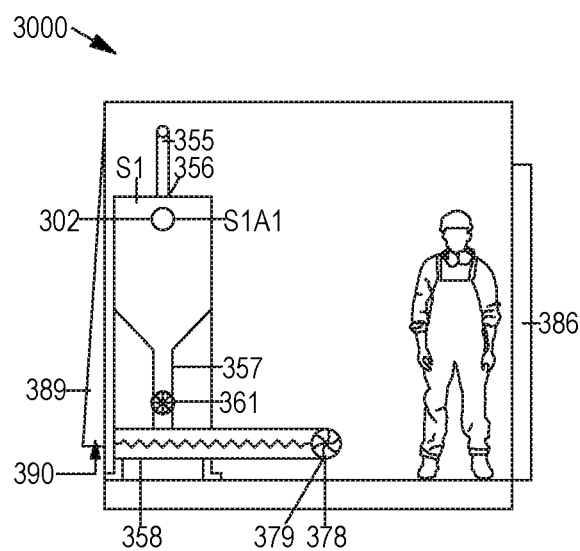

FIG. 32 shows a first side view of one embodiment of an insect evacuation module (3000).

Figure 33:
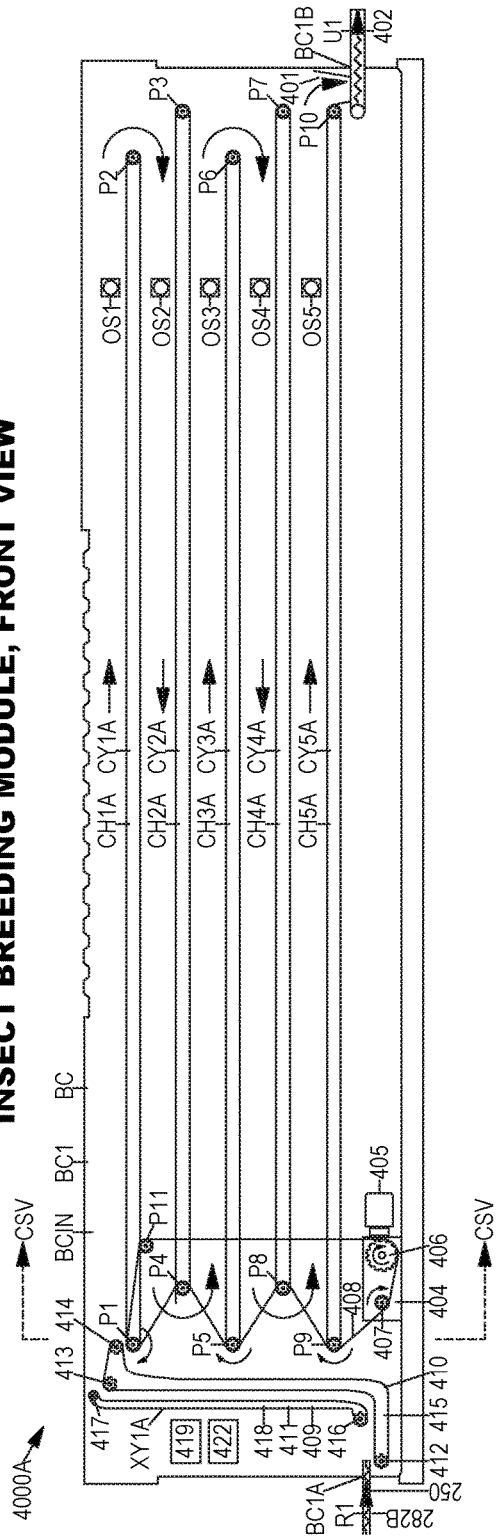

FIG. 33 shows a front view of one embodiment of an insect breeding module (4000, 4000A).

Figure 34:
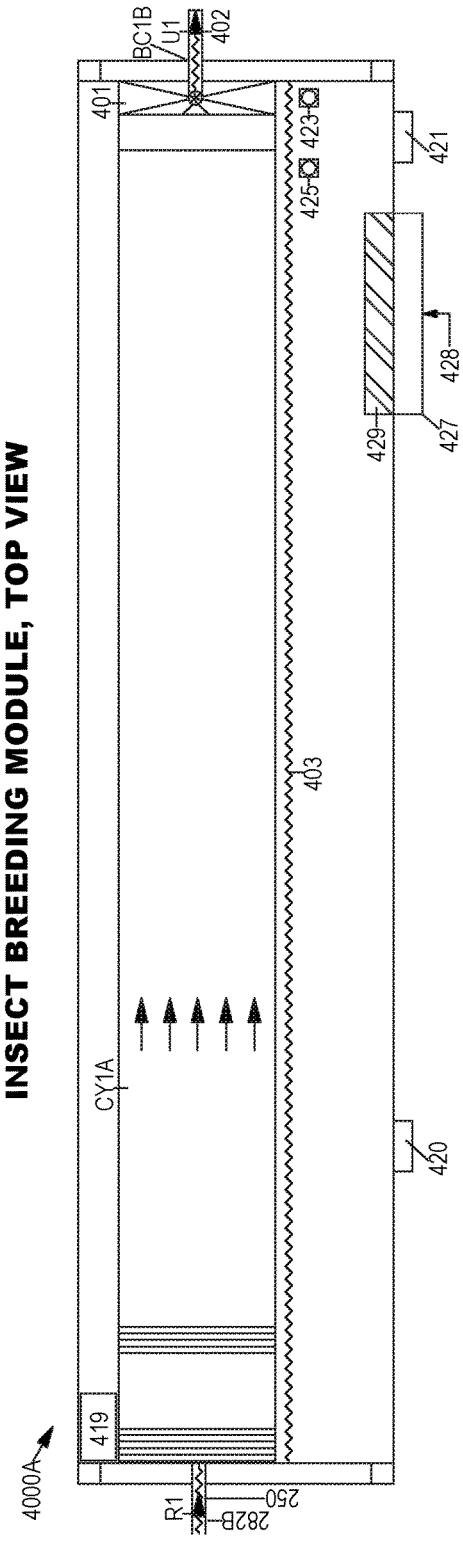

FIG. 34 shows a top view of one embodiment of an insect breeding module (4000, 4000A).

Figure 35:
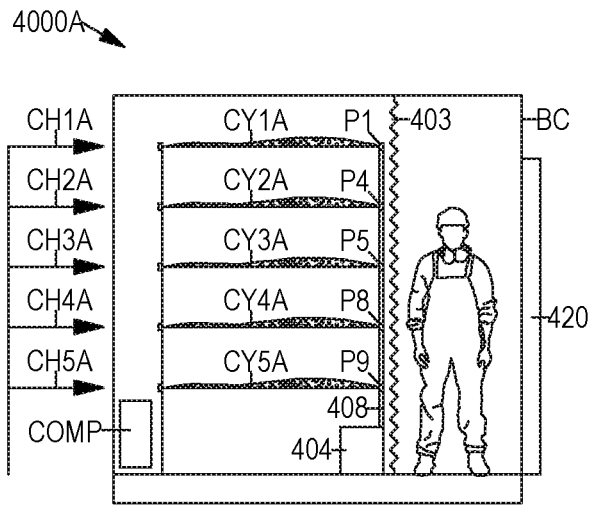

FIG. 35 shows a first side view of one embodiment of an insect breeding module (4000, 4000A) at a cutaway section of the conveyor side view (CSV).

Figure 36:
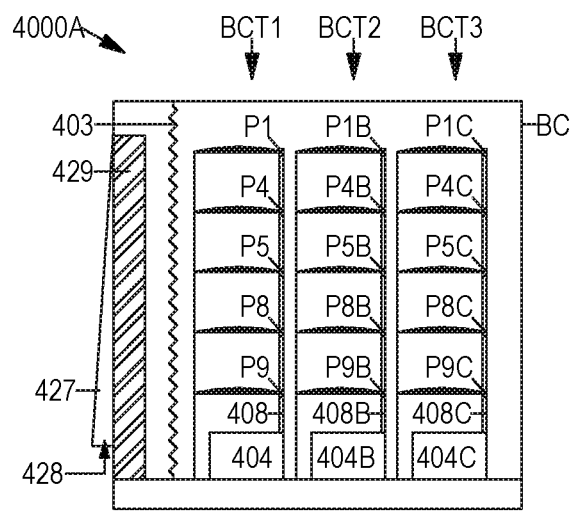

FIG. 36 shows a second side view of one embodiment of an insect breeding module (4000, 4000A) at a cutaway section of the conveyor side view (CSV).

Figure 37:
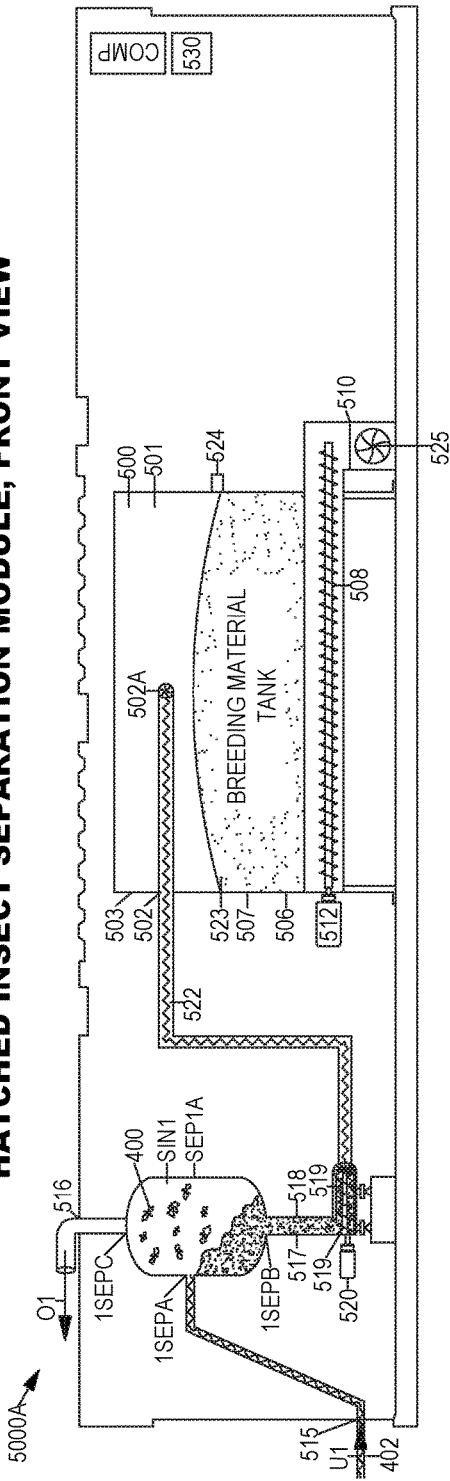

FIG. 37 shows a front view of one embodiment of a hatched insect separation module (5000, 5000A).

Figure 38:
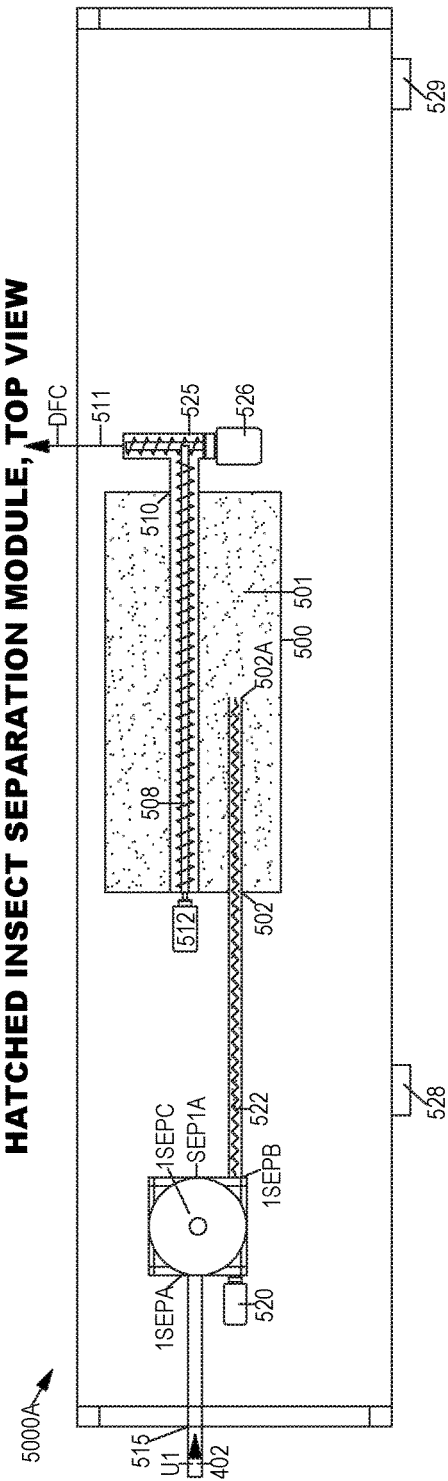

FIG. 38 shows a top view of one embodiment of a hatched insect separation module (5000, 5000A).

Figure 39:
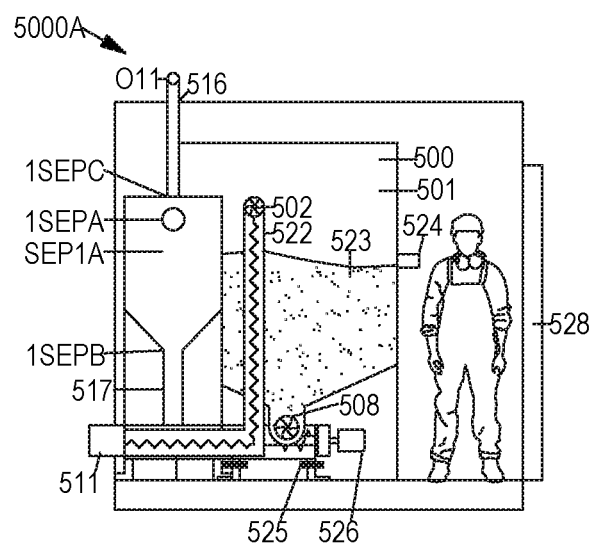

FIG. 39 shows a first side view of one embodiment of a hatched insect separation module (5000, 5000A).

FIG. 40 shows Table 1 with upper and lower ranges of feedstock mineral enhancers, feedstock vitamin enhancers, feedstock polymer enhancers, and other 'energy-Insect™' enhancers.

Figure 41A:
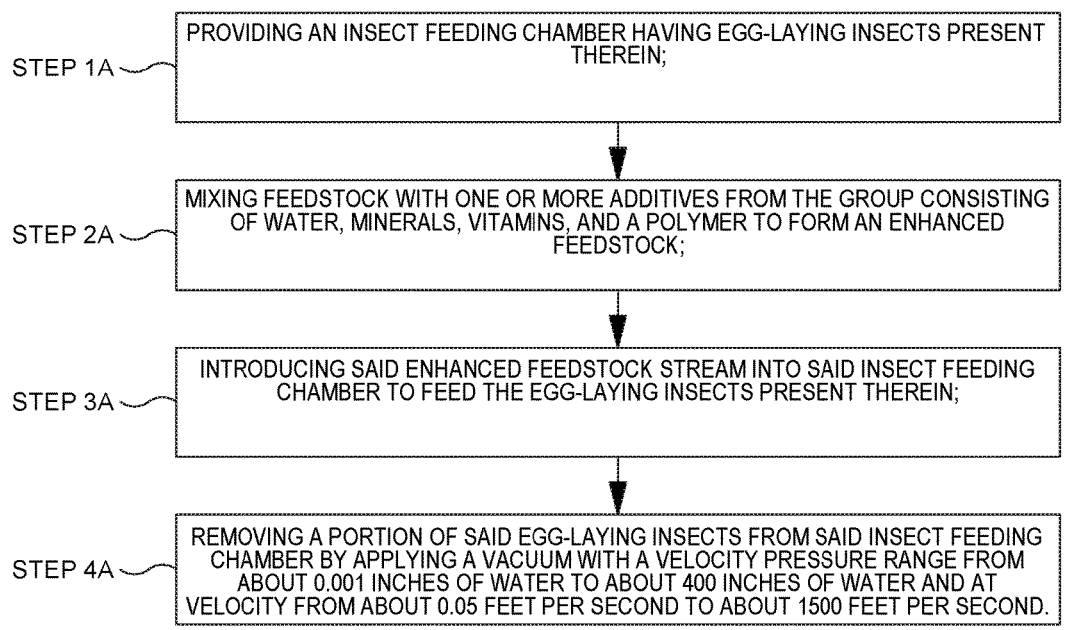

FIG. 41A shows one non-limiting embodiment of a method for raising Orthoptera order of insects.

FIG. 41B shows one non-limiting embodiment of another method for raising Orthoptera order of insects.

FIG. 42A shows one non-limiting embodiment of a method for raising Orthoptera order of insects.

FIG. 42B shows one non-limiting embodiment of another method for raising Orthoptera order of insects.

FIG. 43A shows one non-limiting embodiment of a method for raising Orthoptera order of insects.

FIG. 43B shows one non-limiting embodiment of another method for raising Orthoptera order of insects.

FIG. 44A shows one non-limiting embodiment of a method for raising Orthoptera order of insects.

FIG. 44B shows one non-limiting embodiment of another method for raising Orthoptera order of insects.

FIG. 45A shows one non-limiting embodiment of a method for raising Orthoptera order of insects to generate a multifunctional alimentary flour composition.

FIG. 45B shows one non-limiting embodiment of another method for raising Orthoptera order of insects to generate a multifunctional alimentary flour composition.

FIG. 46 shows one non-limiting embodiment of another method for raising Orthoptera order of insects to generate a multifunctional alimentary flour composition.

FIG. 47 shows one non-limiting embodiment of a method for raising Orthoptera order of insects for the separation of lipids contained within said insects.

FIG. 1A

FIG. 1A shows a simplistic block flow diagram of one embodiment of an Insect Production Superstructure System (IPSS) including the sequence steps of feedstock mixing (step A), feedstock splitting (step B), insect feeding (step C1, C2), insect breeding (step D), insect collection (step E), and insect grinding (step F).

FIG. 1A shows a plurality of sequence steps of an Insect Production Superstructure System (IPSS) including, feedstock mixing (step A), feedstock splitting (step B), insect feeding chamber #1 (step C1), insect feeding chamber #2 (step C2), insect breeding (step D), insect collection (step E), and insect grinding (step F).

Step A involves feedstock mixing where feedstock may be mixed with one or more additives from the group consisting of water, minerals, vitamins, and polymer to form an enhanced feedstock. Additionally, other enhancers may be added to the feedstock such as niacin, taurine, glucuronic acid, malic acid, N-acetyl L tyrosine, L-phenylalanine, caffeine, citicoline, or insect growth hormones. Table 1 on FIG.

40 lists the types of additives and enhancers that may be mixed with a feedstock to generate an enhanced feedstock.

Generally, a feedstock may be characterized as agriculture residue, alcohol production coproducts, animal waste, biowaste, compost, crop residues, energy crops, fermentation waste, meat, insects, fermentative process wastes, food processing residues, food waste, garbage, industrial waste, livestock waste, municipal solid waste, plant matter, poultry wastes, rice straw, sewage, spent grain, spent microorganisms, urban waste, vegetative material, or wood waste.

Mixing of feedstock with additives or enhancers is discussed below in detail. Exact proportions of feedstock, additives, and enhancers may be precisely combined to form an enhanced feedstock that is suitable to grow insects in a manner that maximizes productivity, minimizes mortality, and maximizes animal welfare. It has been my realization that the enhanced feedstock mixtures, weigh ratios, proportions, ranges cited in Table 1 of FIG. 40 are those that maximize insect production in a minimal amount of space.

It also has been my realization that the enhancers listed herein are those, when fed to insects, may then subsequently fed to humans as energy-Insects™, which are a specialized kind of edible insect that contains a dose of the stimulant caffeine, vitamins, and other functional ingredients. It has also been my realization that insects truly enjoy eating my inventive enhanced feedstock blend and it increases their quality of life. Although there is no evidence and no way of truly telling that insects have the cognitive ability to enjoy eating my proprietary enhanced feedstock blend, I certainly give them the benefit of the doubt.

It has also been my realization that mixing water with the feedstock profoundly benefits insects since it elevates their well-being by making it impossible for them not to fear from expiration from respiratory impairment from being drowned in or under a liquid. It is the totality of the features of the present application that provide the maximum benefit to society.

An enhanced feedstock transfer line (002) is discharged from feedstock mixing (step A) where it enters the feedstock splitting (step B). Step B feedstock splitting involves dividing the enhanced feedstock up into a plurality of enhanced feedstock steams. In embodiments, it may be advantageous to have a plurality of insect feeding chambers and only one feedstock mixing sequence step. This minimizes the capital intensity of the Insect Production Superstructure System (IPSS) to thus in turn permits a more lucrative return on investment (ROI). In some instances, Step B may not be required since only one feeding chamber is desired.

A first enhanced feedstock transfer line (004) and a second enhanced feedstock transfer line (006) are discharged from feedstock splitting (Step B) and are routed to insect feeding chamber #1 (step C1) and insect feeding chamber #2 (step C2). FIG. 1A discloses a plurality of feeding chamber steps (C1 and C2). Two feeding chambers are shown in FIG. 1A, however it is to be noted that only one may be utilized, or three (as depicted in FIG. 17), or more may be utilized as seen fit.

Although two feeding chambers are shown in FIG. 1A, it is to be noted that the egg-laying insects present therein may freely travel from one feeding chamber to another. This is evidenced by feeding chamber transfer line (008) which connects the insect feeding chamber #1 (step C1) with insect feeding chamber #2 (step C2). The plurality of feeding chambers and a passageways therebetween encourage egg-laying insects therein to express normal behavior by enabling mobility and relocation to a more suitable living environment. An insect may decide to up and relocate for any reason it chooses or no reason at all. In the event that one breeding chamber lacks sufficient amounts of enhanced feedstock, or is over-crowded, or contains diseased or cannibalistic insects, the insects may relocate to another feeding chamber to alleviate their discomfort, pain, injury, disease, and fear and distress.

Herein is disclosed an Insect Production Superstructure System (IPSS) that permits insects to have mobility and the opportunity to choose between different possible courses of action. Herein are disclosed advancements and better solutions that meet new requirements, unarticulated needs, or existing market needs in maximizing insect welfare, maximizing insect output on a minimal physical outlay, and benefit of large groups of people a high-value animal protein.

FIG. 1A shows a first egg-laden breeding material transfer line (020) and a second egg-laden breeding material transfer line (021) being mixed into a combined egg-laden breeding material transfer line (022) which is then in turn provided to insect breeding (step D).

Insect eggs are extracted from the plurality of breeding chambers and are provided to a breeding chamber where the eggs are incubated and hatched. Hatched insects are then provided to the plurality of insect feeding chambers (step C1 and C2) via a first feeding chamber hatched insect transfer line (024) and a second feeding chamber hatched insect transfer line (026), respectively. Thus herein is disclosed a method to: (i) remove at least a portion of eggs laid by the egg-laying insects within the feeding chambers; (ii) incubate at least a portion of the removed eggs in a breeding chamber; (iii) hatch at least a portion of incubated eggs; and, (iv) introduce a portion of hatched insects back into the insect feeding chamber.

Generally, the innovative methods of the Insect Production Superstructure System (IPSS) is more generally suited for insects of the Orthoptera order of insects including grasshoppers, crickets, cave crickets, Jerusalem crickets, katydids, weta, lubber, acrida, and locusts. However, other methods and systems described herein may also be applied towards other orders of insects, such as cicadas, or even minilivestock if desired.

Both the insect feeding chamber #1 (step C1) and insect feeding chamber #2 (step C2) are in fluid communication with insect collection (step E). The insect feeding chamber #1 (step C1) is in fluid communication with insect collection (step E) via a first feeding chamber insect transfer line (010). The insect feeding chamber #2 (step C2) is in fluid communication with insect collection (step E) via a second feeding chamber insect transfer line (012).

Insects may be collected from the insect feeding chambers in a number of ways. Some non-limiting embodiments of the present disclosure suggest removing the insects by vibrating the egg-laying insects from the feeding chamber. Some non-limiting embodiments of the present disclosure suggest removing the insects by conveying the egg-laying insects from the feeding chamber. Some non-limiting embodiments of the present disclosure suggest vacuuming the insects from the feeding chamber.

It is to be noted that all of the embodiments disclosed herein are non-limiting and as long as the insects are in fact removed from an insect feeding chamber by any conceivable means or method, the bounds of this application are deemed to have been infringed. Thus it should be apparent, however, to those skilled in the art that many more modifications besides those already described are possible without departing from the inventive concepts herein related to removing insects from the feeding chamber. The inventive subject matter pertaining to removing insects from the feeding chambers, therefore, is not to be restricted to vibrating, conveying, vacuuming insects from the feeding chamber but instead extend to any possible means for achieving the end of removing insects from out of the interior of the feeding chamber.

In embodiments, the insect collection (step E) is in fluid communication with insect grinding (step F) via a combined collected insect transfer line (014). The insect grinding (step F) is configured to output ground insects via a ground insect transfer line (016).

FIG. 1B

FIG. 1B elaborates upon the non-limiting embodiment of FIG. 1 further including the sequence steps of pathogen removal (step G) and multifunctional flour mixing (step H).

FIG. 1B shows a pathogen removal (step G) placed upstream of a multifunctional flour mixing (step H) step. In embodiments, the pathogen removal (step G) is configured to accept collected insects provided from the insect collection (step E) or insect grinding (step F). In embodiments, the pathogen removal (step G) is configured to accept collected insects provided from the insect collection (step E). In embodiments, the pathogen removal (step G) is configured to accept collected insects provided from the insect grinding (step F) as seen in FIG. 13 as accepting ground separated insects (1500). However, it is to be noted that grinding need not take place in order for pathogen to be removed from collected insects. As seen in the non-limiting embodiment of FIG. 1B, pathogen removal (step G) only places after insect collection (step E) and after insect grinding (step F). However, it is not necessary that grinding takes place in between insect collection (step E) and pathogen removal (step G).

Pathogen removal (step G) is optional. Until we know for sure that a death by being grinded up is not less painful than being microwaved, we will give the insects the benefit of the doubt and concede to the notion that sudden, instantaneous death will lead to less stress and suffering as opposed to being microwaved over up to about 500 seconds. Thus, it is the essence of this disclosure to intend that a person of ordinary skill in the art be on notice of my intention to entertain all possibilities to grinding insects, microwaving them, or suffocating them to death. Until there is peer-reviewed evidence to suggest that grinding is least deleterious on the welfare of an insect, Step F will be before Step G.

Pathogen Removal (Step G)

The pathogen removal (step G) involves utilization of a pathogen removal unit to convert a stream of pathogen-laden insects into a stream of pathogen-depleted insects (1570). The pathogen removal (step G) removes pathogens from pathogen-laden insects to form pathogen depleted insects which has a reduced amount of pathogens relative to the pathogen-laden insects.

In embodiments, pathogens are comprised of one or more from the group consisting of acute respiratory syndrome coronavirus, influenza A viruses, H5N1, H7N7, avian influenza, foot and mouth disease, bovine spongiform encephalopathy, Q-fever, cutaneous zoonotic leishmaniasis, ebola, monkeypox, Rift Valley fever, Crimea Congo haemorrhagic fever, encephalopathy, West Nile fever, paramyxoviruses, viruses, bacteria, fungus, prions, and parasites. In embodiments, some of the aforesaid pathogens may be present in the insects that grow within the feeding chamber. It is possible that the water added to the enhanced feedstock contains pathogens as listed above which the insect's carry-on through to the humans and animals during consumption. Thus it is of paramount importance to mitigate the possible threats to society that are associated with permitting pathogen-laden water to pass on to humans or animals via the pathogen-laden insects.

In embodiments, pathogens are removed from the insects by the application of heat. In embodiments, pathogens are removed by heating insects to a temperature range between about 110 degrees Fahrenheit to about 550 degrees Fahrenheit. In embodiments, pathogens are removed by heating insects to a temperature range between about 120 degrees Fahrenheit to about 170 degrees Fahrenheit. In embodiments, pathogens are removed by heating said insects to a temperature range between about 171 degrees Fahrenheit to about 250 degrees Fahrenheit. In embodiments, pathogens are removed by heating insects to a temperature range between about 350 degrees Fahrenheit to about 450 degrees Fahrenheit.

In embodiments, pathogens are removed from said insects with microwave radiation. In embodiments, the microwave radiation is in the form of variable frequency microwave radiation. In embodiments, the variable frequency microwave radiation operates at a frequency between about 2 GHz to about 8 GHz. In embodiments, the variable frequency microwave radiation operates at a frequency of about 2.45 GHz.

In embodiments, the variable frequency microwave radiation operates at a power level between about 30 Watts to about 500 Watts. In embodiments, the variable frequency microwave radiation operates at a power level between about 50 Watts to about 150 Watts. In embodiments, the variable frequency microwave radiation operates at a power level between about 100 Watts to about 200 Watts. In embodiments, pathogens are removed from said insects over a duration of time between about 0.1 seconds to about 500 seconds. In embodiments, pathogens are removed from said insects over a duration of time between about 0.5 seconds to about 15 seconds.

FIG. 1A in no way describes every possible embodiment of the pathogen reduction disclosure because describing every possible embodiment would be impractical, if not impossible. FIG. 13 elaborates upon other possibilities related to removing pathogens from insects.

Multifunctional Flour Mixing (Step H)

The multifunctional flour mixing (step H) involves mixing the insects with fiber-starch materials, binding agents, density improving textural supplements, moisture improving textural supplements, and optionally *cannabis* enhancers, to form a multifunctional alimentary flour composition. The multifunctional alimentary flour composition may be further processed to create foodstuffs not only including ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multi-grain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, totopo, turkish delights, or waffles.

In embodiments, the fiber-starch materials may be comprised of singular or mixtures of cereal-grain-based materials, grass-based materials, nut-based materials, powdered fruit materials, root-based materials, tuber-based materials, or vegetable-based materials. In embodiments, the fiber-starch mass ratio ranges from between about 400 pounds of fiber-starch per ton of multifunctional flour to about 1800 pounds of fiber-starch per ton of multifunctional flour.

In embodiments, the binding agents may be comprised of singular or mixtures of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugars, syrups, tapioca, vegetable gums, or xanthan gum. In embodiments, the binding agent mass ratio ranges from between about 10 pounds of binding agent per ton of multifunctional flour to about 750 pounds of binding agent per ton of multifunctional flour.

In embodiments, the density improving textural supplements may be comprised of singular or mixtures of extracted arrowroot starch, extracted corn starch, extracted lentil starch, extracted potato starch, or extracted tapioca starch. In embodiments, the density improving textural supplement mass ratio ranges from between about 10 pounds of density improving textural supplement per ton of multifunctional flour to about 1000 pounds of density improving textural supplement per ton of multifunctional flour.

In embodiments, the moisture improving textural supplements may be comprised of singular or mixtures of almonds, brazil nuts, cacao, cashews, chestnuts, coconut, filberts, hazelnuts, Indian nuts, macadamia nuts, nut butters, nut oils, nut powders, peanuts, pecans, pili nuts, pine nuts, pinon nuts, pistachios, soy nuts, sunflower seeds, tiger nuts, and walnuts. In embodiments, the moisture improving textural supplement mass ratio ranges from between about 10 pounds of moisture improving textural supplement per ton of multifunctional flour to about 1000 pounds of moisture improving textural supplement per ton of multifunctional flour.

In embodiments, a *cannabis* enhancer may be added to the multifunctional flour. The *cannabis* may be marijuana in a powdered, dried, ground, or decarboxylated form. In embodiments, the *cannabis* enhancer may be remnants of vaporization, such as substantially fixed carbon feedstock components. In embodiments, the *cannabis* enhancer may be comprised of volatile feedstock components and a solvent. In embodiments, the *cannabis* enhancer may be comprised of volatile feedstock components and an alcohol. The *cannabis* enhancer may be comprised of volatile feedstock components and fixed carbon feedstock components. In embodiments, *cannabis* enhancer may be comprised of volatile feedstock components. In embodiments, *cannabis* enhancer may be comprised of fixed carbon feedstock components.

In embodiments, the *cannabis* enhancer contains tetrahydrocannabinol (THC) in a mixture of volatile feedstock components and fixed carbon feedstock components.

In embodiments, the multifunctional alimentary flour ranges from between about 25 pounds of *cannabis* enhancer per ton of multifunctional alimentary flour to about 1800 pounds of *cannabis* enhancer per ton of multifunctional alimentary flour. In embodiments, the volatile feedstock component mass ratio ranges from between about 500 pounds of volatile feedstock components per ton of *cannabis* enhancer to about 2000 pounds of volatile feedstock components per ton of *cannabis* enhancer. In embodiments, the volatile feedstock component mass ratio ranges from between about 500 pounds of volatile feedstock components per ton of multifunctional flour to about 1750 pounds of volatile feedstock components per ton of multifunctional flour. In embodiments, the fixed carbon feedstock component mass ratio ranges from between about 100 pounds of fixed carbon feedstock components per ton of *cannabis* enhancer to about 1700 pounds of fixed carbon feedstock components per ton of *cannabis* enhancer. In embodiments, the fixed carbon feedstock component mass ratio ranges from between about 100 pounds of fixed carbon feedstock components per ton of multifunctional flour to about 1600 pounds of fixed carbon feedstock components per ton of multifunctional flour.

Accordingly, I wish to make my intentions clear—and at the same time put potential competitors on clear public notice. It is my intent that this portion of the specification especially relating to multifunctional flour mixing and all claims pertaining thereto receive a liberal construction and be interpreted to uphold and not destroy my rights as inventor. It is my intent that the claim terms be construed in a charitable and common-sensical manner, in a manner that encompasses the embodiments disclosed in this and other portions of the specification and drawings relating to multifunctional flour mixing without incorporating unrecited, unnecessary limitations. It is my intent that the specification relating to multifunctional flour mixing claim terms be construed as broadly as practicable while preserving the validity of the claims. It is my intent that the claim terms be construed in a manner consistent with the context of the overall claim language and this portion of the specification along with FIGS. 1B and 12A, without importing extraneous limitations from the specification or other sources into the claims, and without confining the scope of the claims to the exact representations depicted in the specification or drawings in FIGS. 1B and 12A. It is also my intent that not each and every term of the claim be systematically defined and rewritten. Claim terms and phrases should be construed only to the extent that it will provide helpful, clarifying guidance to the jury, or to the extent needed to resolve a legitimate, good faith dispute that is material to the questions of validity or infringement. Otherwise, simple claim terms and phrases should be presented to the jury without any potentially confusing and difficult-to-apply definitional construction.

FIG. 1C

FIG. 1C elaborates upon the non-limiting embodiment of FIG. 1 further including the sequence step of lipid extraction (step J).

FIG. 1C shows lipid extraction (step J) downstream of the each of the steps insect collection (step E), insect grinding (step F), and pathogen removal (step G).

The lipid extraction (step J) is configured to produce extracted lipids (028) from insects that were previously fed an enhanced feedstock. In embodiments, the insect fat mass ratio ranges from between about 100 pounds of fat per ton of insects produced to about 1800 pounds of fat per ton of insects produced. The egg-laying insects that are present within each feeding chambers, and those that are collected, optionally ground, and optionally exposed to a pathogen removal step are intentionally engineered by feeding an enhanced feedstock to possess a wide ranging fat content ranging from between about 5% to about 90% by weight of insects produced.

In embodiments, the feeding chamber produces insects having fatty acids including palmitoleic acid, linoleic acid, alpha-linoleic acid, oleic acid, gamma-linoleic acid, or stearic acid. The fatty acids of the insects that are fed the enhanced feedstock are lipids. The extraction and use of lipids has many beneficial applications in society involving medicine, nanotechnology, consumer products, and chemical production with minimal water, feedstock, and environmental impact.

Palmitoleic acid is used to increase insulin sensitivity by suppressing inflammation, reduce inflammation associated with eczema. It is also used in cosmetic products, medical products, and can preserve and treat leather. Linoleic acid is used in oil paints and varnishes and is used in quick-drying oils. It can be used to reduce acne. It has moisture retentive properties and is used to make lotions and soaps (silky feel). It is an essential fatty acid and an emulsifier. Alpha-Linolenic acid is an essential dietary requirement linked to cardiovascular health. Oleic acid is used in hair dyes and soaps (slippery feel). It is also used as a food additive. It is used to manufacture surfactants, soaps, and plasticizers. It is an emulsifying agent in foods and pharmaceuticals. It can penetrate the skin. It can act as an herbicide, insecticide, and fungicide. It can be used in a metallic soap and with copper to clean mildew. Gamma-Linolenic acid can help prevent nerve damage. Stearic acid is used in foundation, baby lotions, oils, powders, creams, shaving cream, body and hand cream, cleansers, foot powders, sprays, moisturizers, and soaps (hardness). Stearic acid is a thickener used to make creams, oil pastels, hard candies, and candles. It is a surfactant. It can be used as a lubricant additive in plasticized PVC compounds to aid processing. It is also used to make metallic soaps.

Rubber grade stearic acid can be used as a mold release lubricant for sintering, pressing ceramic powders, and latex foam. It is also used as a thickener in greases. It can be used as a viscosity modifier for oil extraction. Stearic acid combined with castor oil is used to make softeners for textile sizing. It can be used as a yarn lubricant. Isopropyl Palmitate is in baby lotion/powder/cream, foot powders and sprays. Glyceryl stearate is in nail products, tonics and dressings, cologne/perfumes, concealers, baby lotion/powder/cream, aftershave. Sorbitan stearate is in blush. TEA-Stearate is in mascara. Stearyl alcohol is in hair conditioner, hair straighteners and relaxers, tonics and dressings (help to style hair). Oleyl alcohol is in hair straighteners and relaxers, and concealers.

Lipids extracted from insects may also be used in emerging areas of nanotechnology having uses in many areas covering chemistry, engineering, materials science, physics and biology. In coming years, science will continue to develop and increasingly appreciate sources of fatty acids derived from insects. For example, investigators are now seriously focusing on insect derived fatty acids for use in biomedical sciences, such as bio-imaging, sensing and diagnosis of pathologies at early stages, targeted drug delivery, and for use with nano-devices that interact with the plasma eukaryotic or even prokaryotic cell membranes.

Herein are disclosed systems and methods for obtaining, in mass quantities, commercial scale output of insect based lipids for use in a variety of areas throughout society. In embodiments, the lipid extraction (step J) utilizes a lipid extraction unit to extract lipids from insects.

In embodiments, the lipid extraction unit is configured to extract lipids by use of a first immiscible liquid and a second immiscible liquid. In embodiments, the first immiscible liquid has a first density and a first molecular weight, and the second immiscible liquid has a second density and a second molecular weight. In embodiments, first density is greater than the second density. In embodiments, first molecular weight is greater than the second molecular weight. In embodiments, a first immiscible liquid and lipid mixture is formed which is comprised of a lipid portion and a first immiscible liquid portion. In embodiments, second immiscible liquid and particulate mixture is formed which is comprised of a particulate portion and a second immiscible liquid portion. In embodiments, the particulate portion is comprised of one or more from the group consisting of insect legs, and wings, and protein.

FIG. 2

FIG. 2 shows a non-limiting embodiment of an enhanced feedstock mixing module (1000) including a feedstock distribution module (1A), mineral distribution module (1B), vitamin distribution module (1C), polymer distribution module (1D), water distribution module (1E), and an enhanced feedstock distribution module (1F).

FIG. 2 displays a computer (COMP) that is integral to the Insect Production Superstructure System (IPSS). The computer (COMP) is configured to accept a variety of signals from process variables using a variety of sensors and/or controllers, and then apply advanced process logic control methodologies, strategies and/or sequences to realize modulation of actuators and/or valves to effectuate optimal operation of the Insect Production Superstructure Systems (IPSS) and its associated modules not only including feedstock mixing, feedstock splitting, insect feeding, insect breeding, insect collection, insect grinding, pathogen removal, multifunctional flour mixing, and lipid extraction modules. A variety of signals are sent to and from the computer (COMP) to a variety of controllers, sensors, valves, motors, actuators, and the like distributed throughout the entire Insect Production Superstructure System (IPSS).

The computer (COMP) applies the control approach and methodology for the each and every entire control loop on a continuous basis, a discrete basis, or a hybrid combination of a continuous basis and a discrete basis. Further, a computer may be applied to implement the control methodology by utilizing process variables obtained by either a continuous sensor, a discrete sensor, or a combination of a continuous sensor and a discrete sensor and hold the control action at a constant set-point at that specific control output until a later time when that control algorithm is executed. The time between successive interrogations or application of the control algorithm is applied by the control computer is defined as the control interval. The control interval for a continuous sensor is typically shorter than that of a discrete sensor and based upon commercially available mechanical, electrical, or digital continuous or discrete sensors, the control interval or control time can vary from 0.2 milliseconds, to 0.5 seconds, to 1.0 second, to 10 seconds, to 30 seconds, to 1 minute, to 5 minutes, to 10 minutes, to 30 minutes, to 1 hour, to 10 hours, or longer. The output from the control computer is transmitted to a controller device. From application of the control logic, the control computer can send a variety of signals to a variety of controllers.

In embodiments, the signals from controllers or sensors are inputted or outputted to and from a computer (COMP) by a user or operator via an input/output interface (I/O) as disclosed in FIG. 2 and many others (not only including FIGS. 3, 5, 6, 7, 8, 9, 10, 11, 12, 13, 14A, 14B, 15, 16, 17, 18, 19, 20, 21, 22, 23, 24, 25, 26, 27, 28, 29, 30, 31, 32, 33, 34, 35, 36, 37, 38, 39). Program and sequencing instructions may be executed to perform particular computational functions such as automated operation of the valves, actuators, controllers, motors, or the like. In one exemplary embodiment, a computer (COMP) includes a processor (PROC) coupled to a system memory (MEM) via an input/output interface (I/O). The processor (PROC) may be any suitable processor capable of executing instructions. System memory (MEM) may be configured to store instructions and data accessible by processor (PROC). In various embodiments, system memory (MEM) may be implemented using any suitable memory technology. In all illustrated embodiments, program instructions and data implementing desired functions are shown stored within system memory (MEM) as code (CODE). In embodiments, the I/O interface (I/O) may be configured to coordinate I/O traffic between processor (PROC) and system memory (MEM). In some embodiments, the I/O interface (I/O) is configured for a user or operator to input necessary sequencing protocol into the computer (COMP) for process execution, including sequence timing and repetition of a given number of states to realize a desired sequence of steps and/or states. In embodiments, the signals operatively coupled to a controller, valve, actuator, motor, or the like, may be an input value to be entered into the computer (COMP) by the I/O interface (I/O).

The system is fully flexible to be tuned, configured, and optimized to provide an environment for scheduling the appropriate process parameters by programmatically controlling the opening and closing of valves at specific time intervals, or strategically and systematically opening, closing, turning on, turning off, modulating, controlling, or operating motors, valves, or actuators at specific time intervals at specific times. In embodiments, a user or operator may define control loops, cycle times, step numbers, and states which may be programmed into the computer (COMP) by an operator accessible input/output interface (I/O).

Feedstock Distribution Module (1A)

FIG. 2 displays a feedstock distribution module (1A) including a feedstock tank (1A2) that is configured to accept a feedstock (1A1). The feedstock tank (1A2) has an interior (1A3), a feedstock input (1A4), a feedstock conveyor (1A5), and a feedstock conveyor output (1A6). The feedstock tank (1A2) accepts a feedstock (1A1) to the interior (1A3) and regulates and controls an engineered amount of feedstock (1A1) downstream to be mixed to form an enhanced feedstock. The feedstock conveyor (1A5) has an integrated feedstock mass sensor (1A7) that is configured to input and output a signal (1A8) to the computer (COMP). The feedstock conveyor motor (1A9) has a controller (1A10) that is configured to input and output a signal (1A11) to the computer (COMP). The feedstock mass sensor (1A7), feedstock conveyor (1A5), and feedstock conveyor motor (1A9) are coupled so as to permit the conveyance, distribution, or output of a precise flow of feedstock (1A1) via a feedstock transfer line (1A14). A feedstock moisture sensor (1A12A) is preferably installed on the feedstock transfer line (1A14) and is configured to input a signal (1A13A) to the computer (COMP).

Mineral Distribution Module (1B)

FIG. 2 displays a mineral distribution module (1B) including a mineral tank (1B2) that is configured to accept minerals (1B1). The mineral tank (1B2) has an interior (1B3), a mineral input (1B4), a mineral conveyor (1B5), and a mineral conveyor output (1B6). The mineral tank (1B2) accepts minerals (1B1) to the interior (1B3) and regulates and controls an engineered amount of minerals (1B1) downstream to be mixed to form an enhanced feedstock. The mineral conveyor (1B5) has an integrated mineral mass sensor (1B7) that is configured to input and output a signal (1B8) to the computer (COMP). The mineral conveyor motor (1B9) has a controller (1B10) that is configured to input and output a signal (1B11) to the computer (COMP). The mineral mass sensor (1B7), mineral conveyor (1B5), and mineral conveyor motor (1B9) are coupled so as to permit the conveyance, distribution, or output of a precise flow of minerals (1B1) via a mineral transfer line (1B12).

Vitamin Distribution Module (1C)

FIG. 2 displays a vitamin distribution module (1C) including a vitamin tank (1C2) that is configured to accept vitamins (1C1). The vitamin tank (1C2) has an interior (1C3), a vitamin input (1C4), a vitamin conveyor (1C5), and a vitamin conveyor output (1C6). The vitamin tank (1C2) accepts vitamins (1C1) to the interior (1C3) and regulates and controls an engineered amount of vitamins (1C1) downstream to be mixed to form an enhanced feedstock. The vitamin conveyor (1C5) has an integrated vitamin mass sensor (1C7) that is configured to input and output a signal (1C8) to the computer (COMP). The vitamin conveyor motor (1C9) has a controller (1C10) that is configured to input and output a signal (1C11) to the computer (COMP). The vitamin mass sensor (1C7), vitamin conveyor (1C5), and vitamin conveyor motor (1C9) are coupled so as to permit the conveyance, distribution, or output of a precise flow of vitamins (1C1) via a vitamin transfer line (1C12).

Polymer Distribution Module (1D)

FIG. 2 displays a polymer distribution module (1D) including a polymer tank (1D2) that is configured to accept polymer (1D1). The polymer tank (1D2) has an interior (1D3), a polymer input (1D4), a polymer conveyor (1D5), and a polymer conveyor output (1D6). The polymer tank (1D2) accepts polymer (1D1) to the interior (1D3) and regulates and controls an engineered amount of polymer (1D1) downstream to be mixed to form an enhanced feedstock. The polymer conveyor (1D5) has an integrated polymer mass sensor (1D7) that is configured to input and output a signal (1D8) to the computer (COMP). The polymer conveyor motor (1D9) has a controller (1D10) that is configured to input and output a signal (1D11) to the computer (COMP). The polymer mass sensor (1D7), polymer conveyor (1D5), and polymer conveyor motor (1D9) are coupled so as to permit the conveyance, distribution, or output of a precise flow of polymer (1D1) via a polymer transfer line (1D12). For the context of this disclosure a polymer (1D1) includes exoskeletons of insects separated from any plurality of separators (S1, S2, S3) contained within the insect evacuation module (3000). For the context of this disclosure a polymer (1D1) includes chitin having the formula of (C8H13O5N)n which is a long-chain polymer of an N-acetylglucosamine, a derivative of glucose, and is found in many places throughout the natural world. Chitin is a polymer and a characteristic component of the cell walls of fungi, the exoskeletons of arthropods such as crustaceans (e.g., crabs, lobsters and shrimps) and insects, the radulae of mollusks, and the beaks and internal shells of cephalopods, including squid and octopuses and on the scales and other soft tissues of fish and lissamphibians. Where recycle of the exoskeletons from the insect evacuation module (3000) to the insect feeding module (2000) is not possible the polymer (1D1) includes fish scales, fungi, cephalopod shells, cephalopod beaks, Lissamphibia shells, or keratin. In its pure, unmodified form, chitin is translucent, pliable, resilient, and quite tough.

Water Distribution Module (1E)

FIG. 2 illustrates one non-limiting embodiment of a water distribution module (1E) that removes contaminants from water (1E1) prior to mixing to form an enhanced feedstock. A source of water (1E1) is routed through a water input line (1E4) and through a first water treatment unit (1E6) and a second water treatment unit (1E11) and into the interior (1E17) of a water tank (1E16) where it is then pumped via a water supply pump (1E22), though a water control valve (1E36) and then mixed with feedstock (1A1), minerals (1B1), vitamins (1C1), and polymer (1D1) to form an enhanced feedstock. In embodiments, enhancers (1E44) may be added to the interior (1E17) of the water tank (1E16). In embodiments, the enhancers (1E44) may include niacin, taurine, glucuronic acid, malic acid, N-acetyl L tyrosine, L-phenylalanine, caffeine, citicoline, insect growth hormones, or steroids, or human growth hormones.

A first water pressure sensor (1E2) is positioned on the water input line (1E4) and is configured to input a signal (1E3) to the computer (COMP). In embodiments, contaminant-laden water (1E5) is routed through the water input line (1E4) and transferred to the first water treatment unit (1E6) via a first water treatment unit input (1E7). The first water treatment unit (1E6) has a first water treatment unit input (1E7) and a first water treatment unit output (1E8) and is configured to remove contaminants from the contaminant-laden water (1E5) to form a stream of first contaminant-depleted water (1E9) that is outputted via a first contaminant-depleted water transfer line (1E10). In embodiments, a first contaminant-depleted water (1E9) is routed through the first contaminant-depleted water transfer line (1E10) and transferred to the second water treatment unit (1E11) via a second water treatment unit input (1E12). The second water treatment unit (1E11) has a second water treatment unit input (1E12) and a second water treatment unit output (1E13) and is configured to remove contaminants from the first contaminant-depleted water (1E9) to form a stream of second contaminant-depleted water (1E14) that is outputted via a second contaminant-depleted water transfer line (1E15).

The second contaminant-depleted water transfer line (1E15) is connected to the water tank (1E16) via a water input (1E18). In embodiments, the second contaminant-depleted water transfer line (1E15) has a water supply valve (1E23) interposed in between the second water treatment unit (1E11) and the water tank (1E16). In embodiments, the pressure drop across the water supply valve (1E23) may range from: between about 1 pound per square inch to about 5 pound per square inch; between about 5 pound per square inch to about 10 pound per square inch; between about 10 pound per square inch to about 15 pound per square inch; between about 15 pound per square inch to about 20 pound per square inch; between about 25 pound per square inch to about 30 pound per square inch; between about 35 pound per square inch to about 40 pound per square inch; between about 45 pound per square inch to about 50 pound per square inch; between about 55 pound per square inch to about 60 pound per square inch; between about 65 pound per square inch to about 70 pound per square inch; between about 75 pound per square inch to about 80 pound per square inch; between about 85 pound per square inch to about 90 pound per square inch; between about 95 pound per square inch to about 100 pound per square inch; between about 100 pound per square inch to about 125 pound per square inch; between about 125 pound per square inch to about 150 pound per square inch; or, between about 150 pound per square inch to about 200 pound per square inch.

The water supply valve (1E23) has a controller (1E24) that is configured to input and output a signal (1E25) to the computer (COMP). In embodiments, a source of water (1E1) may be introduced to the interior (1E17) of the water tank (1E16) via a water supply line (1E19) and water input (1E18). The first water treatment unit (1E6) and second water treatment unit (1E11) are optional because in many areas of the world the water quality is suitable for humans and animals to drink and ingest.

The water tank (1E16) is equipped with a high water level sensor (1E26) and a low water level sensor (1E28). The high water level sensor (1E26) is configured to input a signal (1E27) to the computer (COMP) when the level reaches a pre-determined highest most vertical height in the water tank (1E16). The low water level sensor (1E28) is configured to input a signal (1E29) to the computer (COMP) when the level reaches a pre-determined lowest most vertical height in the water tank (1E16).

A water supply pump (1E22) is connected to the water output (1E20) of the water tank (1E16) via a water discharge line (1E21). The water supply pump (1E22) is configured to transfer water (1E1) from the interior (1E17) of the water tank (1E16) to create a pressurized water supply (1E32) that is routed for mixing to form an enhanced feedstock via a pressurized water supply line (1E33).

A second water pressure sensor (1E30) is positioned on the discharge of the water supply pump (1E22) on the pressurized water supply line (1E33). The second water pressure sensor (1E30) is configured to input a signal (1E31) to the computer (COMP). A water flow sensor (1E34) is positioned on the discharge of the water supply pump (1E22) on the pressurized water supply line (1E33). The water flow sensor (1E34) is configured to input a signal (1E35) to the computer (COMP).

A water control valve (1E36) with an integrated controller (1E37) is positioned on the discharge of the water supply pump (1E22) on the pressurized water supply line (1E33). The controller (1E37) of the water control valve (1E36) is configured to input and output signal (1E38) to the computer (COMP). Water (1E1) routed through the water control valve (1E36) is then further routed towards being mixed to form an enhanced feedstock via a water transfer line (1E41). A water quality sensor (1E42) is positioned on the water transfer line (1E41) and is configured to input a signal (1E43) to the computer (COMP). A third water pressure sensor (1E39) is positioned on the water transfer line (1E41) and is configured to input a signal (1E40) to the computer (COMP).

The pressure drop across the water control valve (1E36) may range from: between about 1 pound per square inch to about 5 pound per square inch; between about 5 pound per square inch to about 10 pound per square inch; between about 10 pound per square inch to about 15 pound per square inch; between about 15 pound per square inch to about 20 pound per square inch; between about 25 pound per square inch to about 30 pound per square inch; between about 35 pound per square inch to about 40 pound per square inch; between about 45 pound per square inch to about 50 pound per square inch; between about 55 pound per square inch to about 60 pound per square inch; between about 65 pound per square inch to about 70 pound per square inch; between about 75 pound per square inch to about 80 pound per square inch; between about 85 pound per square inch to about 90 pound per square inch; between about 95 pound per square inch to about 100 pound per square inch; between about 100 pound per square inch to about 125 pound per square inch; between about 125 pound per square inch to about 150 pound per square inch; or, between about 150 pound per square inch to about 200 pound per square inch.

Enhancers (1E44) contained within the interior (1E46) of the enhancer tank (1E45) may be routed to the interior (1E17) of the water tank (1E16) via an enhancer transfer line (1E48). The enhancer transfer line (1E48) is connected at one end to the enhancer tank (1E45) via an enhancer tank output (1E47) and at another end to the water tank (1E16) via an enhancer input (1E49). A water enhancer supply valve (1E52) with an integrated controller (1E53) is positioned on the enhancer transfer line (1E48) and is configured to input and output a signal (1E54) to the computer (COMP). An enhancer flow sensor (1E50) is positioned on the enhancer transfer line (1E48) and is configured to input a signal (1E51) to the computer (COMP).

Feedstock (1A1), minerals (1B1), vitamins (1C1), polymer (1D1), and water (1E1) are mixed to form an enhanced feedstock that is routed to the interior (1F2) of the enhanced feedstock splitter (1F1) via an enhanced feedstock transfer line (1F0).

In embodiments, water may be added to the enhanced feedstock and transferred to the feeding chamber so that the insect feeding chamber operates at a water to insect ratio ranging from: between about 0.1 tons of water per ton of insects produced to about 0.2 tons of water per ton of insects produced; between about 0.2 tons of water per ton of insects produced to about 0.4 tons of water per ton of insects produced; between about 0.4 tons of water per ton of insects produced to about 0.6 tons of water per ton of insects produced; between about 0.6 tons of water per ton of insects produced to about 0.8 tons of water per ton of insects produced; between about 0.8 tons of water per ton of insects produced to about 1 ton of water per ton of insects produced; between about 1 ton of water per ton of insects produced to about 1.5 tons of water per ton of insects produced; between about 1.5 tons of water per ton of insects produced to about 2 tons of water per ton of insects produced; between about 2 tons of water per ton of insects produced to about 3 tons of water per ton of insects produced; between about 3 tons of water per ton of insects produced to about 4 tons of water per ton of insects produced; between about 4 tons of water per ton of insects produced to about 5 tons of water per ton of insects produced; between about 5 tons of water per ton of insects produced to about 6 tons of water per ton of insects produced; between about 6 tons of water per ton of insects produced to about 7 tons of water per ton of insects produced; between about 7 tons of water per ton of insects produced to about 8 tons of water per ton of insects produced; between about 8 tons of water per ton of insects produced to about 9 tons of water per ton of insects produced; between about 9 tons of water per ton of insects produced to about 10 tons of water per ton of insects produced; between about 10 tons of water per ton of insects produced to about 11 tons of water per ton of insects produced; between about 11 tons of water per ton of insects produced to about 12 tons of water per ton of insects produced; between about 12 tons of water per ton of insects produced to about 13 tons of water per ton of insects produced; between about 13 tons of water per ton of insects produced to about 14 tons of water per ton of insects produced; between about 14 tons of water per ton of insects produced to about 15 tons of water per ton of insects produced; between about 15 tons of water per ton of insects produced to about 16 tons of water per ton of insects produced; between about 16 tons of water per ton of insects produced to about 17 tons of water per ton of insects produced; between about 17 tons of water per ton of insects produced to about 18 tons of water per ton of insects produced; between about 18 tons of water per ton of insects produced to about 19 tons of water per ton of insects produced; or, between about 19 tons of water per ton of insects produced to about 20 tons of water per ton of insects produced.

Enhanced Feedstock Distribution Module (1F)

The enhanced feedstock splitter (1F1) has an interior (1F2), a splitter input (1F3), a first output (1F10), second output (1F15), and a third output (1F20). The enhanced feedstock splitter (1F1) is configured to mix the feedstock (1A1), minerals (1B1), vitamins (1C1), polymer (1D1), and water (1E1) and to split the mixed enhanced feedstock into a plurality of streams including a first enhanced feedstock stream (EF1), second enhanced feedstock stream (EF2), and a third enhanced feedstock stream (EF3). Each of the first enhanced feedstock stream (EF1), second enhanced feedstock stream (EF2), and third enhanced feedstock stream (EF3), may be transferred each to a first feeding chamber (FC1), second feeding chamber (FC2), and third feeding chamber (FC3), respectively.

An enhanced feedstock moisture sensor (1A12B) is positioned on the enhanced feedstock transfer line (1F0) and is configured to input a signal (1A13B) to the computer (COMP). The enhanced feedstock moisture sensor (1A12B) may be used to gauge the amount of moisture within the enhanced feedstock to increase or decrease the flow of water (1E1) passed through the water flow sensor (1E34) and water control valve (1E36).

The enhanced feedstock splitter (1F1) has a top section (1F4), bottom section (1F5), and at least one side wall (1F6). The enhanced feedstock splitter (1F1) may be cylindrical or rectangular or any other conceivable shape so long as it outputs at least one first enhanced feedstock stream. In embodiments, the enhanced feedstock splitter (1F1) has a splitter input (1F3) positioned on the top section (1F4).

In embodiments, the enhanced feedstock splitter (1F1) has a splitter first screw conveyor (1F9), splitter second screw conveyor (1F14), and splitter third screw conveyor (1F19) positioned on the bottom section (1F5). In embodiments, a first splitter level sensor (1F7) is positioned on the side wall (1F6) of the enhanced feedstock splitter (1F1) which is configured to input a signal (1F8) to the computer (COMP).

The splitter first screw conveyor (1F9) has a first output (1F10) and is configured to discharge a first enhanced feedstock stream (EF1) to a first feeding chamber (FC1). The splitter first screw conveyor (1F9) is equipped with a splitter first screw conveyor motor (1F11) and integrated controller (1F12) that is configured to input and output a signal (1F13) to the computer (COMP).

A first weigh screw (1F24) is positioned on the first output (1F10) of the splitter first screw conveyor (1F9). The first weigh screw (1F24) has a first weigh screw input (1F25) and a first weigh screw output (1F26), with an integrated mass sensor (1F27) that is configured to input a signal (1F28) to the computer (COMP). The first weigh screw (1F24) has a first weigh screw motor (1F29) with an integrated controller (1F30) that is configured to input and output a signal (1F31) to the computer (COMP). A first weighed enhanced feedstock stream (1F32) or a first enhanced feedstock stream (EF1) is discharged from the first weigh screw output (1F26).

The splitter second screw conveyor (1F14) has a first output (1F10) and is configured to discharge a second enhanced feedstock stream (EF2) to a second feeding chamber (FC2). The splitter second screw conveyor (1F14) is equipped with a splitter second screw conveyor motor (1F16) and integrated controller (1F17) that is configured to input and output a signal (1F18) to the computer (COMP). A second weigh screw (1F33) is positioned on the second output (1F15) of the splitter second screw conveyor (1F14). The second weigh screw (1F33) has a second weigh screw input (1F34) and a second weigh screw output (1F35), with an integrated mass sensor (1F26) that is configured to input a signal (1F37) to the computer (COMP). The second weigh screw (1F33) has a second weigh screw motor (1F38) with an integrated controller (1F39) that is configured to input and output a signal (1F40) to the computer (COMP). A second weighed enhanced feedstock stream (1F41) or a second enhanced feedstock stream (EF2) is discharged from the second weigh screw output (1F35).

The splitter third screw conveyor (1F19) has a first output (1F10) and is configured to third enhanced feedstock stream (EF3) to a third feeding chamber (FC3). The splitter third screw conveyor (1F19) is equipped with a splitter third screw conveyor motor (1F21) and integrated controller (1F22) that is configured to input and output a signal (1F23) to the computer (COMP). A third weigh screw (1F42) is positioned on the third output (1F20) of the splitter third screw conveyor (1F19). The third weigh screw (1F42) has a third weigh screw input (1F43) and a third weigh screw output (1F44), with an integrated mass sensor (1F45) that is configured to input a signal (1F46) to the computer (COMP). The third weigh screw (1F42) has a third weigh screw motor (1F47) with an integrated controller (1F48) that is configured to input and output a signal (1F49) to the computer (COMP). A third weighed enhanced feedstock stream (1F50) or a third enhanced feedstock stream (EF3) is discharged from the third weigh screw output (1F44).

FIG. 3

FIG. 3 shows a non-limiting embodiment of an insect feeding module (2000) integrated with an insect evacuation module (3000) operating in a first mode of operation wherein the egg transfer system (244) of the insect feeding module (2000) is at a first state in a first retracted height (H1).

A first weighed enhanced feedstock stream (1F32), or otherwise termed a first enhanced feedstock stream (EF1), is shown in FIG. 3 to be introduced to a first feeding chamber (FC1) of an insect feeding module (2000) via an enhanced feedstock input (206). The non-limiting description of the insect feeding module (2000) shown in FIG. 3 includes a feeding chamber (200). In embodiments, the feeding chamber (200) in FIG. 3 is a first feeding chamber (FC1) in an Insect Production Superstructure System (IPSS) that includes a plurality of insect feeding chambers (FC1, FC2, FC3). The insect feeding module (2000) is shown to be in fluid communication with an insect evacuation module (3000). The feeding chamber (200) contained within an insect feeding module (2000) of FIG. 3 is shown to be in fluid communication with a separator (300) contained within an insect evacuation module (3000).

The feeding chamber (200) of is shown to have an interior (201) defined by at least one side wall (202). Each side wall (202) of the embodiment of FIG. 3 is shown to have perforations as to be comprised of a mesh, or a screen, or the like. However, it is to be noted that any such wall, perforated or not perforated, screen or an impermeable surface shall suffice. It is also to be noted that the side wall (202) when made up of a screen-type material has opening that are lesser in size than the insects contained within the interior (201) of the feeding chamber (200).

In embodiments, the feeding chamber (200) has both a top (203) and a bottom (204). In the embodiment of FIG. 3, the top and bottom are both made up of a permeable metal or plastic or wire mesh or the like. However, in some embodiments, there is no bottom (204) at all, or the bottom is made up of a plurality of slats as described below. The first weighed enhanced feedstock stream (1F32), or otherwise termed a first enhanced feedstock stream (EF1), is introduced to a enhanced feedstock distributor (207) positioned within the interior (201) of the feeding chamber (200).

The feeding chamber is equipped with a humidity sensor (208) that is configured to measure the humidity within the interior (201) and input a signal (209) to the computer (COMP). The feeding chamber is equipped with a first temperature sensor (210) that is configured to measure the temperature of a first region within the interior (201) and input a signal (211) to the computer (COMP). The feeding chamber is equipped with a second temperature sensor (212) that is configured to measure the temperature of a first region within the interior (201) and input a signal (213) to the computer (COMP).

A network (220) of cells (219) are positioned within the interior (201) of the feeding chamber and are configured to permit insects (225) to reside therein. FIG. 4 shows one non-limiting embodiment of a network (220) of cells (219) for growing insects within a feeding chamber (200) of the insect feeding module (2000) shown in FIG. 3. The network (220) of cells (219) has openings (222) positioned at a first end (221) and openings (224) positioned at a second end (223). Insects (225) may reside in the passageways between the openings (222) at the first end (221) and the openings (224) at the second end (223). The cells (219) have a cell length (C-L) and a cell width (C-W). The network (220) of cells (219) has a network length (N-L) and a network width (N-W). In embodiments, the network (220) of cells (219) has a network length (N-L) that is greater than the network width (N-W). In embodiments, the network (220) of cells (219) has a network length (N-L) that is less than the network width (N-W). The cell width (C-W) is greater than the width (1$i$-W) of a first insect (1$i$) that resides within the interior (201) of the feeding chamber (200). The cell width (C-W) is greater than the average insect width (Ni-W) of a Nth insect (Ni) that collectively reside within the interior (201) of the feeding chamber (200). The cell length (C-L) is greater than the length (2$i$-L) of a first insect (1$i$) that resides within the interior (201) of the feeding chamber (200). The cell length (C-L) is greater than the average insect length (Ni-LW) of a Nth insect (Ni) that collectively reside within the interior (201) of the feeding chamber (200).

Obviously, many insects (225) may be present within the feeding chamber (200) at any given time.

This may include: a first insect (1$i$) having a first insect length (1$i$-L), a first insect width (1$i$-W), and a first insect mass (1$i$-WT); a second insect (2$i$) having a second insect length (2$i$-L), a second insect width (2$i$-W), and a second insect mass (2$i$-WT); and a Nth insect (Ni) that has an average insect length (Ni-L), an average insect width (Ni-W), and an average insect mass (Ni-WT). The average insect length (Ni-L) is the sum of the first insect length (1$i$-L) and the second insect length (2$i$-L) divided by the number of insects that being two in this particular instance and embodiment. The average insect width (Ni-W) is the sum of the first insect width (1$i$-W) and the second insect width (2$i$-W) divided by the number of insects that being two in this particular instance and embodiment. It is of course obvious to one of ordinary skill in the art that more than two insects (225, 1$i$, 2$i$) are contained within the interior (201) of the feeding chamber (200) and that both the average insect length (Ni-L) and average insect width (Ni-W) are averaged over a plurality of insects.

In embodiments, the cell width (C-W) ranges from: between about 0.125 inches to about 0.25 inches; between about 0.25 inches to about 0.50 inches; between about 0.5 inches to about 0.75 inches; between about 0.75 inches to about 1 inch; between about 1 inch to about 1.25 inches; between about 1.25 inch to about 1.50 inches; between about 1.50 inches to about 1.75 inches; between about 1.75 inches to about 2 inches; between about 2 inches to about 2.25 inches; between about 2.25 inches to about 2.50 inches; between about 2.50 inches to about 2.75 inches; between about 2.75 inches to about 2.75 inches; between about 2.75 inches to about 3 inches; between about 3 inches to about 3.25 inches; between about 3.25 inch to about 3.50 inches; between about 3.50 inches to about 3.75 inches; between about 3.75 inches to about 4 inches; between about 4 inches to about 4.25 inches; between about 4.25 inch to about 4.50 inches; between about 4.50 inches to about 4.75 inches; and, between about 4.75 inches to about 5 inches.

In embodiments, the cell length (C-L) ranges from: between about 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the average insect width (Ni-W) ranges from: between about 0.015625 inches to about 0.03125 inches; between about 0.03125 inches to about 0.0625 inches; between about 0.0625 inches to about 0.125 inches; between about 0.125 inches to about 0.25 inches; between about 0.25 inches to about 0.50 inches; between about 0.5 inches to about 0.75 inches; between about 0.75 inches to about 1 inch; between about 1 inch to about 1.25 inches; between about 1.25 inch to about 1.50 inches; between about 1.50 inches to about 1.75 inches; between about 1.75 inches to about 2 inches; between about 2 inches to about 2.25 inches; between about 2.25 inches to about 2.50 inches; between about 2.50 inches to about 2.75 inches; between about 2.75 inches to about 2.75 inches; and, between about 2.75 inches to about 3 inches.

In embodiments, the average insect length (Ni-L) ranges from: between about 0.125 inches to about 0.25 inches; between about 0.25 inches to about 0.50 inches; between about 0.5 inches to about 0.75 inches; between about 0.75 inches to about 1 inch; between about 1 inch to about 1.25 inches; between about 1.25 inch to about 1.50 inches; between about 1.50 inches to about 1.75 inches; between about 1.75 inches to about 2 inches; between about 2 inches to about 2.25 inches; between about 2.25 inches to about 2.50 inches; between about 2.50 inches to about 2.75 inches; between about 2.75 inches to about 2.75 inches; between about 2.75 inches to about 3 inches; between about 3 inches to about 3.25 inches; between about 3.25 inch to about 3.50 inches; between about 3.50 inches to about 3.75 inches; between about 3.75 inches to about 4 inches; between about 4 inches to about 4.25 inches; between about 4.25 inch to about 4.50 inches; between about 4.50 inches to about 4.75 inches; between about 4.75 inches to about 5 inches; between about 5 inches to about 5.25 inches; between about 5.25 inches to about 5.5 inches; between about 5.5 inches to about 5.75 inches; between about 5.75 inches to about 6 inches; between about 6 inches to about 7 inches; between about 7 inches to about 8 inches; between about 8 inches to about 9 inches; and, between about 9 inches to about 10 inches.

Referring again to FIG. 3, a vibration unit (214) may be connected to the network (220) of cells (219) at a first vibration unit connection (218A) and a second vibration unit connection (218B). The vibration unit (214) is equipped with a vibration unit motor (215) and integrated controller (216) that is configured to input and output a signal (217) to the computer (COMP). The vibration unit (214) is used to shake or to provide oscillations to occur within the network (220) of cells (219) to dislodge insects (225) from within the passageway between the first end (221) openings (222) and the second end (223) openings (224). Alternately, the vibration unit (214) may vibrate the entire feeding chamber (200) or at least a portion of the feeding chamber (200) so as to effectuate disclosing insects (225) from their resting surface within the network (220) of cells (219) in between the first end (221) openings (222) and the second end (223) openings (224).

In embodiments, a cell network differential pressure sensor (226) may be installed to measure to pressure across the network (220) of cells (219) to ascertain some measure of the mass or volume or quantity of insects that reside in between the first end (221) openings (222) and the second end (223) openings (224).

The cell network differential pressure sensor (226) is configured to input a signal (227) to the computer (COMP). When a pre-determined differential pressure is measured across the feeding chamber (200), insects may be evacuated therefrom. In embodiments, the pre-determined differential pressure across the feeding chamber (200) ranges from: about 0.015625 inches of water to about 0.03125 inches of water; between about 0.03125 inches of water to about 0.0625 inches of water; between about 0.0625 inches of water to about 0.125 inches of water; between about 0.125 inches of water to about 0.25 inches of water; between about 0.25 inches of water to about 0.50 inches of water; between about 0.5 inches of water to about 0.75 inches of water; between about 0.75 inches of water to about 1 inch; between about 1 inch to about 1.25 inches of water; between about 1.25 inch to about 1.50 inches of water; between about 1.50 inches of water to about 1.75 inches of water; between about 1.75 inches of water to about 2 inches of water; between about 2 inches of water to about 2.25 inches of water; between about 2.25 inches of water to about 2.50 inches of water; between about 2.50 inches of water to about 2.75 inches of water; between about 2.75 inches of water to about 2.75 inches of water; between about 2.75 inches of water to about 3 inches of water; between about 3 inches of water to about 3.25 inches of water; between about 3.25 inch to about 3.50 inches of water; between about 3.50 inches of water to about 3.75 inches of water; between about 3.75 inches of water to about 4 inches of water; between about 4 inches of water to about 4.25 inches of water; between about 4.25 inch to about 4.50 inches of water; between about 4.50 inches of water to about 4.75 inches of water; between about 4.75 inches of water to about 5 inches of water; between about 5 inches of water to about 5.25 inches of water; between about 5.25 inches of water to about 5.5 inches of water; between about 5.5 inches of water to about 5.75 inches of water; between about 5.75 inches of water to about 6 inches of water; between about 6 inches of water to about 7 inches of water; between about 7 inches of water to about 8 inches of water; between about 8 inches of water to about 9 inches of water; between about 10 inches of water to about 15 inches of water; between about 15 inches of water to about 20 inches of water; between about 20 inches of water to about 25 inches of water; between about 25 inches of water to about 30 inches of water; between about 30 inches of water to about 35 inches of water; between about 35 inches of water to about 40 inches of water; between about 40 inches of water to about 45 inches of water; between about 45 inches of water to about 50 inches of water; between about 50 inches of water to about 55 inches of water; between about 55 inches of water to about 60 inches of water; between about 60 inches of water to about 65 inches of water; between about 65 inches of water to about 70 inches of water; between about 70 inches of water to about 75 inches of water; between about 75 inches of water to about 80 inches of water; between about 80 inches of water to about 85 inches of water; between about 85 inches of water to about 90 inches of water; between about 90 inches of water to about 95 inches of water; and, between about 95 inches of water to about 100 inches of water.

The cell network differential pressure sensor (226) is connected to the interior (201) of the feeding chamber (200) by a first end impulse line (228) with a first end impulse line connection (232) and a second end impulse line (233) with a second end impulse line connection (237). FIG. 3 shows the first end impulse line (228) connected to the feeding chamber (200) via a first end impulse line connection (232) that is positioned vertically above the first end (221) openings (222) of the network (220) of cells (219). FIG. 3 also shows the second end impulse line (233) connected to the feeding chamber (200) via a second end impulse line connection (237) that is positioned vertically below the second end (223) openings (224) of the network (220) of cells (219).

The first end impulse line (228) and second end impulse line (233) are preferably tubes ranging from ⅛", ¼", ⅜", ½", ¾", or 1" stainless steel, plastic, polymer, metal tubing or piping. To prevent insects (225) from crawling up the first end impulse line (228), or to prevent clogging of particulates, and thus preventing the cell network differential pressure sensor (226) from accurately measuring differential pressure across the network (220) of cells (219), a first impulse line gas supply (231) may be provided to apply a continuous purge or gas, such as air, or CO2, or the like. The first impulse line gas supply (231) is controlled and set to a pre-determined flow rate by adjusting a first air purge flow regulator (230) wherein the flow rate is detected via a first air purge flow sensor (229). Similarly, to prevent insects (225) from crawling up the second end impulse line (233), or to prevent clogging of particulates, and thus preventing the cell network differential pressure sensor (226) from accurately measuring differential pressure across the network (220) of cells (219), a second impulse line gas supply (236) may be provided to apply a continuous purge or gas, such as air, or CO2, or the like. The second impulse line gas supply (236) is controlled and set to a pre-determined flow rate by adjusting a second air purge flow regulator (235) wherein the flow rate is detected via a second air purge flow sensor (234).

An air input (260) is configured to permit an air supply (262) to be transferred to the interior (201) of the feeding chamber (200) via an air supply entry conduit (261). An optional inlet gas distributor (263) may be positioned at the interface of the air input (260) so as to substantially uniformly distribute the air supply (262) over the cross-section of the interior (201) of the feeding chamber (200). In embodiments, the inlet gas distributor (263) may serve to effectuate a high velocity blast of air to the openings (222, 224) of the network (220) of cells (219) to aide in dislodging insects (225) from the cells (219) and to permit substantially complete evacuation of the egg-laying insects (225) present thing the interior (201) of the feeding chamber (200).

FIG. 3 shows an air supply fan (271) connected to the interior (201) of the feeding chamber (200) via the air supply entry conduit (261). The air supply fan (271) equipped with an air supply fan motor (272) and controller (273) is configured to input and output a signal (274) to the computer (COMP). An air heater (264) may be interposed in the air supply entry conduit (261) in between the air supply fan (271) and the feeding chamber (200).

Water (275) in the form of liquid or vapor may be introduced to the air supply entry conduit (261) via a water transfer line (276). A water input valve (278), and a water flow sensor (279) may also be installed on the water transfer line (276). The water flow sensor (279) is configured to input a signal (280) to the computer (COMP). The air supply (262) may be mixed with the water (275) in a water and gas mixing section (281) of the air supply entry conduit (261). FIG. 1 shows the water and gas mixing section (281) upstream of the air heater (264) but it may alternately also be placed downstream.

The air heater (264) may be electric, operated by natural gas, combustion, solar energy, alternative energy, or it may be a heat transfer device that uses a working heat transfer medium, such as steam or any other heat transfer medium known to persons having an ordinary skill in the art to which it pertains. FIG. 3 shows the air heater (264) to have a heat transfer medium input (265) and a heat transfer medium output (266).

In embodiments, heat transfer medium input (265) of the air heater (264) is equipped with a heat exchanger heat transfer medium inlet temperature (T3) that is configured to input a signal (XT3) to the computer (COMP). In embodiments, heat transfer medium output (266) of the air heater (264) is equipped with a heat exchanger heat transfer medium outlet temperature (T4) that is configured to input a signal (XT4) to the computer (COMP).

A first humidity sensor (267) is positioned on the discharge of the air supply fan (271) upstream of the water and gas mixing section (281). The first humidity sensor (267) is configured to input a signal (268) to the computer (COMP). A heat exchanger inlet gas temperature sensor (T1) is positioned on the discharge of the air supply fan (271) upstream of the air heater (264). The heat exchanger inlet gas temperature sensor (T1) is configured to input a signal (XT1) to the computer (COMP).

A second humidity sensor (269) is positioned on the discharge of the air heater (264) upstream of the air input (260) to the interior (201) of the feeding chamber (200). The second humidity sensor (266) is configured to input a signal (270) to the computer (COMP). A heat exchanger outlet gas temperature sensor (T2) is positioned on the discharge of the air heater (264) upstream of the air input (260) to the interior (201) of the feeding chamber (200). The heat exchanger outlet gas temperature sensor (T2) is configured to input a signal (XT2) to the computer (COMP).

In embodiments, the air supply fan (271), air heater (264), and air supply (262), permit the computer automation while integrated with the heat exchanger inlet gas temperature sensor (T1), heat exchanger outlet gas temperature sensor (T2), and feeding chamber (200) temperature sensors (210, 212), to operate under a wide variety of automated temperature operating conditions including varying the temperature range in the feeding chamber (200) from: between about 50 degrees Fahrenheit to about 55 degrees Fahrenheit; between about 55 degrees Fahrenheit to about 60 degrees Fahrenheit; between about 60 degrees Fahrenheit to about 65 degrees Fahrenheit; between about 65 degrees Fahrenheit to about 70 degrees Fahrenheit; between about 70 degrees Fahrenheit to about 75 degrees Fahrenheit; between about 75 degrees Fahrenheit to about 80 degrees Fahrenheit; between about 80 degrees Fahrenheit to about 85 degrees Fahrenheit; between about 85 degrees Fahrenheit to about 90 degrees Fahrenheit; between about 90 degrees Fahrenheit to about 95 degrees Fahrenheit; between about 95 degrees Fahrenheit to about 100 degrees Fahrenheit; between about 100 degrees Fahrenheit to about 105 degrees Fahrenheit; between about 105 degrees Fahrenheit to about 110 degrees Fahrenheit; between about 110 degrees Fahrenheit to about 115 degrees Fahrenheit; and, between about 115 degrees Fahrenheit to about 120 degrees Fahrenheit.

In embodiments, the air supply fan (271), air heater (264), air supply (262), and water (275) permit the computer automation while integrated with the first humidity sensor (267), second humidity sensor (269), and feeding chamber (200) humidity sensor (208), to operate under a wide variety of automated operating humidity conditions including varying the humidity range in the feeding chamber (200) from: between about 5 percent humidity to about 10 percent humidity; between about 10 percent humidity to about 15 percent humidity; between about 15 percent humidity to about 20 percent humidity; between about 20 percent humidity to about 25 percent humidity; between about 25 percent humidity to about 30 percent humidity; between about 30 percent humidity to about 35 percent humidity; between about 35 percent humidity to about 40 percent humidity; between about 40 percent humidity to about 45 percent humidity; between about 45 percent humidity to about 50 percent humidity; between about 50 percent humidity to about 55 percent humidity; between about 55 percent humidity to about 60 percent humidity; between about 60 percent humidity to about 65 percent humidity; between about 65 percent humidity to about 70 percent humidity; between about 70 percent humidity to about 75 percent humidity; between about 75 percent humidity to about 80 percent humidity; between about 80 percent humidity to about 85 percent humidity; between about 85 percent humidity to about 90 percent humidity; between about 90 percent humidity to about 95 percent humidity; and, between about 95 percent humidity to about 100 percent humidity.

FIG. 3 shows the feeding chamber (200) connected to a separator (300) via a feeding chamber exit conduit (302). The insect evacuation module (3000) shown in FIG. 3 only contains a first separator (S1), however it is to be noted that more than one separator (S2, S3) may be utilized in some circumstances.

The feeding chamber exit conduit (302) is connected at a first end to the feeding chamber (200) via an insect evacuation output (205) and connected at another end to a separator (300) via an insect and gas mixture input (303). The feeding chamber exit conduit (302) is configured to transfer an insect and gas mixture (304) from the feeding chamber (200) to the separator (300).

The insect and gas mixture (304) has an insect portion (304A) and a gas portion (304B). The gas portion is mostly air, however may contain some CO2 if some CO2 is used in the first impulse line gas supply (231) or the second impulse line gas supply (236). The separator (300), showing in FIG. 3 as a first separator (S1), is also shown in a filter. However, in other embodiments, the first separator (S1) may be a filter, a cyclone, or any other conceivable means to achieve the end of separating insects from a gas.

The separator (300) of FIG. 3 is a filter and contains an interior (301), an entry section (305) and an exit section (307). A filter element (306) separates the entry section (305) from the exit section (307) so as to only permit the gas portion (304B) of the insect and gas mixture (304) to flow through the filter element (306) from the entry section (305) to the exit section (307).

The insect portion (304A) of the insect and gas mixture (304) is retained within the entry section (305) because the pores or openings in the filter element (306) are smaller than the average insect length (Ni-L) or the average insect width (Ni-W) of the insects (225, Ni) contained within the interior (201) of the feeding chamber (200) and transferred to the separator (300).

A differential pressure sensor (308) is installed on the separator (300) to measure the pressure drop across the filter element (306) in between the entry section (305) and exit section (307). The differential pressure sensor (308) is configured to input a signal (309) to the computer (COMP). The differential pressure sensor (308) has an entry section impulse line (310) in fluid communication with the entry section (305) as well as an exit section impulse line (311) in fluid communication with the exit section (307).

An insect evacuation fan (312) pulls a vacuum through the separator (300, S1) and in turn pulls a vacuum on the feeding chamber (200). The insect evacuation fan (312) is configured to pull a vacuum on the feeding chamber to remove insects (225) from within the network (220) of cells 219). Specifically, the insect evacuation fan (312) pulls a vacuum on the network (220) of cells (219) and sucks insects from the in between the openings (222) of the first end (221) and the openings (224) of the second end (223) so as to substantially completely evacuate egg-laying insects (225) from the interior (201) of the feeding chamber (200).

When a vacuum is pulled on the feeding chamber the cell network differential pressure sensor (226) sends a signal (227) to the computer (COMP) so as to quantify the quantity of mass of insects (225) present within the network (220) of cells (219) within the feeding chamber (200) interior (201).

The insect evacuation fan (312) is equipped with a fan motor (314) and a controller (316) that is configured to input and output a signal (318) to the computer (COMP). The insect evacuation fan (312) is connected to the separator (300) via an insect-depleted gas output (321). The insect-depleted gas output (321) is configured to transfer an insect-depleted gas (320) from the separator (300) to the inlet of the insect evacuation fan (312). The insect-depleted gas (320) has a reduced amount of insects in it in reference to the insect and gas mixture (304). The insect evacuation fan (312) discharges the insect-depleted gas (320) via an insect-depleted gas exhaust line (322). A portion of the insect-depleted gas (320) that passes through the insect-depleted gas exhaust line (322) may be routed back to the separator to backflush the filter element (306). Thus, the insect-depleted gas exhaust line (322) is in fluid communication with the separator (300) via an insect-depleted gas recycle line (323) and an exhaust gas recycle input (324).

The separator (300) may be equipped with a valve (325) with a controller (326) that is configured to input a signal (327) to the computer (COMP). The valve (325) is preferably a rotary style valve, but may in some embodiments be that of a ball valve, butterfly valve, knife valve, piston valve, or plug valve.

The separator (300) may also be equipped with a separated insect conveyor (328) to remove separated insects (334) from the separator (300). The separated insect conveyor (328) has a motor (329) and a controller (330) that is configured to input and output a signal (331) to the computer (COMP). The separated insect conveyor (328) may also be equipped with a mass sensor (332) for weighing the separated insects (334) by sending a signal (333) to the computer (COMP). The separated insect conveyor (328) may be any type of conveyor, but preferably is a screw auger. Other types of conveyors are compression screw conveyors, conveyor belts, a pneumatic conveyor system, a vibrating conveyor system, a flexible conveyor system, a vertical conveyor system, a spiral conveyor system, a drag chain conveyor system, or a heavy duty rear conveyor system. Any conceivable type of mechanical handling equipment may be used so long as it can move separated insects (334) from one location to another. The separated insect conveyor (328) may route the separated insects (334) to a downstream location such as to a grinder, a pathogen removal unit, breeding chamber, a lipid extraction unit, or to a multifunctional flour mixing module.

In embodiments, the insect evacuation fan (312) is configured to remove a portion of egg-laying insects from the insect feeding chamber by applying a vacuum with a velocity pressure range from: between about 0.001 inches of water to about 0.005 inches of water; between about 0.005 inches of water to about 0.01 inches of water; between about 0.01 inches of water to about 0.02 inches of water; between about 0.02 inches of water to about 0.03 inches of water; between about 0.03 inches of water to about 0.04 inches of water; between about 0.04 inches of water to about 0.05 inches of water; between about 0.05 inches of water to about 0.06 inches of water; between about 0.06 inches of water to about 0.07 inches of water; between about 0.07 inches of water to about 0.08 inches of water; between about 0.08 inches of water to about 0.09 inches of water; between about 0.09 inches of water to about 0.1 inches of water; between about 0.1 inches of water to about 0.2 inches of water; between about 0.2 inches of water to about 0.3 inches of water; between about 0.3 inches of water to about 0.4 inches of water; between about 0.4 inches of water to about 0.5 inches of water; between about 0.5 inches of water to about 0.6 inches of water; between about 0.6 inches of water to about 0.7 inches of water; between about 0.7 inches of water to about 0.8 inches of water; between about 0.8 inches of water to about 0.9 inches of water; between about 0.9 inches of water to about 1 inch of water; between about 1 inch of water to about 1.25 inches of water; between about 1.25 inches of water to about 1.5 inches of water; between about 1.5 inches of water to about 2 inches of water; between about 2 inches of water to about 3 inches of water; between about 3 inches of water to about 4 inches of water; between about 4 inches of water to about 5 inches of water; between about 5 inches of water to about 6 inches of water; between about 6 inches of water to about 7 inches of water; between about 7 inches of water to about 8 inches of water; between about 8 inches of water to about 9 inches of water; between about 9 inches of water to about 10 inches of water; between about 10 inch of water to about 15 inches of water; between about 15 inches of water to about 25 inches of water; between about 25 inches of water to about 50 inches of water; between about 50 inches of water to about 75 inches of water; between about 75 inches of water to about 100 inches of water; between about 100 inches of water to about 150 inches of water; between about 150 inches of water to about 200 inches of water; between about 200 inches of water to about 250 inches of water; between about 250 inches of water to about 300 inches of water; between about 300 inches of water to about 350 inches of water; and, between about 350 inches of water to about 400 inches of water.

FIG. 3 shows one non-limiting embodiment of an egg transfer system (244) including a conveyor (245) equipped with a first conveyor elevation unit (254) and a second conveyor elevation unit (256) that is configured to extend in a vertical direction from supports (255, 257) from a first retracted height (H1) to a second elevated height (H2).

The conveyor (245) is configured to make an egg-depleted breeding material (246) available to the interior (201) of the feeding chamber (200). This is achieved by providing a conveyor (245) having an egg-depleted breeding material (246) provided thereon and extending the conveyor (245) in a vertical direction so that the conveyor (245) and egg-depleted breeding material (246) come into contact with the screen floor (258) of the feeding chamber (200). Egg-laying insects (225) lay their eggs (259) through the screen floor (258) of the feeding chamber (200) and deposit the eggs (259) into the breeding material (248) that rests upon the conveyor (245).

In the embodiment of FIG. 3, the egg-laying insects (225) present within the interior (201) of the feeding chamber (200) will deposit the eggs (259) into the breeding material (248) and the screen floor (258) will prevent them from eating or digging up the eggs (259). More on the different states of operation is discussed below in FIGS. 5 through 10.

The conveyor (245) receives egg-depleted breeding material (246) via a conveyor input (247). The egg-depleted breeding material (246) is then made available to the insects (225) within the feeding chamber (200). This is made possible in the embodiment of FIG. 3 by activating the first conveyor elevation unit (254) and second conveyor elevation unit (256) so as to extend the conveyor (245) vertically in a direction towards the bottom of the feeding chamber (200) from a first retracted height (H1) to a second elevated height (H2).

After insects (225) have laid their eggs (259) into the breeding material (248), the first conveyor elevation unit (254) and second conveyor elevation unit (256) are returned from a first retracted height (H1) to a second elevated height (H2) so as to lower the conveyor (245) vertically in a direction away from the bottom of the feeding chamber (200).

As a result of eggs (259) being deposited into the egg-depleted breeding material (246) an egg-laden breeding material (250) is created which is discharged from the conveyor via a conveyor output (249). The egg-laden breeding material (250) has a greater amount of eggs within it in reference to the egg-depleted breeding material (246). The egg-laden breeding material (250) is then transferred to a breeding chamber as described below in detail. The conveyor (245) is equipped with a conveyor motor (251) and a controller (252) that is configured to input and output a signal (253) to the computer (COMP). The first conveyor elevation unit (254) has a first support (255) and the second conveyor elevation unit (256) has a second support (257).

The breeding material (248) may be any conceivable material that is suitable for insects to deposit eggs into. In embodiments, the breeding material (248) is soil, mulch, compost, top soil, humus, clay, dirt, sand, minerals, organic matter, or a combination thereof. In embodiments, the breeding material (248) may be comprised of a gel, a damp substrate, vermiculite, leaves, grass clippings, peat moss, agricultural residue, wood chips, green waste, woodchip mulch, bark chips, straw mulch, hay, food waste, animal waste, cardboard, newspaper, carpet, foam, moss, recycled pulp, paper scraps, or feedstock, industrial waste, or any conceivable material that is suitable for an insect to lay eggs in.

FIG. 3 also shows that the feeding chamber (200) has a hatched insects input (240) that is configured to transfer hatched insects (239) from a breeding chamber to the interior (201) of the feeding chamber (200) via a breeding chamber insect transfer line (238). In embodiments where the Insect Production Superstructure System (IPSS) may have a plurality of insect feeding chambers (FC1, FC2, FC3), the first feeding chamber (FC1) is shown to have an egg-laying insects input (243) for transferring egg-laying insects (242) that were present within the second feeding chamber (FC2) or third feeding chamber (FC3) via a feeding chamber transfer line (241).

In embodiments, the feeding chamber grows insects within it over a time duration ranging from: between about 1 week to 2 weeks; between about 2 week to 3 weeks; between about 3 week to 4 weeks; between about 4 week to 5 weeks; between about 5 week to 6 weeks; between about 6 week to 7 weeks; between about 7 week to 8 weeks; between about 8 week to 9 weeks; between about 9 week to 10 weeks; between about 10 week to 11 weeks; between about 11 week to 12 weeks; between about 12 week to 13 weeks; between about 13 week to 14 weeks; or, between about 14 week to 15 weeks.

FIG. 4

FIG. 4 shows one non-limiting embodiment of a network (220) of cells (219) for growing insects within a feeding chamber (200) of the insect feeding module (2000) shown in FIG. 3.

FIG. 5

FIG. 5 elaborates upon the non-limiting embodiment of FIG. 3 but shows the insect feeding module (2000) operating in a second mode of operation wherein the egg transfer system (244) of the insect feeding module (2000) is at a second state at a second elevated height (H2) so as to permit insects (225) to lay eggs (259) within a provided breeding material (248).

As discussed above in FIG. 3, FIG. 5 shows the conveyor (245) configured to make breeding material (248) available to the interior (201) of the feeding chamber (200). This is achieved by providing a conveyor (245) having a breeding material (248) provided thereon and extending the conveyor (245) in a vertical direction so that the conveyor (245) and egg-depleted breeding material (246) come into contact with the screen floor (258) of the feeding chamber (200). Egg-laying insects (225) lay their eggs (259) through the screen floor (258) of the feeding chamber (200) and deposit the eggs (259) into the breeding material (248) that rests upon the conveyor (245).

In the embodiment of FIG. 5, the egg-laying insects (225) present within the interior (201) of the feeding chamber (200) will deposit the eggs (259) into the breeding material (248) and the screen floor (258) will prevent them from eating or digging up the eggs (259). The breeding material (248) is made available to the insects (225) within the feeding chamber (200). This is made possible in the embodiment of FIG. 5 by activating the first conveyor elevation unit (254) and second conveyor elevation unit (256) so as to extend the conveyor (245) vertically in a direction towards the bottom of the feeding chamber (200) from a first retracted height (H1) to a second elevated height (H2).

As a result of eggs (259) being deposited into the egg-depleted breeding material (246) an egg-laden breeding material (250) is created which is discharged from the conveyor via a conveyor output (249). The egg-laden breeding material (250) has a greater amount of eggs within it in reference to the egg-depleted breeding material (246).

FIG. 6

FIG. 6 elaborates upon the non-limiting embodiment of FIG. 3 but shows the insect feeding module (2000) operating in a third mode of operation wherein the egg transfer system (244) of the insect feeding module (2000) is at a first state in a first retracted height (H1) so as to discontinue insects (225) from laying eggs (259) within the provided breeding material (248).

As a result of eggs (259) being deposited into the egg-depleted breeding material (246) an egg-laden breeding material (250) is created which is discharged from the conveyor via a conveyor output (249). The egg-laden breeding material (250) has a greater amount of eggs within it in reference to the egg-depleted breeding material (246).

FIG. 7

FIG. 7 elaborates upon the non-limiting embodiment of FIG. 3 but shows the insect feeding module (2000) and insect evacuation module (3000) operating in a fourth mode of operation wherein a vibration unit (214) is activated to permit the removal of insects (225) from the network (220) of cells (219) and wherein the insect evacuation module (3000) separates insects from gas while a vacuum is pulled on the insect feeding module (2000) via an insect evacuation fan (312).

FIG. 8

FIG. 8 shows a non-limiting embodiment of an insect feeding module (2000) integrated with an insect evacuation module (3000) operating in a first mode of operation wherein a plurality of slats (341) of an egg transfer system (244) of the insect feeding module (2000) are in first closed state (341A).

Note that in FIG. 8, the enhanced feedstock input (206) is made available to the feeding chamber (206) at a vertical height within the interior below the network (220) of cells (219).

FIG. 8 discloses another embodiment of the feeding chamber (200) without a screen floor (258). Instead, a plurality of slats (341) define the bottom of the feeding chamber (200). The plurality of slats (341) are equipped with a slat motor (344) and controller (345) configured to rotate the slats (341) upon the input or output of a signal (346) to the computer (COMP). The slat motor (344) controller (345) is operatively equipped to rotate the slats (341) into a plurality of states including a first closed state (341A)

and a second open state (341B). The embodiments of FIGS. 8 and 9 show the plurality of rotatable slats (341) in the first closed state (341A).

The plurality of slats (341) define the lower section of the interior (201) of the feeding chamber (200) into an upper egg-laying section (342) and a lower egg transfer section (343). The upper egg-laying section (342) is the region within the interior (201) of the feeding chamber above the plurality of slats (341) and below the network (220) of cells (219) where the insects reside. The lower egg transfer section (343) is the region below the plurality of slats (341) and above the egg transfer system (244). The embodiment of FIG. 8 depicts the egg transfer system (244) equipped to output an egg-laden breeding material (339) via an egg-laden breeding material transfer line (340).

The embodiment of FIG. 8 also depicts the egg transfer system (244) equipped with egg-laden breeding material conveyor (347) with integral mass sensors (351, 353). Insects (225), as well as eggs (259), egg-laden breeding material (339) may also be removed via the egg transfer system (244). The egg-laden breeding material conveyor (347) has a motor (348) and a controller (349) that is configured to input and output a signal (350) to the computer (COMP). A first breeding material mass sensor (351) is operatively connected to the egg-laden breeding material conveyor (347) and is configured to input a signal (352) to the computer (COMP). A second breeding material mass sensor (353) is operatively connected to the egg-laden breeding material conveyor (347) and is configured to input a signal (354) to the computer (COMP).

FIG. 9

FIG. 9 elaborates upon the non-limiting embodiment of FIG. 8 and shows breeding material (248) resting upon the surface of the plurality of slats (341) of the egg transfer system (244) so as to permit insects (225) to lay eggs (259) within the breeding material (248).

FIG. 10

FIG. 10 elaborates upon the non-limiting embodiment FIG. 8 but shows the egg transfer system (244) in a second open state (341A) so as to permit egg-laden breeding material (248) to pass through the plurality of slats (341) while the vibration unit (214) is activated, some insects (225) may pass through the open slats (341) as well.

FIG. 11

FIG. 11 shows a simplistic diagram illustrating an insect grinding module that is configured to grind at least a portion of the insects transferred from the insect evacuation module (3000). A grinder (1250) is shown to grind the separated insects (334) into a stream of ground separated insects (1500). The ground separated insects (1500) may be sent to the lipid extraction unit (1501) on FIG. 12, the pathogen removal unit (1550) on FIG. 13, or the multifunctional flour mixing module (6000) on FIG. 14A.

FIG. 12

FIG. 12 shows a simplistic diagram illustrating a lipid extraction module that is configured to extract lipids from at least a portion of the insects transferred from the insect evacuation module (3000).

FIG. 12 discloses a lipid extraction unit (1501) for extracting insect based lipids in mass quantities for commercial scale output for use in a variety of areas throughout society. In embodiments, the lipid extraction unit (1501) includes a decanter (1502) having an interior (1505) defined by at least one side wall (1504). A weir (1503) may be positioned in the decanter (1502). In embodiments, the lipid extraction unit (1501) may be a decanter (1502) in the form of a vertical or horizontal decanter (1502). Separated insects (334) are provided to the lipid extraction unit (1501) from either the separated insect conveyor (328) via the separator or the ground separated insects (1500) via the grinder (1250). Separated insects (334) are introduced to the lipid extraction unit (1501) via a separator insect input (1508) and optionally introduced to the interior (1505) beneath the liquid level of the via a diptube (1509).

In embodiments, the lipid extraction unit (1501) is configured to extract lipids by use of a first immiscible liquid (1506) and a second immiscible liquid (1507). In embodiments, the first immiscible liquid (1506) has a first density (RHO1) and a first molecular weight (MW1), and the second immiscible liquid (1507) has a second density (RHO2), and a second molecular weight (MW2). In embodiments, first density (RHO1) is greater than the second density (RHO2). In embodiments, first molecular weight (MW1) is greater than the second molecular weight (MW2).

In embodiments, the first immiscible liquid (1506) is an organic compound, such as chloroform, with a first density (RHO1) of about 87 pounds per cubic foot, and a first molecular weight (MW1) of about 119 pound mass per pound mole. In embodiments, the second immiscible liquid (1507) is an alcohol, such as methanol, with a second density (RHO2) of about 44 pounds per cubic foot, and a second molecular weight (MW2) of about 32 pound mass per pound mole. In embodiments, the first density (RHO1) ranges from between about 70 pounds per cubic foot to about 110 pounds per cubic foot. In embodiments, the second density (RHO2) ranges from between about 25 pounds per cubic foot to about 69 pounds per cubic foot. In embodiments, the first molecular weight (MW1) ranges from between about 70 pound mass per pound mole to about 150 pound mass per pound mole. In embodiments, the second molecular weight (MW2) ranges from between about 18 pound mass per pound mole to about 69 pound mass per pound mole.

The weir (1503) separates the decanter (1502) into a first section (1515) and a second section (1516). A first level sensor (1510) is positioned within the interior (1505) to detect the level of the interface region (1512) between the first immiscible liquid (1506) and the second immiscible liquid (1507) within the first section (1515). The first level sensor (1510) is configured to output a signal (1511) to the computer (COMP). A second level sensor (1513) is positioned within the interior (1505) to detect the level of the second immiscible liquid (1507) within the second section (1516). The second level sensor (1513) is configured to output a signal (1514) to the computer (COMP).

In embodiments, a first immiscible liquid and lipid mixture (1518) is formed which is comprised of a lipid portion and a first immiscible liquid portion. In embodiments, a second immiscible liquid and particulate mixture (1521) is formed which is comprised of a particulate portion and a second immiscible liquid portion. In embodiments, the particulate portion is comprised of one or more from the group consisting of insect legs, and wings, and protein. In embodiments, the second immiscible liquid (1507) floats above first immiscible liquid (1506) in the first section (1515) of the decanter (1502). An interface region (1512) is the region in the first section (1515) of the decanter (1502) in between the upper second immiscible liquid (1507) and the lower first immiscible liquid (1506).

The decanter (1502) has a first immiscible liquid and lipid mixture output (1517) for discharging a first immiscible liquid and lipid mixture (1518) towards a lipid transfer pump (1519). The decanter (1502) also has a second immiscible liquid and particulate mixture output (1520) for discharging a second immiscible liquid and particulate mixture (1521) towards a second immiscible liquid recirculation pump (1522) and particulate filter (1523). The particulate filter (1523) has a second immiscible liquid input (1524), second immiscible liquid output (1525), and a filtered protein output (1532).

A particulate-depleted second immiscible liquid (1526) is discharged from the second immiscible liquid output (1525) of the particulate filter (1523) and returned to the decanter (1502) via a particulate-depleted liquid input (1527). A filtered protein stream (1531) is discharged from the filtered protein output (1532) of the particulate filter (1523). The decanter (1502) also has an interface layer protein take-off point (1528) configured to transfer an interface layer protein stream (1529) to an interface layer protein pump (1530). The interface layer protein stream (1529) is comprised of particulates including insect legs, and wings, and protein from the interface region (1512). A temperature sensor (1533) is operatively connected to the lipid extraction unit (1501) and is configured to input a signal (1534) to the computer (COMP).

FIG. 13

FIG. 13 shows a simplistic diagram illustrating a pathogen removal module that is configured to remove pathogens from at least a portion of the insects transferred from the insect evacuation module (3000).

FIG. 14A

FIG. 14A shows a simplistic diagram illustrating a multifunctional flour mixing module that is configured to generate a multifunctional alimentary flour from at least a portion of the insects transferred from the pathogen removal module and including the sequence steps or sub-modules including an insect distribution module (6A), fiber-starch distribution module (6B), binding agent distribution module (6C), density improving textural supplement distribution module (6D), moisture improving textural supplement distribution module (6E), multifunctional flour mixing module (6F).

Insect Distribution Module (6A)

FIG. 14A displays an insect distribution module (6A) including an insect tank (6A2) that is configured to accept insects (6A1). The insect tank (6A2) has an interior (6A3), an insect input (6A4), an insect conveyor (6A5), and an insect conveyor output (6A6). The insect tank (6A2) accepts insects (6A1) to the interior (6A3) and regulates and controls an engineered amount of insects (6A1) downstream to be mixed to form a multifunctional alimentary flour. The insect conveyor (6A5) has an integrated insect mass sensor (6A7) that is configured to input and output a signal (6A8) to the computer (COMP). The insect conveyor motor (6A9) has a controller (6A10) that is configured to input and output a signal (6A11) to the computer (COMP). The insect mass sensor (6A7), insect conveyor (6A5), and insect conveyor motor (6A9) are coupled so as to permit the conveyance, distribution, or output of a precise flow of insect (6A1) via an insect transfer line (6A12).

Fiber-Starch Distribution Module (6B)

FIG. 14A displays a fiber-starch distribution module (6B) including a fiber-starch tank (6B2) that is configured to accept fiber-starch (6B1). The fiber-starch tank (6B2) has an interior (6B3), a fiber-starch input (6B4), a fiber-starch conveyor (6B5), and a fiber-starch conveyor output (6B6). The fiber-starch tank (6B2) accepts fiber-starch (6B1) to the interior (6B3) and regulates and controls an engineered amount of fiber-starch (6B1) downstream to be mixed to form a multifunctional alimentary flour. The fiber-starch conveyor (6B5) has an integrated fiber-starch mass sensor (6B7) that is configured to input and output a signal (6B8) to the computer (COMP). The fiber-starch conveyor motor (6B9) has a controller (6B10) that is configured to input and output a signal (6B11) to the computer (COMP). The fiber-starch mass sensor (6B7), fiber-starch conveyor (6B5), and fiber-starch conveyor motor (6B9) are coupled so as to permit the conveyance, distribution, or output of a precise flow of fiber-starch (6B1) via a fiber-starch transfer line (6B12).

Binding Agent Distribution Module (6C)

FIG. 14A displays a binding agent distribution module (6C) including a binding agent tank (6C2) that is configured to accept a binding agent (6C1). The binding agent tank (6C2) has an interior (6C3), a binding agent input (6C4), a binding agent conveyor (6C5), and a binding agent conveyor output (6C6). The binding agent tank (6C2) accepts binding agent (6C1) to the interior (6C3) and regulates and controls an engineered amount of a binding agent (6C1) downstream to be mixed to form a multifunctional alimentary flour. The binding agent conveyor (6C5) has an integrated binding agent mass sensor (6C7) that is configured to input and output a signal (6C8) to the computer (COMP). The binding agent conveyor motor (6C9) has a controller (6C10) that is configured to input and output a signal (6C11) to the computer (COMP). The binding agent mass sensor (6C7), binding agent conveyor (6C5), and binding agent conveyor motor (6C9) are coupled so as to permit the conveyance, distribution, or output of a precise flow of binding agent (6C1) via a binding agent transfer line (6C12).

Density Improving Textural Supplement Distribution Module (6D)

FIG. 14A displays a density improving textural supplement distribution module (6D) including a density improving textural supplement tank (6D2) that is configured to accept a density improving textural supplement (6D1). The density improving textural supplement tank (6D2) has an interior (6D3), a density improving textural supplement input (6D4), a density improving textural supplement conveyor (6D5), and a density improving textural supplement conveyor output (6D6). The density improving textural supplement tank (6D2) accepts density improving textural supplement (6D1) to the interior (6D3) and regulates and controls an engineered amount of a density improving textural supplement (6D1) downstream to be mixed to form a multifunctional alimentary flour. The density improving textural supplement conveyor (6D5) has an integrated density improving textural supplement mass sensor (6D7) that is configured to input and output a signal (6D8) to the computer (COMP). The density improving textural supplement conveyor motor (6D9) has a controller (6D10) that is configured to input and output a signal (6D11) to the computer (COMP). The density improving textural supplement mass sensor (6D7), density improving textural supplement conveyor (6D5), and density improving textural supplement conveyor motor (6D9) are coupled so as to permit the conveyance, distribution, or output of a precise flow of density improving textural supplement (6D1) via a density improving textural supplement transfer line (6D12).

Moisture Improving Textural Supplement Distribution Module (6E)

FIG. 14A displays a moisture improving textural supplement distribution module (6E) including a moisture improving textural supplement tank (6E2) that is configured to accept a moisture improving textural supplement (6E1). The moisture improving textural supplement tank (6E2) has an interior (6E3), a moisture improving textural supplement input (6E4), a moisture improving textural supplement conveyor (6E5), and a moisture improving textural supplement conveyor output (6E6). The moisture improving textural supplement tank (6E2) accepts a moisture improving textural supplement (6E1) to the interior (6E3) and regulates and controls an engineered amount of a moisture improving textural supplement (6E1) downstream to be mixed to form a multifunctional alimentary flour. The moisture improving textural supplement conveyor (6E5) has an integrated moisture improving textural supplement mass sensor (6E7) that is configured to input and output a signal (6E8) to the computer (COMP). The moisture improving textural supplement conveyor motor (6E9) has a controller (6E10) that is configured to input and output a signal (6E11) to the computer (COMP). The moisture improving textural supplement mass sensor (6E7), moisture improving textural supplement conveyor (6E5), and moisture improving textural supplement conveyor motor (6E9) are coupled so as to permit the conveyance, distribution, or output of a precise flow of moisture improving textural supplement (6E1) via a moisture improving textural supplement transfer line (6E12).

Cannabis Enhancer Distribution Module (6G)

FIG. 14A displays a cannabis enhancer distribution module (6G) including a cannabis enhancer tank (6G2) that is configured to accept a cannabis enhancer (6G1). The cannabis enhancer tank (6G2) has an interior (6G3), a cannabis enhancer input (6G4), a cannabis enhancer conveyor (6G5), and a cannabis enhancer conveyor output (6G6). The cannabis enhancer tank (6G2) accepts a cannabis enhancer (6G1) to the interior (6G3) and regulates and controls an engineered amount of a cannabis enhancer (6G1) downstream to be mixed to form a multifunctional alimentary flour. The cannabis enhancer conveyor (6G5) has an integrated cannabis enhancer mass sensor (6G7) that is configured to input and output a signal (6G8) to the computer (COMP). The cannabis enhancer conveyor motor (6G9) has a controller (6G10) that is configured to input and output a signal (6G11) to the computer (COMP). The cannabis enhancer mass sensor (6G7), cannabis enhancer conveyor (6G5), and cannabis enhancer conveyor motor (6G9) are coupled so as to permit the conveyance, distribution, or output of a precise flow of cannabis enhancer (6G1) via a cannabis enhancer transfer line (6G12).

Multifunctional Flour Mixing Module (6F)

FIG. 14A displays a multifunctional flour mixing module (6F) including a multifunctional flour tank (6F1) that is configured to accept a mixture including insects (6A1), fiber-starch (6B1), binding agent (6C1), density improving textural supplement (6D1), moisture improving textural supplement (6E1), and cannabis enhancer (6G1) via a multifunctional flour transfer line (6F0). The insects (6A1) may be pathogen-depleted insects (1570) transferred from the pathogen removal unit (1550) as depicted in FIG. 14A. FIG. 14B shows the insects (6A1) as ground separated insects (1500) transferred from the grinder (1250). The multifunctional flour tank (6F1) has an interior (6F2), a multifunctional flour tank input (6F3), screw conveyor (6F9), multifunctional flour output (6F10). The multifunctional flour tank (6F1) accepts insects (6A1), fiber-starch (6B1), binding agent (6C1), density improving textural supplement (6D1), moisture improving textural supplement (6E1), and cannabis enhancer (6G1) to the interior (6F2) and mixes, regulates, and outputs a weighed multifunctional flour stream (6F22).

The multifunctional flour tank (6F1) has a top section (6F4), bottom section (6F5), at least one side wall (6F6), with a level sensor (6F7) positioned thereon that is configured to input and output a signal (6F8) to the computer (COMP). The screw conveyor (6F9) has a multifunctional flour conveyor motor (6F11) with a controller (6F12) that is configured to input and output a signal (6F13) to the computer (COMP). From the multifunctional flour output (6F10) of the multifunctional flour tank (6F1) is positioned a multifunctional flour weigh screw (6F14) that is equipped with a multifunctional flour weigh screw input (6F15), a multifunctional flour weigh screw output (6F16), and a mass sensor (6F17) that is configured to input and output a signal (6F18) to the computer (COMP). The multifunctional flour weigh screw (6F14) also has a weigh screw motor (6F19) with a controller (6F20) that is configured to input and output a signal (6F21) to the computer (COMP).

FIG. 14B

FIG. 14B shows a simplistic diagram illustrating a multifunctional flour mixing module that is configured to generate a multifunctional alimentary flour as described in FIG. 14A however instead from at least a portion of the insects transferred from the insect grinding module.

FIG. 15

FIG. 15 shows a simplistic diagram illustrating a plurality of feeding chambers (FC1, FC2, FC3) of an insect feeding module (2000) integrated within one common separator (300) of an insect evacuation module (3000).

FIG. 15 shows an insect feeding module (2000) comprised of three separate feeding chambers (FC1, FC2, FC3) including a first feeding chamber (FC1), second feeding chamber (FC2), and a third feeding chamber (FC3). Each feeding chamber (FC1, FC2, FC3) may include the non-limiting embodiments of those previously described or those described below. It is well established that the claims of the patent serve an important public notice function to potential competitors—enabling them to not only determine what is covered, but also what is not covered—by the patent. And a number of Federal Circuit decisions have emphasized the importance of discerning the patentee's intent—as expressed in the specification—in construing the claims of the patent. The present disclosure includes several independently meritorious inventive aspects and advantages related feeding and evacuating insects by use of at least one insect feeding module (2000) integrated at least one separator (300) of an insect evacuation module (3000) and to the notion that each feeding chamber (FC1, FC2, FC3) has a feeding chamber insect evacuation output (205A, 205B, 205C) that is connected to the separator (300) of the insect evacuation module (3000).

First Feeding Chamber (FC1)

The first feeding chamber (FC1) has a first feeding chamber insect evacuation output (205A) or a feeding chamber 1 insect evacuation port (1FC) that is in fluid communication with the insect and gas mixture input (303) of the separator (300). A first feeding chamber exit conduit (302A) is connected at one end to the first feeding chamber (FC1) and at another and to a common entry conduit (CEC). The common entry conduit (CEC) is connected at one end to the first feeding chamber exit conduit (302A) and at another end to the insect and gas mixture input (303) of the separator (300). A feeding chamber 1 evacuation valve (VV1) in interposed in the first feeding chamber exit conduit (302A). The feeding chamber 1 evacuation valve (VV1) is equipped with a with a controller (CV1) that is configured to input and output a signal (XV1) to the computer (COMP). The first feeding chamber exit conduit (302A) has a first feeding chamber evacuation line first diameter (D1A) and a first feeding chamber evacuation line reducer (VR1) which merges into a first feeding chamber evacuation line second diameter (D1B). In embodiments, the first feeding chamber evacuation line first diameter (D1A) is greater than the first feeding chamber evacuation line second diameter (D1B). In embodiments, the first feeding chamber evacuation line first diameter (D1A) is less than the first feeding chamber evacuation line second diameter (D1B).

In embodiments, the first feeding chamber evacuation line first diameter (D1A) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the first feeding chamber evacuation line second diameter (D1B) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the common entry conduit (CEC) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

Second Feeding Chamber (FC2)

The second feeding chamber (FC2) has a second feeding chamber insect evacuation output (205B) or a feeding chamber 2 insect evacuation port (2FC) that is in fluid communication with the insect and gas mixture input (303) of the separator (300). A second feeding chamber exit conduit (302B) is connected at one end to the second feeding chamber (FC2) and at another and to a common entry conduit (CEC). The common entry conduit (CEC) is connected at one end to the second feeding chamber exit conduit (302B) and at another end to the insect and gas mixture input (303) of the separator (300). A feeding chamber 2 evacuation valve (VV2) in interposed in the second feeding chamber exit conduit (302B). The feeding chamber 2 evacuation valve (VV2) is equipped with a with a controller (CV2) that is configured to input and output a signal (XV2) to the computer (COMP). The second feeding chamber exit conduit (302B) has a second feeding chamber evacuation line first diameter (D2A) and a second feeding chamber evacuation line reducer (VR2) which merges into a second feeding chamber evacuation line second diameter (D2B). In embodiments, the second feeding chamber evacuation line first diameter (D2A) is greater than the second feeding chamber evacuation line second diameter (D2B). In embodiments, the second feeding chamber evacuation line first diameter (D2A) is less than the second feeding chamber evacuation line second diameter (D2B).

In embodiments, the second feeding chamber evacuation line first diameter (D2A) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the second feeding chamber evacuation line second diameter (D2B) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

Third Feeding Chamber (FC3)

The third feeding chamber (FC3) has a third feeding chamber insect evacuation output (205C) or a feeding chamber 3 insect evacuation port (2FC) that is in fluid communication with the insect and gas mixture input (303) of the separator (300). The third feeding chamber (FC3) has a third feeding chamber insect evacuation output (205C) or a feeding chamber 3 insect evacuation port (3FC) that is in fluid communication with the insect and gas mixture input (303)

of the separator (300). A third feeding chamber exit conduit (302C) is connected at one end to the third feeding chamber (FC3) and at another end to a common entry conduit (CEC). The common entry conduit (CEC) is connected at one end to the third feeding chamber exit conduit (302C) and at another end to the insect and gas mixture input (303) of the separator (300). A feeding chamber 3 evacuation valve (VV3) in interposed in the third feeding chamber exit conduit (302C). The feeding chamber 3 evacuation valve (VV3) is equipped with a with a controller (CV3) that is configured to input and output a signal (XV3) to the computer (COMP). The third feeding chamber exit conduit (302C) has a third feeding chamber evacuation line first diameter (D3A) and a third feeding chamber evacuation line reducer (VR3) which merges into a third feeding chamber evacuation line second diameter (D3B). In embodiments, the third feeding chamber evacuation line first diameter (D3A) is greater than the third feeding chamber evacuation line second diameter (D3B). In embodiments, the third feeding chamber evacuation line first diameter (D3A) is less than the third feeding chamber evacuation line second diameter (D3B).

In embodiments, the third feeding chamber evacuation line first diameter (D3A) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

In embodiments, the third feeding chamber evacuation line second diameter (D3B) ranges in size from: between about 1 inch and about 2 inches; between about 2 inches and about 3 inches; between about 3 inches and about 4 inches; between about 4 inches and about 5 inches; between about 5 inches and about 6 inches; between about 6 inches and about 7 inches; between about 7 inches and about 8 inches; between about 8 inches and about 9 inches; between about 9 inches and about 10 inches; between about 10 inches and about 11 inches; between about 11 inches and about 12 inches; between about 12 inches and about 13 inches; between about 13 inches and about 14 inches; between about 14 inches and about 15 inches; between about 15 inches and about 16 inches; between about 16 inches and about 17 inches; between about 17 inches and about 18 inches; between about 18 inches and about 19 inches; between about 19 inches and about 20 inches; between about 20 inches and about 21 inches; between about 21 inches and about 22 inches; between about 22 inches and about 23 inches; between about 23 inches and about 24 inches; between about 24 inches and about 25 inches; between about 25 inches and about 26 inches; between about 26 inches and about 27 inches; between about 27 inches and about 28 inches; between about 28 inches and about 29 inches; between about 29 inches and about 30 inches; between about 30 inches and about 31 inches; between about 31 inches and about 32 inches; between about 32 inches and about 33 inches; between about 33 inches and about 34 inches; between about 34 inches and about 35 inches; between about 35 inches and about 36 inches; between about 36 inches and about 37 inches; between about 37 inches and about 38 inches; between about 38 inches and about 39 inches; or, between about 39 inches and about 40 inches; between about 38 inches and about 39 inches; between about 39 inches and about 40 inches; between about 40 inches and about 50 inches; between about 50 inches and about 60 inches; between about 60 inches and about 70 inches; between about 70 inches and about 80 inches; between about 80 inches and about 90 inches; between about 90 inches and about 100 inches; between about 100 inches and about 125 inches; between about 125 inches and about 150 inches; or, between about 150 inches and about 200 inches.

FIG. 15 describes an Insect Production Superstructure System (IPSS) that insect feeding module (2000) provides insects contained therein to be able to Insect Mobility Large scale insect production systems must be designed responsibly to make sure that the insects are freed from hunger, thirst, discomfort, pain, injury, disease, fear and distress. Three feeding chambers (FC1, FC2, FC3) are shown in FIG. 15 and the egg-laying insects present therein may freely travel from one feeding chamber to another.

The plurality of feeding chambers and a passageways therebetween encourage egg-laying insects therein to express normal behavior by enabling mobility and relocation to a more suitable living environment. An insect may decide to up and relocate for any reason it chooses or no reason at all. In the event that one breeding chamber lacks sufficient amounts of enhanced feedstock, or is over-crowded, or contains diseased or cannibalistic insects, the insects may relocate to another feeding chamber to alleviate their discomfort, pain, injury, disease, and fear and distress.

FIG. 15 describes a portion of an Insect Production Superstructure System (IPSS) that permits insects to have mobility and the opportunity to choose between different possible courses of action. Herein are disclosed advancements and better solutions that meet new requirements, unarticulated needs, or existing market needs in maximizing insect welfare, maximizing insect output on a minimal physical outlay, and benefit of large groups of people a high-value animal protein.

The first feeding chamber (FC1) is connected to the second feeding chamber (FC2) via a chamber 2 to chamber 1 transfer line (TL21). The first feeding chamber (FC1) is also connected to the third feeding chamber (FC3) via a chamber 3 to chamber 1 transfer line (TL31). The first feeding chamber (FC1) is also connected to the any one of a plurality of breeding chambers (BC, BC1, BC2. BC3) via a chamber 1 breeding chamber transfer line (TLBC1) which is elaborated upon more in FIGS. 16 and 17.

The second feeding chamber (FC2) is connected to the first feeding chamber (FC1) via a chamber 1 to chamber 2 transfer line (TL12). The second feeding chamber (FC2) is also connected to the third feeding chamber (FC3) via a chamber 3 to chamber 2 transfer line (TL32). The second feeding chamber (FC2) is also connected to the any one of a plurality of breeding chambers (BC, BC1, BC2. BC3) via a chamber 2 breeding chamber transfer line (TLBC2) which is elaborated upon more in FIGS. 16 and 17.

The third feeding chamber (FC3) is connected to the first feeding chamber (FC1) via a chamber 1 to chamber 3 transfer line (TL13). The third feeding chamber (FC3) is also connected to the second feeding chamber (FC2) via a chamber 2 to chamber 3 transfer line (TL23). The third feeding chamber (FC3) is also connected to the any one of a plurality of breeding chambers (BC, BC1, BC2. BC3) via a chamber 3 breeding chamber transfer line (TLBC3) which is elaborated upon more in FIGS. 16 and 17.

Insect Evacuation

The insect evacuation module (3000) is configured to pull a vacuum on each one of the plurality of insect feeding chambers at any given time to evacuate the insects contained therein. A computer (COMP) may be programmed to control the operation of the insect evacuation module (3000) to be able to systematically apply a vacuum on any one separate or individually of either of the first feeding chamber (FC1), second feeding chamber (FC2), or third feeding chamber (FC3).

The level of the vacuum by the insect evacuation fan (312) may vary. Alternatively, instead of a fan, a vacuum pump, steam jet ejector, pneumatic vacuum, eductor, or any conceivable vacuuming means to realize the end to pull a vacuum on any number of plurality of feeding chambers (FC1, FC2, FC3) at any given time may be used. At times, it is important to be able to only draw a vacuum on only one of the feeding chambers at any given time depending upon how far along in the insect growth stage any given feeding chamber (FC1, FC2, FC3) is at For example, by measuring the pressure drop across each of the network of cells contained within any given feeding chamber (FC1, FC2, FC3), it may be determined that it is desirable to only evacuated the insects from say, for example, feeding chamber 1 (FC1) while leaving the other two feeding chambers (FC2, FC3) to remain unchanged to promote stable insect growth. To achieve this end, the computer (COMP) will send a signal (XV1) to only the feeding chamber 1 evacuation valve (VV1) on the first feeding chamber (FC1) to evacuate the contents therein.

A common insect evacuation pressure sensor (PT10) is installed on the common entry conduit (CEC), or alternatively may be installed on any plurality number of separators (S1, S1, S3). The common insect evacuation pressure sensor (PT10) is configured to input a signal (XT10) to the computer (COMP). A common insect evacuation vent line (VRL) is connected at one end to the common entry conduit (CEC) and connected at another end to a header vacuum vent valve (VV0). The header vacuum vent valve (VV0) is interposed on the common insect evacuation vent line (VRL) and is in fluid communication with both the insect evacuation fan (312) and each one of the plurality of insect feeding chambers (FC1, FC2, FC3). The header vacuum vent valve (VV0) is equipped with a controller (CV0) that is configured to input and output a signal (XV0) to the computer (COMP). At least one common insect evacuation line reducer (VR0) is interposed on the common insect evacuation vent line (VRL).

The header vacuum vent valve (VV0) is configured to be able to control the level of vacuum pulled on a feeding chamber (FC1, FC2, FC3). In the event that a deep vacuum needs to be pulled to evacuate a feeding chamber that has reached its maximum or desired insect capacity, the header vacuum vent valve (VV0) may be operatively included in a control loop while integrated with (i) the common insect evacuation pressure sensor (PT10), and (ii) the controller (316) of the fan motor (314) of the insect evacuation fan (312). For example, if a deep vacuum needs to be pulled on, say feeding chamber 1 (FC1), while leaving the other feeding chambers unchanged, the header vacuum vent valve (VV0) may remain in the closed position to permit the insect evacuation fan (312) to completely draw down the pressure in the feeding chamber 1 (FC1) to pull an insect and gas mixture having an insect portion and a gas portion through the first feeding chamber insect evacuation output (205A) and common entry conduit (CEC). If the header vacuum vent valve (VV0) is then opened, or modulated, by any given percentage, it will increase the gas portion of the insect and gas mixture flowing into the separator (300) and thus increase the pressure in the feeding chamber (FC1) since not as deep of a vacuum will be pulled on the feeding chamber (FC1). A header vacuum vent valve (VV0) may be able to aide in the separation of insects and gas within any plurality of separators (S1, S2, S3) contained within the insect evacuation module (3000) by providing a predictable and consistent inlet velocity at the inlet of any number of any give plurality of separators (S1, S2, S3).

In embodiments, the egg-laying insects may be evacuated from any plurality of feeding chambers (FC1, FC2, FC3) by applying a vacuum with a velocity pressure range from: between about 0.001 inches of water to about 0.002 inches of water; between about 0.002 inches of water to about 0.003 inches of water; between about 0.003 inches of water to about 0.006 inches of water; between about 0.006 inches of water to about 0.012 inches of water; between about 0.012 inches of water to about 0.024 inches of water; between about 0.024 inches of water to about 0.050 inches of water; between about 0.050 inches of water to about 0.075 inches of water; between about 0.075 inches of water to about 0.150 inches of water; between about 0.150 inches of water to about 0.300 inches of water; between about 0.300 inches of water to about 0.450 inches of water; between about 0.450 inches of water to about 0.473 inches of water; between about 0.473 inches of water to about 0.496 inches of water; between about 0.496 inches of water to about 0.521 inches of water; between about 0.521 inches of water to about 0.547 inches of water; between about 0.547 inches of water to about 0.574 inches of water; between about 0.574 inches of water to about 0.603 inches of water; between about 0.603 inches of water to about 0.633 inches of water; between about 0.633 inches of water to about 0.665 inches of water; between about 0.665 inches of water to about 0.698 inches of water; between about 0.698 inches of water to about 0.733 inches of water; between about 0.733 inches of water to about 0.770 inches of water; between about 0.770 inches of water to about 0.808 inches of water; between about 0.808 inches of water to about 0.849 inches of water; between about 0.849 inches of water to about 0.891 inches of water; between about 0.891 inches of water to about 0.936 inches of water; between about 0.936 inches of water to about 0.982 inches of water; between about 0.982 inches of water to about 1.031 inches of water; between about 1.031 inches of water to about 1.083 inches of water; between about 1.083 inches of water to about 1.137 inches of water; between about 1.137 inches of water to about 1.194 inches of water; between about 1.194 inches of water to about 1.254 inches of water; between about 1.254 inches of water to about 1.316 inches of water; between about 1.316 inches of water to about 1.382 inches of water; between about 1.382 inches of water to about 1.451 inches of water; between about 1.451 inches of water to about 1.524 inches of water; between about 1.524 inches of water to about 2.286 inches of water; between about 2.286 inches of water to about 3.429 inches of water; between about 3.429 inches of water to about 5.143 inches of water; between about 5.143 inches of water to about 7.715 inches of water; between about 7.715 inches of water to about 11.572 inches of water; between about 11.572 inches of water to about 17.358 inches of water; between about 17.358 inches of water to about 26.037 inches of water; between about 26.037 inches of water to about 39.055 inches of water; between about 39.055 inches of water to about 58.582 inches of water; between about 58.582 inches of water to about 87.873 inches of water; between about 87.873 inches of water to about 131.810 inches of water; between about 131.810 inches of water to about 197.715 inches of water; between about 197.715 inches of water to about 296.573 inches of water; or, between about 296.573 inches of water to about 400 inches of water.

In embodiments, the egg-laying insects may be evacuated from any plurality of feeding chambers (FC1, FC2, FC3) by applying a velocity from: between about 0.05 feet per second to between about 0.10 feet per second; 0.10 feet per second to between about 0.15 feet per second; 0.15 feet per second to between about 0.25 feet per second; 0.25 feet per second to between about 0.40 feet per second; 0.40 feet per second to between about 0.65 feet per second; 0.65 feet per second to between about 1.05 feet per second; 1.05 feet per second to between about 1.70 feet per second; 1.70 feet per second to between about 2.75 feet per second; 2.75 feet per second to between about 3.09 feet per second; 3.09 feet per second to between about 3.64 feet per second; 3.64 feet per second to between about 4.26 feet per second; 4.26 feet per second to between about 4.99 feet per second; 4.99 feet per second to between about 5.84 feet per second; 5.84 feet per second to between about 6.83 feet per second; 6.83 feet per second to between about 8.00 feet per second; 8.00 feet per second to between about 9.37 feet per second; 9.37 feet per second to between about 10.97 feet per second; 10.97 feet per second to between about 12.84 feet per second; 12.84 feet per second to between about 15.04 feet per second; 15.04 feet per second to between about 17.61 feet per second; 17.61 feet per second to between about 20.61 feet per second; 20.61 feet per second to between about 24.14 feet per second; 24.14 feet per second to between about 28.26 feet per second; 28.26 feet per second to between about 33.08 feet per second; 33.08 feet per second to between about 38.74 feet per second; 38.74 feet per second to between about 45.35 feet per second; 45.35 feet per second to between about 53.10 feet per second; 53.10 feet per second to between about 62.17 feet per second; 62.17 feet per second to between about 72.79 feet per second; 72.79 feet per second to between about 85.23 feet per second; 85.23 feet per second to between about 99.78 feet per second; 99.78 feet per second to between about 116.83 feet per second; 116.83 feet per second to between about 136.79 feet per second; 136.79 feet per second to between about 160.15 feet per second; 160.15 feet per second to between about 187.51 feet per second; 187.51 feet per second to between about 219.54 feet per second; 219.54 feet per second to between about 257.04 feet per second; 257.04 feet per second to between about 300.95 feet per second; 300.95 feet per second to between about 352.36 feet per second; 352.36 feet per second to between about 412.55 feet per second; 412.55 feet per second to between about 483.02 feet per second; 483.02 feet per second to between about 565.53 feet per second; 565.53 feet per second to between about 662.13 feet per second; 662.13 feet per second to between about 775.24 feet per second; 775.24 feet per second to between about 907.66 feet per second; 907.66 feet per second to between about 1062.71 feet per second; 1062.71 feet per second to between about 1244.24 feet per second; 1244.24 feet per second to between about 1456.78 feet per second; or, 1456.78 feet per second to between about 1500.00 feet per second.

FIG. 16

FIG. 16 shows a simplistic diagram illustrating a plurality of separators (S1, S2, S3) integrated with one common feeding chamber (FC1), and wherein the feeding chamber (FC1) and second separator (S2) are in fluid communication with one common breeding chamber (BC), and wherein the breeding chamber (BC) is in fluid communication with one common breeding material and insect separator (SEP1A), and wherein the breeding material and insect separator (SEP1A) is in fluid communication with at least one of a plurality of feeding chambers (FC1, FC2, FC3).

FIG. 16 shows a simplistic diagram illustrating a plurality of separators (S1, S2, S3) integrated with one common feeding chamber (FC1), and wherein the feeding chamber (FC1) and second separator (S2) are in fluid communication with one common breeding chamber (BC), and wherein the breeding chamber (BC) is in fluid communication with one common breeding material and insect separator (SEP1A), and wherein the breeding material and insect separator (SEP1A) is in fluid communication with at least one of a plurality of feeding chambers (FC1, FC2, FC3).

FIG. 16 shows a portion of the Insect Production Superstructure System (IPSS) including an insect feeding module (2000), an insect evacuation module (3000), an insect breeding module (4000), and hatched insect separation module (5000). The insect feeding module (2000) is configured to feed the enhanced feedstock from the enhanced feedstock mixing module (1000) and grow insects so that egg-laying insects may in turn lay eggs. The insect evacuation module (3000) is configured to remove insects, residual enhanced feedstock, particulates including insect exoskeleton from the any of a plurality of insect feeding modules (2000, 2000A, 200B, 2000C). The insect breeding module (4000) is configured to remove eggs from the insect feeding module (2000) for incubation over a temperature and humidity controlled duration of time to form hatched-insects. The hatched insect separation module (5000) is configured to separate the hatched-insects and breeding material from the insect breeding module (4000) and then distribute the separated breeding material to any one of the plurality of the insect feeding modules (2000, 2000A, 2000B, 2000C)

FIG. 16 shows an insect feeding module (2000) including one feeding chamber (FC1) integrated with an insect evacuation module (3000) comprised of a first separator (S1), second separator (S2), and a third separator (S3). FIG. 16 shows the first separator (S1) and second separator (S2) as cyclones. FIG. 16 also shows the third separator (S3) as a filter. It is to be noted that the embodiment of FIG. 16 is non-limiting and shall not be construed to limit the disclosure in any way. Any number of separators (S1, S2, S3) may be employed and any permutation or combination of separation unit operations or devices may be used so long as insect portion (304A) is separated from a gas portion (304B) of an insect and gas mixture (304).

FIG. 16 shows the first separator (S1) as a first insect coarse separator (S1A), the second separator (S2) as a second insect fine separator (S2A), and the third separator (S3) as a particulate separator (S3A). The first insect coarse separator (S1A) is configured to remove a portion of the insect portion (304A) separated from the gas portion (304B) of an insect and gas mixture (304). The second insect fine separator (S2A) is configured to remove insects smaller than the insects separated in the first insect coarse separator (S1A). The particulate separator (S3A) is configured to remove particulates such as remnants of enhanced feedstock, or fine polymer particulate, for example, not only including pieces of portions of insect exoskeleton. The particulate separator (S3A) is in fluid communication with the polymer distribution module (1D) and is configured to transfer a portion of the separated particulate to the polymer tank (1D2) as polymer (1D1).

First Separator (S1), First Insect Coarse Separator (S1A)

The first insect coarse separator (S1A) has a first insect coarse separator input (S1A1) that is in fluid communication with the first feeding chamber insect evacuation output (205A) of the first feeding chamber (FC1) via a first feeding chamber exit conduit (302A). The first insect coarse separator (S1A) is configured to accept an insect and gas mixture (304) from the first feeding chamber (FC1), separate a portion of the insects from the gas and output a first insect-depleted gas stream (355) via a coarse separator gas and insect mixture output (356).

The first separator (S1) is equipped with a first dipleg (357), a first separator conveyor (358), and a first separator valve (361) interposed on the first dipleg (357). A first separated insect stream (360) is routed down the first dipleg (357), through the first separator valve (361) and into the first separator conveyor (358). In embodiments, the first separator conveyor (358) is a compression screw (359) which serves to instantly kill insects by compressing them. The first separated insect stream (360) may in turn be sent to a grinder (1250) within an insect grinding module via a first separated insect stream input (371). In other embodiments, the first separated insect stream (360) may be sent to a pathogen removal unit (1550) within a pathogen removal module, or to a within a lipid extraction unit (1501) lipid extraction module.

Second Separator (S2), Second Insect Fine Separator (S2A)

The second insect fine separator (S2A) has a second insect fine separator input (S2A1) that is in fluid communication with the coarse separator gas and insect mixture output (356) of the first insect coarse separator (S1A). The second insect fine separator (S2A) is configured to accept a first insect-depleted gas stream (355) from the first insect coarse separator (S1A), separate a portion of the insects from the gas and output a second insect-depleted gas stream (362) via a fine separator gas and particulate mixture output (363).

The second separator (S2) is equipped with a second dipleg (364), a second separator conveyor (365), and a second separator valve (368) interposed on the second dipleg (364). A second separated insect stream (360) is routed down the second dipleg (364), through the second separator valve (368) and into the second separator conveyor (365). In embodiments, the second separator conveyor (365) is a compression screw (366) which serves to instantly kill insects by compressing them.

In embodiments, the second separator conveyor (365) is a not a compression screw (366) but instead routes the second separated insect stream (367) to the to a breeding chamber (BC) via a breeding chamber fine separated insect portion input (375). In embodiments, the second separator conveyor (365) is a not a compression screw (366) but instead routes the second separated insect stream (367) to a plurality of other destinations such as to the grinder (1250), pathogen removal unit (1550), or lipid extraction unit (1501). The second separated insect stream (367) may be sent to a grinder (1250) within an insect grinding module via a first separated insect stream input (371). In other embodiments, the second separated insect stream (367) may be sent to a pathogen removal unit (1550) within a pathogen removal module, or to a within a lipid extraction unit (1501) lipid extraction module.

Third Separator (S3), Particulate Separator (S3A)

The particulate separator (S3A) has a particulate separator input (S3A1) that is in fluid communication with the fine separator gas and particulate mixture output (363) of the second insect fine separator (S2A). The particulate separator (S3A) is configured to accept a second insect-depleted gas stream (362) from the second insect fine separator (S2A), separate a portion of the particulates from the gas and output a particulate-depleted gas stream (369) to the insect evacuation fan (312).

The insect evacuation fan (312) is in fluid with the breeding chamber (BC) via a breeding chamber exhaust input (376) and is configured to discharge the exhaust (377) into the breeding chamber (BC). In embodiments, the separated insect conveyor (328) of the third separator (S3) particulate separator (S3A) is in fluid communication with the polymer distribution module (1D) and is configured to transfer a portion of the separated particulate stream (370) to the polymer tank (1D2) as polymer (1D1).

Insect Breeding Module (4000)

FIG. 16 shows the insect feeding module (2000) integrated with the insect breeding module (4000). The insect breeding module (4000) is configured to remove eggs from the insect feeding module (2000) for incubation over a temperature and humidity controlled duration of time to form hatched-insects.

The insect breeding module (4000) contains a breeding chamber (BC). FIG. 16 shows one breeding chamber (BC) portrayed as breeding chamber 1 (BC1). It is to be noted that FIG. 16 shows a first feeding chamber (FC1) connected to a breeding chamber 1 (BC1) via a feeding chamber 1 egg-laden breeding material transfer line (R1).

The feeding chamber 1 egg-laden breeding material transfer line (R1) is connected at one end to the first feeding chamber (FC1) via a conveyor output (249) and at another end to breeding chamber 1 (BC1) via a feeding chamber 1 breeding chamber 1 input (BC1A). The feeding chamber 1 egg-laden breeding material transfer line (R1) is configured to transfer an egg-laden breeding material (250) to the interior (BCIN) of breeding chamber 1 (BC1). In embodiments, the interior (BCIN) of the breeding chamber 1 (BC1) contains a tiered plurality of conveyors that include at least an upper and a lower conveyor wherein egg-laden breeding material (250) is transferred from conveyors spaced apart from one another in a vertical orientation to permit sufficient time to incubate the eggs contained within the egg-laden breeding material (250) to hatch insects.

FIG. 16 shows egg-laden breeding material (250) being transferred to the interior (BCIN) of the breeding chamber 1 (BC1) where it is first elevated via a first conveyor transfer unit (XY1A) to the first conveyor height (CH1A) of a first conveyor (CY1A) operating in a clockwise motion of operation.

The first conveyor (CY1A) is positioned at a vertical height above at least one other conveyor. FIG. 16 shows seven conveyors (CY1A, CY2A, CY3A, CY4A, CY5A, CY6A, CY7A) and the first conveyor (CY1A) is positioned at a vertical height above each one of a second conveyor (CY2A), third conveyor (CY3A), fourth conveyor (CY4A), fifth conveyor (CY5A), sixth conveyor (CY6A), and seventh conveyor (CY7A). The second conveyor (CY2A) is positioned at a vertical height above each one of a third conveyor (CY3A), fourth conveyor (CY4A), fifth conveyor (CY5A), sixth conveyor (CY6A), and seventh conveyor (CY7A). The third conveyor (CY3A) is positioned at a vertical height above each one of a fourth conveyor (CY4A), fifth conveyor (CY5A), sixth conveyor (CY6A), and seventh conveyor (CY7A). The fourth conveyor (CY4A) is positioned at a vertical height above each one of a fifth conveyor (CY5A), sixth conveyor (CY6A), and seventh conveyor (CY7A). The fifth conveyor (CY5A) is positioned at a vertical height above each one of a sixth conveyor (CY6A), and seventh conveyor (CY7A). The sixth conveyor (CY6A) is positioned at a vertical height above the seventh conveyor (CY7A).

The first conveyor (CY1A) is installed at a first conveyor height (CH1A) above the second conveyor (CY2A). The second conveyor (CY2A) is installed at a second conveyor height (CH2A) above the third conveyor (CY3A). The third conveyor (CY3A) is installed at a third conveyor height (CH3A) above the fourth conveyor (CY4A). The fourth conveyor (CY4A) is installed at a fourth conveyor height (CH4A) above the fifth conveyor (CY5A). The fifth conveyor (CY5A) is installed at a fifth conveyor height (CH5A) above the sixth conveyor (CY6A). The sixth conveyor (CY6A) is installed at a sixth conveyor height (CH6A) above the seventh conveyor (CY7A).

The seventh conveyor (CY7A) is installed at a seventh conveyor height (CH7A) below all other conveyors (CY1A, CY2A, CY3A, CY4A, CY5A, CY6A). FIG. 16 shows the first conveyor (CY1A), third conveyor (CY3A), fifth conveyor (CY5A), seventh conveyor (CY7A) all configured to operate in a clockwise motion of operation. FIG. 16 shows the second conveyor (CY2A), fourth conveyor (CY4A), sixth conveyor (CY6A), all configured to operate in a counter-clockwise motion of operation.

A conveyor 1 to conveyor 2 transfer unit (XY2A) is configured to transfer the egg-laden breeding material from the first conveyor (CY1A) to the second conveyor (CY2A). The conveyor 2 to conveyor 3 transfer unit (XY3A) is configured to transfer the egg-laden breeding material from the second conveyor (CY2A) to the third conveyor (CY3A). The conveyor 3 to conveyor 4 transfer unit (XY4A) is configured to transfer the egg-laden breeding material from the third conveyor (CY3A) to the fourth conveyor (CY4A). The conveyor 4 to conveyor 5 transfer unit (XY5A) is configured to transfer the egg-laden breeding material from the fourth conveyor (CY4A) to the fifth conveyor (CY5A). The conveyor 5 to conveyor 6 transfer unit (XY6A) is configured to transfer the egg-laden breeding material, and perhaps hatched insects, from the fifth conveyor (CY5A) to the sixth conveyor (CY6A). The conveyor 6 to conveyor 7 transfer unit (XY7A) is configured to transfer the egg-laden breeding material, and perhaps hatched insects, from the sixth conveyor (CY6A) to the seventh conveyor (CY7A). The seventh conveyor (CY7A) is configured to transfer the hatched insects and breeding material from the feeding chamber 1 breeding chamber output (BC1B) of the interior (BCIN) of the breeding chamber (BC) to the interior (SIN1) of the breeding material and insect separator (SEP1A) contained within the hatched insect separation module (5000).

Hatched Insect Separation Module (5000)

FIG. 16 shows the hatched insect separation module (5000) equipped with a breeding material and insect separator (SEP1A) and a breeding material tank (500). The breeding material and insect separator (SEP1A) includes an interior (SIN1), a separator input (1SEPA), a separator material output (1SEPB), and a separator insect output (1SEPC). The breeding material and insect separator (SEP1A) is connected to breeding chamber 1 (BC1) via a breeding chamber 1 hatched egg and breeding material transfer line (U1). The breeding chamber 1 hatched egg and breeding material transfer line (U1) is connected at one end to the breeding chamber 1 (BC1) via a feeding chamber 1 breeding chamber output (BC1B) and connected at another end to the breeding material and insect separator (SEP1A) via a separator input (1SEPA).

The separator input (1SEPA) is configured to accept hatched insects and breeding material from the seventh conveyor (CY7A) of breeding chamber 1 (BC1), and separate hatched insects (400) from the breeding material (523). The separator insect output (1SEPC) is configured to discharge hatched insects (400) from the interior (SIN1) of the breeding material and insect separator (SEP1A) and route the hatched insects (400) to either one of a plurality of feeding chambers (FC1, FC2, FC3) via a separator hatched insect transfer line (O1). Specifically, separator insect output (1SEPC) is configured to discharge hatched insects (400) first feeding chamber (FC1) via a separator feeding chamber 1 transfer line (O11), or to the second feeding chamber (FC2) via a separator feeding chamber 2 transfer line (O12), or to the third feeding chamber (FC3) via a separator feeding chamber 3 transfer line (O13). Hatched insects (400) transferred from the hatched insect separation module (5000) to the insect feeding module (2000) are made available to the first feeding chamber (FC1) via a separator feeding chamber 1 transfer line (O11) and a chamber 1 breeding chamber transfer line (TLBC1).

Breeding material (523) separated from the hatched insects (400) within the interior (SIN1) of the breeding material and insect separator (SEP1A) is routed to the interior (501) of a breeding material tank (500) via a separator material output (1SEPB). The breeding material (523) separated from the hatched insects (400) within the interior (SIN1) of the breeding material and insect separator (SEP1A) may be characterized as an egg-depleted material (518) since eggs were incubated to form hatched insects (400). A material transfer line (522) is connected at one end to the separator material output (1SEPB) of the breeding material and insect separator (SEP1A) and connected at another end to the breeding material input (502) of the breeding material tank (500). An egg-depleted material transfer conveyor (519) may be interposed in the material transfer line (522) in between the breeding material and insect separator (SEP1A) and the breeding material tank (500).

The breeding material tank (500) has an interior (501), a breeding material input (502), and a breeding material output (510). The breeding material tank (500) also has a top section (503), a bottom section (506), and an interior (501) defined by at least one side wall (507). A breeding material screw conveyor (508) is located at the bottom section (506) and configured to transfer breeding material to either one of a plurality of feeding chambers (FC1, FC2, FC3) via a breeding material transfer line (511). The breeding material transfer line (511) is connected at one end to any one of a plurality of feeding chambers (FC1, FC2, FC3) and connected at another end to the breeding material screw conveyor (508) via a breeding material output (510). The breeding material screw conveyor (508) is equipped with a breeding material screw conveyor motor (512), controller (513), and is configured to input and output a signal (514) to the computer (COMP).

FIG. 17

FIG. 17 shows a perspective view of one embodiment of a scalable portable modular Insect Production Superstructure System (IPSS) designed with: one enhanced feedstock mixing module (1000); three insect feeding modules (2000A, 2000B, 2000C); one insect evacuation module (3000); three insect breeding modules (4000A, 4000B, 4000C), and three insect separation modules (5000).

FIG. 17 shows a perspective view of one embodiment of a scalable portable modular Insect Production Superstructure System (IPSS) designed with: one enhanced feedstock mixing module (1000); three insect feeding modules (2000A, 2000B, 2000C); one insect evacuation module (3000); three insect breeding modules (4000A, 4000B, 4000C), and three insect separation modules (5000).

In one embodiment, each module (1000, 2000A, 2000B, 2000C, 3000, 4000A, 4000B, 4000C, 5000) container is a 40 feet high cube container conforming to the International Organization for Standardization (ISO) specifications. In another embodiment, the container may measure 40 feet×8 feet×9.6 feet. In another embodiment, other containers of different sizes may be used.

In embodiments, each module (1000, 2000A, 2000B, 2000C, 3000, 4000A, 4000B, 4000C, 5000) may be positioned on high density plastic ties (HDT). The high density plastic ties (HDT) provide stability to the module (1000, 2000A, 2000B, 2000C, 3000, 4000A, 4000B, 4000C, 5000) of the Insect Production Superstructure System (IPSS) and may be cheaper and faster to install than traditional concrete foundations. In another embodiment, each of the module (1000, 2000A, 2000B, 2000C, 3000, 4000A, 4000B, 4000C, 5000) may be positioned on concrete foundations. Electrical cables may be contained in a plurality of fiberglass cable trays (FGT) placed between each module (1000, 2000A, 2000B, 2000C, 3000, 4000A, 4000B, 4000C, 5000).

The embodiment of FIG. 17 shows the enhanced feedstock mixing module (1000) including a feedstock distribution module (1A), mineral distribution module (1B), vitamin distribution module (1C), polymer distribution module (1D), water distribution module (1E), and enhanced feedstock distribution module (1F), However, as depicted in FIGS. 18-20 the water distribution module (1E) and enhanced feedstock distribution module (1F) may be separate from the enhanced feedstock mixing module (1000). A separate water distribution module (1E) and a separate enhanced feedstock distribution module (1F) are not shown in FIG. 17 because it these modules (1E, 1F) are designed to be housed within the enhanced feedstock mixing module (1000). A separate water distribution module (1E) is shown in FIGS. 21-23. A separate and a separate enhanced feedstock distribution module (1F) is shown in FIGS. 24-26.

In the non-limiting example of FIG. 17 for a variable-scale, modular, easily manufacturable, energy efficient, reliable, and computer operated Insect Production Superstructure Systems (IPSS) shows one enhanced feedstock mixing module (1000) in fluid communication with a first insect feeding module (2000A), second insect feeding module (2000B), and a third insect feeding module (2000C).

A first enhanced feedstock stream (EF1) is configured to pass from the enhanced feedstock mixing module (1000) to the first insect feeding module (2000A). A second enhanced feedstock stream (EF2) is configured to pass from the enhanced feedstock mixing module (1000) to the second insect feeding module (2000B). A third enhanced feedstock stream (EF3) is configured to pass from the enhanced feedstock mixing module (1000) to the third insect feeding module (2000C).

Each of the first insect feeding module (2000A), second insect feeding module (2000B), third insect feeding module (2000C), are connected to one common insect evacuation module (3000) via a common entry conduit (CEC). The common entry conduit (CEC) is connected at one end to the insect evacuation module (3000) and connected at one end to the first insect feeding module (2000A) via a first feeding chamber insect evacuation output (205A). The common entry conduit (CEC) is connected at one end to the insect evacuation module (3000) and connected at one end to the second insect feeding module (2000B) via a second feeding chamber insect evacuation output (205B). The common entry conduit (CEC) is connected at one end to the insect evacuation module (3000) and connected at one end to the third insect feeding module (2000C) via a third feeding chamber insect evacuation output (205C). Each insect feeding module (2000A, 2000B, 2000C) is connected to its own insect breeding module (4000A, 4000B, 4000C). The first insect feeding module (2000A) is connected to the first insect breeding module (4000A) via a feeding chamber 1 egg-laden breeding material transfer line (R1). The second insect feeding module (2000B) is connected to the second insect breeding module (4000B) via a feeding chamber 2 egg-laden breeding material transfer line (R2). The third insect feeding module (2000C) is connected to the third insect breeding module (4000C) via a feeding chamber 3 egg-laden breeding material transfer line (R3).

Each insect breeding module (4000A, 4000B, 4000C) is connected to its own hatched insect separation module (5000A, 5000B, 5000C). The first insect breeding module (4000A) is connected to the first hatched insect separation module (5000A) via a breeding chamber 1 hatched egg and breeding material transfer line (U1). The second insect breeding module (4000B) is connected to the second hatched insect separation module (5000B) via a breeding chamber 2 hatched egg and breeding material transfer line (U2). The third insect breeding module (4000C) is connected to the third hatched insect separation module (5000C) via a breeding chamber 3 hatched egg and breeding material transfer line (U3).

Each hatched insect separation module (5000A, 5000B, 5000C) is connected to any of the plurality of insect feeding modules (2000A, 2000B, 2000C) via a first hatched insect output (DFC), second hatched insect output (EFC), and third hatched insect output (FFC). The first hatched insect output (DFC) of the first hatched insect separation module (5000A) is in fluid communication with the first insect feeding module (2000A) via a first hatched insect input (AFC). The first hatched insect output (DFC) of the first hatched insect separation module (5000A) is in fluid communication with the second insect feeding module (2000B) via a second hatched insect input (BFC). The first hatched insect output (DFC) of the first hatched insect separation module (5000A) is in fluid communication with the third insect feeding module (2000C) via a third hatched insect input (CFC).

The second hatched insect output (EFC) of the second hatched insect separation module (5000B) is in fluid communication with the first insect feeding module (2000A) via a first hatched insect input (AFC). The second hatched insect output (EFC) of the second hatched insect separation module (5000B) is in fluid communication with the second insect feeding module (2000B) via a second hatched insect input (BFC). The second hatched insect output (EFC) of the second hatched insect separation module (5000B) is in fluid communication with the third insect feeding module (2000C) via a third hatched insect input (CFC).

The third hatched insect output (FFC) of the third hatched insect separation module (5000C) is in fluid communication with the first insect feeding module (2000A) via a first hatched insect input (AFC). The third hatched insect output (FFC) of the third hatched insect separation module (5000C) is in fluid communication with the second insect feeding module (2000B) via a second hatched insect input (BFC). The third hatched insect output (FFC) of the third hatched insect separation module (5000C) is in fluid communication with the third insect feeding module (2000C) via a third hatched insect input (CFC).

FIG. 18

FIG. 18 shows a front view of one embodiment of an enhanced feedstock mixing module (1000) module including a feedstock distribution module (1A), mineral distribution module (1B), vitamin distribution module (1C), and a polymer distribution module (1D). The enhanced feedstock mixing module (1000) is shown to be contained within a 40 feet high cube container conforming to the International Organization for Standardization (ISO) specifications.

The feedstock distribution module (1A) has feedstock (1A1) contained within the interior (1A3) of a feedstock tank (1A2). A feedstock mass sensor (1A7) is provided to determine the loss in mass of the feedstock tank (1A2). The feedstock tank (1A2) has a live floor screw (1A21) with a motor (1A22) is configured to transfer feedstock (1A1) from the interior (1A3) of the feedstock tank (1A2) to a feedstock conveyor (1A5) and an enhanced feedstock transport screw (1A20). A supply access door (1A15) is positioned above the feedstock input (1A4) and configured to transfer feedstock (1A1) to the interior (1A3) of the feedstock tank (1A2). A supply access door opening/closing unit (1A16) is operatively coupled to the supply access door (1A15) and a weather seal (1A17) is in contact with the supply access door (1A15) to prevent rain and other elements from entering the enhanced feedstock mixing module (1000).

The mineral distribution module (1B) has minerals (1B1) contained within the interior (1B3) of a mineral tank (1B2). A mineral mass sensor (1B7) is provided to determine the loss in mass of the mineral tank (1B2). The mineral tank (1B2) has a live floor screw (1B20) with a motor (1B21) is configured to transfer minerals (1B1) from the interior (1B3) of the mineral tank (1B2) to a mineral conveyor (1B5) and an enhanced feedstock transport screw (1A20) via an enhanced feedstock transport screw connection (1B18). A supply access door (1B13) is positioned above the mineral input (1B4) and configured to transfer minerals (1B1) to the interior (1B3) of the mineral tank (1B2). A supply access door opening/closing unit (1B14) is operatively coupled to the supply access door (1B13) and a weather seal (1B15) is in contact with the supply access door (1B13) to prevent rain and other elements from entering the enhanced feedstock mixing module (1000).

The vitamin distribution module (1C) has vitamins (1C1) contained within the interior (1C3) of a vitamin tank (1C2). A vitamin mass sensor (1C7) is provided to determine the loss in mass of the vitamin tank (1C2). The vitamin tank (1C2) has a live floor screw (1C20) with a motor (1C21) is configured to transfer vitamins (1C1) from the interior (1C3) of the vitamin tank (1C2) to a vitamin conveyor (1C5) and an enhanced feedstock transport screw (1A20) via an enhanced feedstock transport screw connection (1C18). A supply access door (1C13) is positioned above the vitamin input (1C4) and configured to transfer vitamins (1C1) to the interior (1C3) of the vitamin tank (1C2). A supply access door opening/closing unit (1C14) is operatively coupled to the supply access door (1C13) and a weather seal (1C15) is in contact with the supply access door (1C13) to prevent rain and other elements from entering the enhanced feedstock mixing module (1000).

The polymer distribution module (1D). includes polymer (1D1) contained within the interior (1D3) of a polymer tank (1D2). A polymer mass sensor (1D7) is provided to determine the loss in mass of the polymer tank (1D2). The polymer tank (1D2) has a live floor screw (1D20) with a motor (1D21) is configured to transfer polymer (1D1) from the interior (1D3) of the polymer tank (1D2) to a polymer conveyor (1D5) and an enhanced feedstock transport screw (1A20) via an enhanced feedstock transport screw connection (1D18). A supply access door (1D13) is positioned above the polymer input (1D4) and configured to transfer polymer (1D1) to the interior (1D3) of the polymer tank (1D2). A supply access door opening/closing unit (1C14) is operatively coupled to the supply access door (1C13) and a weather seal (1C15) is in contact with the supply access door (1C13) to prevent rain and other elements from entering the enhanced feedstock mixing module (1000).

A dry enhanced feedstock (DEF) is outputted from the enhanced feedstock mixing module (1000) via the enhanced feedstock transport screw (1A20). A feedstock moisture sensor (1A12A) is interposed on the enhanced feedstock transport screw (1A20) to measure the water content of the dry enhanced feedstock (DEF). Alternately, the feedstock moisture sensor (1A12A) may be positioned on the enhanced feedstock transport screw (1A20) after the minerals (1B1), vitamins (1C1), polymer (1D1) have been mixed with the feedstock (1A1). The enhanced feedstock mixing module (1000) may be equipped with a low voltage disconnect switch (1000LV) and a computer (COMP).

FIG. 19

FIG. 19 shows a top view of one embodiment of an enhanced feedstock mixing module (1000) including a feedstock distribution module (1A), mineral distribution module (1B), vitamin distribution module (1C), and a polymer distribution module (1D).

Feedstock (1A1) within the feedstock tank (1A2), minerals (1B1) within the mineral tank (1B2), vitamins (1C1) within the vitamin tank (1C2), and polymer (1D1) within the polymer tank (1D2) are all mixed together in an enhanced feedstock transport screw (1A20). A live floor screw (1A21) equipped with a motor (1A22) is positioned within the feedstock tank (1A2). The live floor screw (1A21) transfers feedstock (1A1) to a feedstock conveyor (1A5). The feedstock conveyor (1A5) has a feedstock conveyor output (1A6) that is connected to a feedstock transfer line (1A14). The feedstock transfer line (1A14) is connected at one end to the feedstock conveyor output (1A6) and at another end to the enhanced feedstock transport screw (1A20) via an enhanced feedstock transport screw connection (1A20A). The feedstock distribution module (1A) is equipped with an air inlet vent (1A18) that is configured to input air (1A19) to the feedstock distribution module (1A) portion of the enhanced feedstock mixing module (1000). A feedstock module access door (1A23) is provided to access the feedstock distribution module (1A) portion of the enhanced feedstock mixing module (1000).

A live floor screw (1B20) equipped with a motor (1B21) is positioned within the mineral tank (1B2). The live floor screw (1B20) transfers minerals (1B1) to a mineral conveyor (1B5). The mineral conveyor (1B5) has a mineral conveyor output (1B6) that is connected to a mineral transfer line (1B12). The mineral transfer line (1B12) is connected at one end to the mineral conveyor output (1B6) and at another end to the enhanced feedstock transport screw (1A20) via an enhanced feedstock transport screw connection (1B18). The mineral distribution module (1B) is equipped with an air inlet vent (1B16) that is configured to input air (1B17) to the mineral distribution module (1B) portion of the enhanced feedstock mixing module (1000). A mineral module access door (1B22) is provided to access the mineral distribution module (1B) portion of the enhanced feedstock mixing module (1000).

A live floor screw (1C20) equipped with a motor (1C21) is positioned within the vitamin tank (1D2). The live floor screw (1C20) transfers vitamins (1C1) to a vitamin conveyor (1C5). The vitamin conveyor (1C5) has a vitamin conveyor output (1C6) that is connected to a vitamin transfer line (1C12). The vitamin transfer line (1C12) is connected at one end to the vitamin conveyor output (1C6) and at another end to the enhanced feedstock transport screw (1A20) via an enhanced feedstock transport screw connection (1C18). The vitamin distribution module (1C) is equipped with an air inlet vent (1C16) that is configured to input air (1C17) to the vitamin distribution module (1C) portion of the enhanced feedstock mixing module (1000). A vitamin module access door (1C22) is provided to access the vitamin distribution module (1C) portion of the enhanced feedstock mixing module (1000).

A live floor screw (1D20) equipped with a motor (1D21) is positioned within the polymer tank (1D2) to transfer polymer (1D1) to a polymer conveyor (1D5). The polymer conveyor (1D5) has a polymer conveyor output (1D6) that is connected to a polymer transfer line (1D12). The polymer transfer line (1D12) is connected at one end to the polymer conveyor output (1D6) and at another end to the enhanced feedstock transport screw (1A20) via an enhanced feedstock transport screw connection (1D18). The polymer distribution module (1D) is equipped with an air inlet vent (1D16) that is configured to input air (1D17) to the polymer distribution module (1D) portion of the enhanced feedstock mixing module (1000). A polymer module access door (1D22) is provided to access the polymer distribution module (1D) portion of the enhanced feedstock mixing module (1000). The polymer distribution module (1D) is in fluid communication with the third separator (S3) particulate separator (S3A) of the insect evacuation module (3000). The polymer tank (1D2) is configured to accept a polymer (1D1) from a portion of the separated particulate stream (370) of the separated insect conveyor (328) of the third separator (S3) particulate separator (S3A).

FIG. 20

FIG. 20 shows a first side view of one embodiment of an enhanced feedstock mixing module (1000). Visible from the first side view of the enhanced feedstock mixing module (1000) is the supply access door (1A15) that is opened and closed by a supply access door opening/closing unit (1A16) wherein a weather seal (1A17) prevents rain and other elements from entering the enhanced feedstock mixing module (1000).

Feedstock (1A1) is contained within the interior (1A3) of the feedstock tank (1A2). Feedstock (1A1) is added to the enhanced feedstock mixing module (1000) through the supply access door (1A15) where it enters the feedstock input (1A4) and into the interior (1A3) of the feedstock tank (1A2). A live floor screw (1A21) is positioned in the interior (1A3) of the feedstock tank (1A2). The live floor screw (1A21) is configured to transfer feedstock (1A1) from the interior (1A3) of the feedstock tank (1A2) into a feedstock conveyor (1A5). The feedstock conveyor motor (1A9) drives the feedstock conveyor (1A5) to transport feedstock (1A1) through the feedstock conveyor output (1A6) and into the enhanced feedstock transport screw (1A20) via an enhanced feedstock transport screw connection (1A20A). A feedstock mass sensor (1A7) may be positioned on the feedstock conveyor (1A5) to measure the mass loss and control to a pre-determined feedstock mass flow rate into the enhanced feedstock transport screw (1A20). Also visible is the feedstock module access door (1A23) and an air inlet vent (1A18) which permits air (1A19) to enter the feedstock distribution module (1A) portion of the enhanced feedstock mixing module (1000).

FIG. 21

FIG. 21 shows a front view of one embodiment of a water distribution module (1E). The following description for FIG. 21 also applies to FIG. 22 since the reference numerals for FIG. 20 and FIG. 21 are identical. The water distribution module (1E) is shown to be contained within a 40 feet high cube container conforming to the International Organization for Standardization (ISO) specifications.

The water distribution module (1E) contains a first water treatment unit (1E6), second water treatment unit (1E11), water distribution module (1E) enhancer tank (1E45) and a water supply pump (1E22). A water input line (1E4) enters the water distribution module (1E) and is connected to the first water treatment unit (1E6) at a first water treatment unit input (1E7). A first water pressure sensor (1E2) is installed on the water input line (1E4). The first water treatment unit (1E6) may contain a contain an adsorbent, ion-exchange resin, catalyst, or activated carbon.

The first water treatment unit (1E6) is connected to the second water treatment unit (1E11) via a first contaminant-depleted water transfer line (1E10). The first contaminant-depleted water transfer line (1E10) is connected at one end to the first water treatment unit output (1E8) of the first water treatment unit (1E6) and connected at a second end to the second water treatment unit input (1E12) of the second water treatment unit (1E11). The second water treatment unit (1E11) may contain a contain an adsorbent, ion-exchange resin, catalyst, or activated carbon. The system as shown in FIGS. 21-23 may, for example be used to decontaminate water that contains urea. The first water treatment unit (1E6)

contains activated carbon and the second water treatment unit (1E11) contains a molecular sieve adsorbent.

The second water treatment unit (1E11) is connected to the water tank (1E16) via a second contaminant-depleted water transfer line (1E15). The second contaminant-depleted water transfer line (1E15) is connected at one end to the second water treatment unit output (1E13) of the second water treatment unit (1E11) and connected at another end to the water input (1E18) of the water tank (1E16). A water supply valve (1E23) with a controller (1E24) is interposed on the second contaminant-depleted water transfer line (1E15) in between the second water treatment unit (1E11) and water tank (1E16). The water tank (1E16) has an interior (1E17) that contains water (1E1). The water tank (1E16) is equipped with a high water level sensor (1E26) and a low water level sensor (1E28).

Enhancers (1E44) contained within the interior (1E46) of the enhancer tank (1E45) may be routed to the interior (1E17) of the water tank (1E16) through an enhancer transfer line (1E48). The enhancer transfer line (1E48) is connected at one end to the enhancer tank output (1E47) of the enhancer tank (1E45) and connected at another end to the enhancer input (1E49) of the water tank (1E16). A water enhancer supply valve (1E52) with a controller (1E53) is interposed on the enhancer transfer line (1E48) in between the enhancer tank (1E45) and the water tank (1E16). An enhancer flow sensor (1E50) is interposed on the enhancer transfer line (1E48) in between the enhancer tank (1E45) and the water tank (1E16).

A water supply pump (1E22) is connected to the water tank (1E16) via a water discharge line (1E21). The water supply pump (1E22) is configured to remove water (1E1), and enhancers (1E44), from the interior (1E17) of the water tank (1E16) for transfer downstream to be mixed with a dry enhanced feedstock (DEF) to create a wet enhanced feedstock (WEF). The water discharge line (1E21) is connected at one end to the water output (1E20) of the water tank (1E16) and connected at another end to the water supply pump (1E22).

The water supply pump (1E22) pulls a suction on the water discharge line (1E21) of the water tank (1E16) and increases the pressure of the (1E1) and outputs pressurized water via a water transfer line (1E41). The water transfer line (1E41) has a variety of instrumentation installed on it, including: a water flow sensor (1E34); a water control valve (1E36); a third water pressure sensor (1E39); and, a water quality sensor (1E42). A second water pressure sensor (1E30) is installed on the water transfer line (1E41) upstream of the water control valve (1E36) and closer to the water supply pump (1E22). In embodiments, the pressure drop across the water control valve (1E36) may range from: between about 1 pound per square inch to about 5 pound per square inch; between about 5 pound per square inch to about 10 pound per square inch; between about 10 pound per square inch to about 15 pound per square inch; between about 15 pound per square inch to about 20 pound per square inch; between about 25 pound per square inch to about 30 pound per square inch; between about 35 pound per square inch to about 40 pound per square inch; between about 45 pound per square inch to about 50 pound per square inch; between about 55 pound per square inch to about 60 pound per square inch; between about 65 pound per square inch to about 70 pound per square inch; between about 75 pound per square inch to about 80 pound per square inch; between about 85 pound per square inch to about 90 pound per square inch; between about 95 pound per square inch to about 100 pound per square inch; between about 100 pound per square inch to about 125 pound per square inch; between about 125 pound per square inch to about 150 pound per square inch; or, between about 150 pound per square inch to about 200 pound per square inch.

The water transfer line (1E41) is discharged from the water distribution module (1E) en route to the enhanced feedstock distribution module (1F) on FIGS. 24-26. The water distribution module (1E) contains a first access door (1E55) at one end and a second access door (1E56) at another end. The water distribution module (1E) also contains an air vent (1E57) for introduction of an air supply (1E58). The water distribution module (1E) also contains a low voltage disconnect switch (1E59) and a computer (COMP)

FIG. 22

FIG. 22 shows a top view of one embodiment of a water distribution module (1E). Refer to the text in the preceding section for the description of FIG. 22.

FIG. 23

FIG. 23 shows a first side view of one embodiment of a water distribution module (1E). Visible from the first side view of the water distribution module (1E) is the first access door (1E55) along with the air vent (1E57) for introduced on an air supply (1E58). A water input line (1E4) containing is shown entering the first water treatment unit (1E6) via a first water treatment unit input (1E7). Water (1E1) is shown contained within the interior (1E17) of the water tank (1E16). Enhancers (1E44) are shown contained within the interior (1E46) of the enhancer tank (1E45).

FIG. 24

FIG. 24 shows a front view of one embodiment of an enhanced feedstock distribution module (1F). The enhanced feedstock distribution module (1F) is shown to be contained within a 40 feet high cube container conforming to the International Organization for Standardization (ISO) specifications. Water (1E1) enters from the left-hand-side of the enhanced feedstock distribution module (1F) via a water transfer line (1E41). The water (1E1) is mixed with a dry enhanced feedstock (DEF) to form a wet enhanced feedstock (WEF). The dry enhanced feedstock (DEF) enters from the left-hand-side of the enhanced feedstock distribution module (1F) via an enhanced feedstock transport screw (1A20). A wet enhanced feedstock (WEF) is transported to the enhanced feedstock splitter (1F1) via an enhanced feedstock transfer line (1F0). An enhanced feedstock moisture sensor (1A12B) is installed on the enhanced feedstock transfer line (1F0). In embodiments, the wet enhanced feedstock (WEF) may be introduced to the enhanced feedstock splitter (1F1) through an enhanced feedstock transfer line (1F0) via a plurality of inputs (1F3A, 1F3B, 1F3C). Each of the first splitter input (1F3A), second splitter input (1F3B), and third splitter input (1F3C), transfer a wet enhanced feedstock (WEF) to the interior (1F2) of the enhanced feedstock splitter (1F1).

The enhanced feedstock splitter (1F1) has a top section (1F4), bottom section (1F5), and an interior (1F2) defined by at least one side wall (1F6). A first splitter level sensor (1F7) is positioned on the side wall (1F6). The enhanced feedstock splitter (1F1) is shown equipped with a splitter first screw conveyor (1F9) and a splitter second screw conveyor (1F14) both positioned at the bottom section (1F5) of the enhanced feedstock splitter (1F1). The splitter first screw conveyor (1F9) transfers enhanced feedstock from the interior (1F2) of the enhanced feedstock splitter (1F1) to a first weigh screw (1F24) via a first output (1F10). The splitter second screw conveyor (1F14) transfers enhanced feedstock from the interior (1F2) of the enhanced feedstock splitter (1F1) to a second weigh screw (1F33) via a second output (1F15). The enhanced feedstock distribution module (1F) is shown equipped with a low voltage disconnect switch (1F55) and a computer (COMP).

FIG. 25

FIG. 25 shows a top view of one embodiment of an enhanced feedstock distribution module (1F). The enhanced feedstock distribution module (1F) is shown to be contained within a 40 feet high cube container conforming to the International Organization for Standardization (ISO) specifications. Water (1E1) enters from the left-hand-side of the enhanced feedstock distribution module (1F) via a water transfer line (1E41). The water (1E1) is mixed with a dry enhanced feedstock (DEF) to form a wet enhanced feedstock (WEF). The dry enhanced feedstock (DEF) enters from the left-hand-side of the enhanced feedstock distribution module (1F) via an enhanced feedstock transport screw (1A20). A wet enhanced feedstock (WEF) is transported to the enhanced feedstock splitter (1F1) via an enhanced feedstock transfer line (1F0). An enhanced feedstock moisture sensor (1A12B) is installed on the enhanced feedstock transfer line (1F0). In embodiments, the wet enhanced feedstock (WEF) may be introduced to the enhanced feedstock splitter (1F1) through an enhanced feedstock transfer line (1F0) via a plurality of inputs (1F3A, 1F3B, 1F3C). Each of the first splitter input (1F3A), second splitter input (1F3B), and third splitter input (1F3C), transfer a wet enhanced feedstock (WEF) to the interior (1F2) of the enhanced feedstock splitter (1F1).

The enhanced feedstock splitter (1F1) has an interior (1F2) defined by at least one side wall (1F6). A first splitter level sensor (1F7) is positioned on the side wall (1F6). The enhanced feedstock splitter (1F1) is shown equipped with a splitter first screw conveyor (1F9) and a splitter second screw conveyor (1F14) both positioned within the interior (1F2) of the enhanced feedstock splitter (1F1).

The splitter first screw conveyor (1F9) transfers enhanced feedstock from the interior (1F2) of the enhanced feedstock splitter (1F1) to a first weigh screw (1F24) via a first output (1F10). The first weigh screw (1F24) has a first weigh screw input (1F25) and a first weigh screw output (1F26). The first weigh screw input (1F25) of the first weigh screw (1F24) accepts enhanced feedstock from the first output (1F10) of the splitter first screw conveyor (1F9). The splitter first screw conveyor (1F9) is equipped with a splitter first screw conveyor motor (1F11). The first weigh screw (1F24) is configured to discharge a first weighed enhanced feedstock stream (1F32) or a first enhanced feedstock stream (EF1) via the first weigh screw output (1F26). The first weighed enhanced feedstock stream (1F32) or the first enhanced feedstock stream (EF1) is discharged from the first weigh screw output (1F26) where it is then transferred to a first feeding chamber (FC1). The first weigh screw (1F24) is equipped with a mass sensor (1F27) and a first weigh screw motor (1F29).

The splitter second screw conveyor (1F14) transfers enhanced feedstock from the interior (1F2) of the enhanced feedstock splitter (1F1) to a second weigh screw (1F33) via a second output (1F15). The second weigh screw (1F33) has a second weigh screw input (1F34) and a second weigh screw output (1F35). The second weigh screw input (1F34) of the second weigh screw (1F33) accepts enhanced feedstock from the second output (1F15) of the splitter second screw conveyor (1F14). The splitter second screw conveyor (1F14) is equipped with a splitter second screw conveyor motor (1F16). The second weigh screw (1F33) is configured to discharge a second weighed enhanced feedstock stream (1F41) or a second enhanced feedstock stream (EF2) via the second weigh screw output (1F35). The second weighed enhanced feedstock stream (1F41) or the second enhanced feedstock stream (EF2) is discharged from the second weigh screw output (1F35) where it is then transferred to a second feeding chamber (FC2). The second weigh screw (1F33) is equipped with a mass sensor (1F36) and a second weigh screw motor (1F38).

The enhanced feedstock distribution module (1F) is shown equipped with a low voltage disconnect switch (1F55) and a computer (COMP). Also shown is a first access door (1F51), second access door (1F52), and an air vent (1F53) configured to introduce an air supply (1F54) to the enhanced feedstock distribution module (1F).

FIG. 26

FIG. 26 shows a first side view of one embodiment of an enhanced feedstock distribution module (1F). Visible from the first side view of the enhanced feedstock transfer line (1F0) is the first access door (1F51) along with the air vent (1F53) for introduced on an air supply (1F54). The enhanced feedstock splitter (1F1) is shown to have an interior (1F2) defined by at least one side wall (1F6). A first splitter level sensor (1F7) is positioned on the side wall (1F6). The enhanced feedstock splitter (1F1) has a top section (1F4) and a bottom section (1F5). A splitter second screw conveyor (1F14) is positioned within the interior (1F2) of the enhanced feedstock splitter (1F1) at the bottom section (1F5).

A water transfer line (1E41) is shown entering the enhanced feedstock transfer line (1F0) where it mixes with enhanced feedstock and is routed to the interior (1F2) of the enhanced feedstock splitter (1F1) via an enhanced feedstock transfer line (1F0) and a first splitter input (1F3A). The first splitter input (1F3A) has an insertion distance (1F3A1) positioned within the interior (1F2) of the enhanced feedstock splitter (1F1). In embodiments, the insertion distance (1F3A1) may range from: between about 2 inches to about 4 inches; between about 4 inches to about 8 inches; between about 8 inches to about 12 inches; between about 12 inches to about 16 inches; between about 16 inches to about 20 inches; between about 20 inches to about 24 inches; between about 24 inches to about 28 inches; between about 28 inches to about 30 inches; between about 30 inches to about 34 inches; between about 34 inches to about 36 inches; between about 36 inches to about 40 inches; between about 40 inches to about 44 inches; between about 44 inches to about 46 inches; between about 46 inches to about 50 inches; or, between about 50 inches to about 60 inches.

A second output (1F15) is shown at the bottom section (1F5) of the enhanced feedstock splitter (1F1). A second weigh screw (1F33) is shown to have a second weigh screw input (1F34) and a second weigh screw output (1F35). The second weigh screw input (1F34) is connected to the second output (1F15) is shown at the bottom section (1F5) of the enhanced feedstock splitter (1F1). The second weigh screw (1F33) is equipped with a mass sensor (1F36) and a second weigh screw motor (1F38). The second weighed enhanced feedstock stream (1F41) or the second enhanced feedstock stream (EF2) is discharged from the second weigh screw output (1F35) where it is then transferred to a second feeding chamber (FC2).

FIG. 27

FIG. 27 shows a front view of one embodiment of an insect feeding module (2000, 2000A, 2000B, 2000C). Referring to FIGS. 27-29, the insect feeding module (2000, 2000A, 2000B, 2000C) is shown to be contained within a 40 feet high cube container conforming to the International Organization for Standardization (ISO) specifications.

FIG. 27 shows an insect feeding module (2000, 2000A, 2000B, 2000C) containing a network (220) of cells (219) for growing insects (225). The network (220) of cells (219) has openings (222) first end (221) and openings (224) of the second end (223). A vibration unit (214) equipped with a vibration unit motor (215) is operatively connected to the network (220) of cells (219) via a first vibration unit connection (218A) and a second vibration unit connection (218B). The vibration unit (214) is configured to vibrate at least a portion of the network (220) of cells (219) to assist in removal of insects (225) contained therein.

In embodiments, the network (220) of cells (219) has a network length (N-L) that is greater than the network width (N-W). In embodiments, the network (220) of cells (219) has a network length (N-L) that is less than the network width (N-W). In one example, as in the non-limiting embodiments of FIGS. 27-29, the network width (N-W) is approximately about between about 4 feet to about 5 feet, and the network length (N-L) is approximately about between about 30 feet to about 31 feet to fit within the cube container and allowing for access and maintenance.

In embodiments, the network length (N-L) ranges from: 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the network width (N-W) ranges from: 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the interior (201) of the cube container is the interior (201) of the feeding chamber (200). The first side wall (202A) of the feeding chamber (200) is shown spaced apart from the first cube container side wall (CW-A). The second side wall (202B) of the feeding chamber (200) is shown spaced apart from the second cube container side wall (CW-B). The third side wall (202C) of the feeding chamber (200) is shown spaced apart from the third cube container side wall (CW-C). The fourth side wall (202D) of the feeding chamber (200) is shown spaced apart from the fourth cube container side wall (CW-D).

The top (203) of the feeding chamber (200) is shown to be the cube container top wall (CW-T). The first side wall (202A), second side wall (202B), third side wall (202C), fourth side wall (202D), may be flexible, perforated, wire or screen, or the like which is positioned extending into the interior (201) of the feeding chamber from the at a side wall length (SW-L). No screen floor (258) is shown in FIGS. 27-29 instead the bottom (204) of the feeding chamber (200) is open to the surface of the conveyor (255) of the egg transfer system (244).

The first side wall (202A), second side wall (202B), third side wall (202C), and fourth side wall (202D) are spaced apart from the cube container side walls (CW-A, CW-B, CW-C, CW-D) so that the entire interior (201) of the feeding chamber (200) is positioned directly above the conveyor (245) of the egg transfer system (244). This will allow for complete removal of all the contents from within the interior (201) of the feeding chamber (200) with the use of vibration or a vacuum or both or none. In embodiments, when the first conveyor elevation unit (254) and second conveyor elevation unit (256) are extended at a second elevated height (H2) there is no gap between the terminal end of the side wall length (SW-L) of each of the first side wall (202A), second side wall (202B), third side wall (202C), and fourth side wall (202D). In embodiments, when the first conveyor elevation unit (254) and second conveyor elevation unit (256) are extended at a second elevated height (H2) there is a gap between the terminal end of the second side wall length (202BL) only.

In embodiments, when the first conveyor elevation unit (254) and second conveyor elevation unit (256) are extended at a second elevated height (H2) there is a gap between the terminal end of the first side wall length (202AL) and second side wall length (202BL). FIGS. 27-29 show non-limiting embodiments of the insect feeding module (2000, 2000A, 2000B, 2000C) contained within a cube container and for representative and illustrative purposes only show the first conveyor elevation unit (254) and second conveyor elevation unit (256) at a first retracted height (H1). Refer to above text for modes of operation and detailed description on the feeding chamber (200) integrated with the egg transfer system (244).

A first weighed enhanced feedstock stream (1F32) or synonymously termed first enhanced feedstock stream (EF1) enters the insect feeding module (2000, 2000A) on the left-hand-side through an enhanced feedstock input (206). The enhanced feedstock input (206) transfers a wet enhanced feedstock (WEF) onto the conveyor (245) of the egg transfer system (244) through a plurality of enhanced feedstock inputs (206A, 206B, 206C) so as to be configured to evenly distribute the enhanced feedstock on the conveyor (245). In embodiments the third side wall length (202CL) and fourth side wall length (202DL) are longer than the first side wall length (202AL) and second side wall length (202BL) so as to leave a gap in between the conveyor (245) and the terminal end of the first side wall length (202AL) and second side wall length (202BL). In embodiments, the first side wall length (202AL), second side wall length (202BL), third side wall length (202CL), fourth side wall length (202DL), range in between about 5 feet to about 6 feet so they may fit within the cube container for interaction with the conveyor (245) of the egg transfer system (244).

In embodiments, the first side wall length (202AL), second side wall length (202BL), third side wall length (202CL), fourth side wall length (202DL), range from: 0.5 feet to about 1 foot; between about 1 feet to about 2 feet; between about 2 feet to about 3 feet; between about 3 feet to about 4 feet; between about 4 feet to about 5 feet; between about 5 feet to about 6 feet; between about 6 feet to about 7 feet; between about 7 feet to about 8 feet; between about 8 feet to about 9 feet; between about 9 feet to about 10 feet; between about 10 feet to about 11 feet; between about 11 feet to about 12 feet; between about 12 feet to about 13 feet; between about 13 feet to about 14 feet; between about 14 feet to about 15 feet; between about 15 feet to about 16 feet; between about 16 feet to about 17 feet; between about 17 feet to about 18 feet; between about 18 feet to about 19 feet; between about 19 feet to about 20 feet; between about 20 feet to about 21 feet; between about 21 feet to about 22 feet; between about 22 feet to about 23 feet; between about 23 feet to about 24 feet; between about 24 feet to about 25 feet; between about 25 feet to about 26 feet; between about 26 feet to about 27 feet; between about 27 feet to about 28 feet; between about 28 feet to about 29 feet; between about 29 feet to about 30 feet; between about 30 feet to about 31 feet; between about 31 feet to about 32 feet; between about 32 feet to about 33 feet; between about 33 feet to about 34 feet; between about 34 feet to about 35 feet; between about 35 feet to about 36 feet; between about 36 feet to about 37 feet; between about 37 feet to about 38 feet; between about 38 feet to about 39 feet; and, between about 39 feet to about 40 feet.

In embodiments, the first side wall (202A), second side wall (202B), third side wall (202C), and fourth side wall (202D) are made up of wire, screen, or mesh that is perforated with openings smaller than the average insect length (Ni-L) average insect width (Ni-W). In embodiments, the first side wall (202A), second side wall (202B), third side wall (202C), and fourth side wall (202D) are made up of a plastic, rubber, or an impermeable substance, such as a tarp, curtain, cloth, or sheet and does not have openings in it.

An egg-depleted breeding material (246) enters the insect feeding module (2000, 2000A) on the left-hand-side through a conveyor input (247). Egg-depleted breeding material (246) is transferred onto the conveyor (245) of the egg transfer system (244) through a plurality of conveyor inputs (247A, 247B) so as to be configured to evenly distribute the enhanced feedstock on the conveyor (245). The wet enhanced feedstock (WEF) and the egg-depleted breeding material (246) are mixed together on the surface of the conveyor (245) of the egg transfer system (244).

As the conveyor motor (251) drives the conveyor (245) of the egg transfer system (244). Insects (225) within the insect feeding chamber (200) eat the wet enhanced feedstock (WEF) and lay eggs in the egg-depleted breeding material (246) which are both present on the conveyor (245) of the egg transfer system (244). The conveyor output (249) discharges a mixture of wet enhanced feedstock (WEF) and egg-laden breeding material (250) towards an egg-laden breeding material conveyor (282B) for transfer to a breeding chamber (BC) within an insect breeding module (4000, 4000A, 4000B, 4000C). A conveyor transfer bin (282A) is installed in between the conveyor output (249) to funnel and direct the mixture of wet enhanced feedstock (WEF) and egg-laden breeding material (250) towards the egg-laden breeding material conveyor (282B).

An air supply fan (271) accepts an air supply (262) through an air vent (283) and passes it through an air heater (264) for delivery into the interior (201) of the feeding chamber (200). A first access door (284) and a second access door (285) are installed on the fourth cube container side wall (CW-D). An insect evacuation output (205), that is configured to evacuate an insect and gas mixture (304) from the feeding chamber (200), is shown installed on the cube container top wall (CW-T). The insect evacuation output (205) is connected to the feeding chamber exit conduit (302). The feeding chamber exit conduit (302) is connected to the insect and gas mixture input (303) of the separator (300) within the insect evacuation module (3000). Each insect feeding module (2000, 2000A, 2000B, 2000C) may be equipped with a low voltage disconnect switch (286) and a computer (COMP). The insect evacuation output (205) is equipped with a humidity sensor (208) and a first temperature sensor (210).

FIG. 28

FIG. 28 shows a top view of one embodiment of an insect feeding module (2000, 2000A, 2000B, 2000C).

FIG. 29

FIG. 29 shows a first side view of one embodiment of an insect feeding module (2000, 2000A, 2000B, 2000C).

FIG. 30

FIG. 30 shows a front view of one embodiment of an insect evacuation module (3000). FIG. 30 shows a front view of one embodiment of an insect evacuation module (3000). Referring to FIGS. 30-32, the insect evacuation module (3000) is shown to be contained within a 40 feet high cube container conforming to the International Organization for Standardization (ISO) specifications.

The insect evacuation module (3000) includes a plurality of separators (S1, S2, S3) integrated with one common feeding chamber (FC1) as shown in FIGS. 27-29. FIGS. 30-32 shows the first separator (S1) as a first insect coarse separator (S1A), the second separator (S2) as a second insect fine separator (S2A), and the third separator (S3) as a particulate separator (S3A). The first insect coarse separator (S1A) is configured to remove a portion of the insect portion (304A) separated from the gas portion (304B) of an insect and gas mixture (304). The second insect fine separator (S2A) is configured to remove insects smaller than the insects separated in the first insect coarse separator (S1A). The particulate separator (S3A) is configured to remove particulates such as remnants of enhanced feedstock, or fine polymer particulate, for example, not only including pieces of portions of insect exoskeleton. The particulate separator (S3A) is in fluid communication with the polymer distribution module (1D) and is configured to transfer a portion of the separated particulate to the polymer tank (1D2) as polymer (1D1).

First Separator (S1), First Insect Coarse Separator (S1A)

The first insect coarse separator (S1A) has a first insect coarse separator input (S1A1) that is in fluid communication with the first feeding chamber insect evacuation output (205A) of the first feeding chamber (FC1) via a first feeding chamber exit conduit (302A). The first insect coarse separator (S1A) is configured to accept an insect and gas mixture (304) from the first feeding chamber (FC1), separate a portion of the insects from the gas and output a first insect-depleted gas stream (355) via a coarse separator gas and insect mixture output (356).

The first separator (S1) is equipped with a first dipleg (357), a first separator conveyor (358), and a first separator valve (361) interposed on the first dipleg (357). A first separated insect stream (360) is routed down the first dipleg (357), through the first separator valve (361) and into the first separator conveyor (358). In embodiments, the first separator conveyor (358) is a compression screw (359) which serves to instantly kill insects by compressing them. The first separated insect stream (360) may in turn be transferred to an evacuated separated insect conveyor (378) via a first separator conveyor connection (379).

The evacuated separated insect conveyor (378) has a motor (378A) that is configured to transfer the first separated insect stream (360) to a grinder (1250) within an insect grinding module via a first separated insect stream input (371). In other embodiments, the first separated insect stream (360) may be sent to a pathogen removal unit (1550) within a pathogen removal module, or to a within a lipid extraction unit (1501) lipid extraction module.

Second Separator (S2), Second Insect Fine Separator (S2A)

The second insect fine separator (S2A) has a second insect fine separator input (S2A1) that is in fluid communication with the coarse separator gas and insect mixture output (356) of the first insect coarse separator (S1A). The second insect fine separator (S2A) is configured to accept a first insect-depleted gas stream (355) from the first insect coarse separator (S1A), separate a portion of the insects from the gas and output a second insect-depleted gas stream (362) via a fine separator gas and particulate mixture output (363).

The second separator (S2) is equipped with a second dipleg (364), a second separator conveyor (365), and a second separator valve (368) interposed on the second dipleg (364). A second separated insect stream (360) is routed down the second dipleg (364), through the second separator valve (368) and into the second separator conveyor (365). In embodiments, the second separator conveyor (365) is a compression screw (366) which serves to instantly kill insects by compressing them.

In embodiments, the second separator conveyor (365) is a not a compression screw (366) but instead routes the second separated insect stream (367) to the to a breeding chamber (BC) via a breeding chamber fine separated insect portion input (375). In embodiments, the second separator conveyor (365) is a not a compression screw (366) but instead routes the second separated insect stream (367) to a plurality of other destinations such as to the grinder (1250), pathogen removal unit (1550), or lipid extraction unit (1501). The second separated insect stream (367) may in turn be transferred to an evacuated separated insect conveyor (378) via a second separator conveyor connection (380) to form a combined first and second separator insect stream (381).

The combined first and second separator insect stream (381) is a mixture of the first separated insect stream (360) and the second separated insect stream (367). The evacuated separated insect conveyor (378) has a motor (378A) that is configured to transfer the combined first and second separator insect stream (381) to a grinder (1250) within an insect grinding module via a first separated insect stream input (371). In other embodiments, the first separated insect stream (360) may be sent to a pathogen removal unit (1550) within a pathogen removal module, or to a within a lipid extraction unit (1501) lipid extraction module.

Third Separator (S3), Particulate Separator (S3A)

The particulate separator (S3A) has a particulate separator input (S3A1) that is in fluid communication with the fine separator gas and particulate mixture output (363) of the second insect fine separator (S2A). The particulate separator (S3A) is configured to accept a second insect-depleted gas stream (362) from the second insect fine separator (S2A), separate a portion of the particulates from the gas and output a particulate-depleted gas stream (369) to the insect evacuation fan (312).

The insect evacuation fan (312) is in fluid with the breeding chamber (BC) via a breeding chamber exhaust input (376) and is configured to discharge the exhaust (377) into the breeding chamber (BC). In embodiments, the separated insect conveyor (328) of the third separator (S3) particulate separator (S3A) is in fluid communication with the polymer distribution module (1D) and is configured to transfer a portion of the separated particulate stream (370) to the polymer tank (1D2) as polymer (1D1).

In embodiments, the separated insect conveyor (328) of the third separator (S3) particulate separator (S3A) is in fluid communication with the polymer distribution module (1D) and is configured to transfer a portion of the separated particulate stream (370) to the polymer tank (1D2) as a polymer (1D1). The insect evacuation module (3000) is equipped with a first access door (386), second access door (387), computer (COMP), low voltage disconnect switch (388), and an air vent (389) that is configured to accept an air supply (390).

FIG. 31

FIG. 31 shows a top view of one embodiment of an insect evacuation module (3000).

FIG. 32

FIG. 32 shows a first side view of one embodiment of an insect evacuation module (3000).

FIG. 33

FIG. 33 shows a front view of one embodiment of an insect breeding module (4000, 4000A, 4000B, 4000C).

Referring to FIGS. 33-36, the insect breeding module (4000, 4000A, 4000B, 4000C) is shown to be contained within a 40 feet high cube container conforming to the International Organization for Standardization (ISO) specifications.

A feeding chamber 1 egg-laden breeding material transfer line (R1, 340) transfers egg-laden breeding material (250) via an egg-laden breeding material conveyor (282B) into the insect breeding module (4000, 4000A) from the left-hand-side. Egg-laden breeding material (250), and optionally a mixture of egg-laden breeding material (250) and a wet enhanced feedstock (WEF), are distributed onto a lower conveyor belt (415) of a first conveyor transfer unit (XY1A). The egg-laden breeding material (250) being transferred to the interior (BCIN) of the breeding chamber 1 (BC1) where it is first elevated via a first conveyor transfer unit (XY1A) to the first conveyor height (CH1A) of a first conveyor (CY1A) operating in a clockwise motion of operation.

In embodiments, the breeding chamber (BC) shown in FIGS. 33-36 represent a typical breeding chamber 1 (BC1), breeding chamber 2 (BC2), breeding chamber 3 (BC3) as shown in FIG. 17. In embodiments, the first conveyor transfer unit (XY1A) takes the form of a vertical lift conveyor (409) including a lower conveyor unit (410) and an upper conveyor unit (411). The vertical lift conveyor (409) is equipped with a lift conveyor drive unit (419) that is configured to rotate the rollers within the lower conveyor unit (410) and upper conveyor unit (411).

The lower conveyor unit (410) includes a first lower conveyor roller (412), second lower conveyor roller (413), third lower conveyor roller (414), and an endless lower conveyor belt (415) in communication with each roller (412, 423, 414) and the lift conveyor drive unit (419). The upper conveyor unit (411) includes a first upper conveyor belt roller (416), second upper conveyor roller (417), and an endless upper conveyor belt (418) in communication with each roller (416, 417) and the lift conveyor drive unit (419).

Egg-laden breeding material (250), and optionally a mixture of egg-laden breeding material (250) and a wet enhanced feedstock (WEF) are distributed onto the lower conveyor belt (415) of the lower conveyor unit (410). The breeding material and enhanced feedstock remnants are sandwiched in between the lower conveyor belt (415) of the lower conveyor unit (410) and the upper conveyor belt (418) of the upper conveyor unit (411) and is elevated to the first conveyor height (CH1A) of a first conveyor (CY1A) operating in a clockwise motion of operation.

The first conveyor (CY1A) is positioned at a vertical height above at least one other conveyor. FIGS. 33-36 shows five conveyors (CY1A, CY2A, CY3A, CY4A, CY5A) and the first conveyor (CY1A) is positioned at a vertical height above each one of a second conveyor (CY2A), third conveyor (CY3A), fourth conveyor (CY4A), and fifth conveyor (CY5A). The second conveyor (CY2A) is positioned at a vertical height above each one of a third conveyor (CY3A), fourth conveyor (CY4A), and fifth conveyor (CY5A). The third conveyor (CY3A) is positioned at a vertical height above each one of a fourth conveyor (CY4A), and fifth conveyor (CY5A). The fourth conveyor (CY4A) is positioned at a vertical height above each one of the fifth conveyor (CY5A).

The first conveyor (CY1A) is installed at a first conveyor height (CH1A) above the second conveyor (CY2A). The second conveyor (CY2A) is installed at a second conveyor height (CH2A) above the third conveyor (CY3A). The third conveyor (CY3A) is installed at a third conveyor height (CH3A) above the fourth conveyor (CY4A). The fourth conveyor (CY4A) is installed at a fourth conveyor height (CH4A) above the fifth conveyor (CY5A).

FIG. 33-36 shows the first conveyor (CY1A), third conveyor (CY3A), fifth conveyor (CY5A) all configured to operate in a clockwise motion of operation. FIG. 33-36 shows the second conveyor (CY2A) and fourth conveyor (CY4A) configured to operate in a counter-clockwise motion of operation.

The first conveyor (CY1A) rotates in a clockwise motion about a first conveyor first roller (P1) and a first conveyor second roller (P2). The second conveyor (CY2A) rotates in a counter-clockwise motion about a second conveyor first roller (P3) and a second conveyor second roller (P4). The third conveyor (CY3A) rotates in a clockwise motion about a third conveyor first roller (P5) and a third conveyor second roller (P6). The fourth conveyor (CY4A) rotates in a counter-clockwise motion about a fourth conveyor first roller (P7) and a fourth conveyor second roller (P8). The fifth conveyor (CY5A) rotates in a clockwise motion about a fifth conveyor first roller (P9) and a fifth conveyor second roller (P10).

A drive unit (404) is equipped with a motor (405) to drive a sprocket (406) and a roller (407). The drive unit (404) is operatively connected to the first conveyor first roller (P1) of the first conveyor (CY1A), second conveyor second roller (P4) of the second conveyor (CY2A), the third conveyor first roller (P5) of the third conveyor (CY3A), the fourth conveyor second roller (P8) of the fourth conveyor (CY4A), and the fifth conveyor first roller (P9) of the fifth conveyor (CY5A).

Specifically, the sprocket (406) driven by the motor (405) of the drive unit (404) drives a roller chain (408) that is configured to operate each conveyor (CY1A, CY2A, CY3A, CY4A, CY5A). The roller chain (408) is configured to interact with a roller chain support roller (P11) in between the first conveyor first roller (P1) and sprocket (406) of the drive unit (404).

The circuit including the roller chain (408), sprocket (406), and drive unit (404) turns the fifth conveyor first roller (P9), third conveyor first roller (P5), and first conveyor first roller (P1) in the clockwise motion. The circuit including the roller chain (408), sprocket (406), and drive unit (404) also turns the fourth conveyor second roller (P8) and second conveyor second roller (P4) in the counter-clockwise motion.

The first conveyor (CY1A) transfers a mixture of egg-laden breeding material (250) and remnants of an enhanced feedstock to the second conveyor (CY2A). The second conveyor (CY2A) transfers a mixture of egg-laden breeding material (250) and remnants of an enhanced feedstock, and possibly hatched insects to the third conveyor (CY3A). The third conveyor (CY3A) transfers a mixture of egg-laden breeding material (250), remnants of an enhanced feedstock, and possibly hatched insects to the fourth conveyor (CY4A). The fourth conveyor (CY4A) transfers a mixture of egg-laden breeding material (250), remnants of an enhanced feedstock, and possibly hatched insects to the fifth conveyor (CY5A). The fifth conveyor (CY5A) transfers a mixture of hatched insects, breeding material, and remnants of an enhanced feedstock to a hatched insect conveyor (402) and out of the insect breeding module (4000, 4000A, 4000B, 4000C) via a feeding chamber 1 breeding chamber output (BC1B).

A conveyor transfer bin (401) is interposed in between the fifth conveyor (CY5A) and the hatched insect conveyor (402) to funnel and direct a mixture of hatched insects, breeding material, and remnants of an enhanced feedstock from the insect breeding module (4000, 4000A, 4000B, 4000C) and into the hatched insect separation module (5000).

A conveyor side view (CSV) may be viewed in FIGS. 35-36 from the length along the insect breeding module (4000) conveyor (CY1A, CY2A, CY3A, CY4A, CY5A). The insect breeding module (4000, 4000A, 4000B, 4000C) is equipped with a first access door (420), second access door (421), low voltage disconnect switch (422), temperature sensor (423), humidity sensor (425), and an air vent (427) configured to introduce an air supply (428) to the interior (BCIN) of the breeding chamber (BC). The insect breeding module (4000, 4000A, 4000B, 4000C) may also be equipped with a temperature control unit (429) to maintain a constant temperature with the interior (BCIN) of the breeding chamber (BC).

The first conveyor (CY1A) is equipped with a first hatched insect detection sensor (OS1) to determine if insects have hatched and are active on the surface of the first conveyor (CY1A). The second conveyor (CY2A) is equipped with a second hatched insect detection sensor (OS2) to determine if insects have hatched and are active on the surface of the second conveyor (CY2A). The third conveyor (CY3A) is equipped with a third hatched insect detection sensor (OS3) to determine if insects have hatched and are active on the surface of the third conveyor (CY3A). The fourth conveyor (CY4A) is equipped with a fourth hatched insect detection sensor (OS4) to determine if insects have hatched and are active on the surface of the fourth conveyor (CY4A). The fifth conveyor (CY5A) is equipped with a fifth hatched insect detection sensor (OS5) to determine if insects have hatched and are active on the surface of the fifth conveyor (CY5A). Either of the hatched insect detection sensors (OS1, OS2, OS3, OS4, OS5) may be an optical sensor, digital camera, motion sensor, active infrared (AIRs) sensor, passive infrared (PIRs) sensor, microwave motion sensor, continuous wave radar motion sensor (CW), vibration motion sensor, IR sensor, ultrasonic sensor, proximity sensor, and touch sensor, mass sensor, laser sensor, or the like.

FIG. 34

FIG. 34 shows a top view of one embodiment of an insect breeding module (4000, 4000A, 4000B, 4000C). A side wall (403) may be positioned in the insect breeding module (4000, 4000A, 4000B, 4000C) to permit access and maintenance as shown in FIGS. 34-35. In embodiments, the side wall (403) is made up of a plastic, rubber, or an impermeable substance, such as a tarp, curtain, cloth, or sheet and does not have openings in it. In embodiments, the side wall (403) is made up of wire, screen, or mesh that is perforated with openings smaller than the average insect length (Ni-L) average insect width (Ni-W).

FIG. 35

FIG. 35 shows a first side view of one embodiment of an insect breeding module (4000, 4000A) at a cutaway section of the conveyor side view (CSV). In embodiments, the breeding chamber (BC) includes a plurality of conveyors including a first conveyor (CY1A), second conveyor (CY2A), third conveyor (CY3A), fourth conveyor (CY4A), and fifth conveyor (CY5A) that are operatively rotated by a plurality of rollers including a first conveyor first roller (P1), second conveyor second roller (P4), third conveyor first roller (P5), fourth conveyor second roller (P8), and fifth conveyor first roller (P9).

FIG. 36

FIG. 36 shows an embodiment of the insect breeding module (4000, 4000A, 4000B, 4000C) from the conveyor side view (CSV). A side wall (403) may be positioned within the insect breeding module (4000, 4000A, 4000B, 4000C) to permit a plurality of breeding trains within one since cube container to be separated apart from the temperature control unit (429). Three separate breeding chamber conveyor trains are illustrated with a side wall (403) positioned to space-apart the breeding chamber conveyor trains (BCT1, BCT2, BCT3) from the temperature control unit (429).

A first breeding chamber conveyor train (BCT1) includes a plurality of conveyors driven by a plurality of rollers including a first conveyor first roller (P1), second conveyor second roller (P4), third conveyor first roller (P5), fourth conveyor second roller (P8), and fifth conveyor first roller (P9). A second breeding chamber conveyor train (BCT2) includes a plurality of conveyors driven by a plurality of rollers including a first conveyor first roller (P1B), second conveyor second roller (P4B), third conveyor first roller (P5B), fourth conveyor second roller (P8B), and a fifth conveyor first roller (P9B). A third breeding chamber conveyor train (BCT3) includes a plurality of conveyors driven by a plurality of rollers including a first conveyor first roller (P1C), second conveyor second roller (P4C), third conveyor first roller (P5C), fourth conveyor second roller (P8C), and fifth conveyor first roller (P9C).

FIG. 37

FIG. 37 shows a front view of one embodiment of a hatched insect separation module (5000, 5000A, 5000B, 5000C). Referring to FIGS. 37-39, the hatched insect separation module (5000, 5000A, 5000B, 5000C) is shown to be contained within a 40 feet high cube container conforming to the International Organization for Standardization (ISO) specifications.

FIGS. 37-39 shows the hatched insect separation module (5000) equipped with a breeding material and insect separator (SEP1A) and a breeding material tank (500). A hatched insect conveyor (402) transfers a mixture of hatched insects, breeding material, and remnants of an enhanced feedstock into a breeding material and insect separator (SEP1A) via a hatched insect and breeding material input (515).

The breeding material and insect separator (SEP1A) includes an interior (SIN1), a separator input (1SEPA), a separator material output (1SEPB), and a separator insect output (1SEPC). The breeding material and insect separator (SEP1A) is connected to breeding chamber 1 (BC1) via a breeding chamber 1 hatched egg and breeding material transfer line (U1). The breeding chamber 1 hatched egg and breeding material transfer line (U1) is connected at one end to the breeding chamber 1 (BC1) via a feeding chamber 1 breeding chamber output (BC1B) and connected at another end to the breeding material and insect separator (SEP1A) via a separator input (1SEPA).

The breeding material and insect separator (SEP1A) is equipped with a dipleg (517) to transfer an egg-depleted material (518) to an egg-depleted material transfer conveyor (519). The egg-depleted material transfer conveyor (519) is equipped with a motor (520) and is configured to transfer separated breeding material (523) to the interior (501) of the breeding material tank (500) via a material transfer line (522). The material transfer line (522) is connected at one end to the egg-depleted material transfer conveyor (519) and at another rend to the breeding material input (502) of the breeding material tank (500).

The separator input (1SEPA) is configured to accept hatched insects and breeding material from the fifth conveyor (CY5A) of breeding chamber 1 (BC1), and separate hatched insects (400) from the breeding material (523). The separator insect output (1SEPC) is configured to discharge hatched insects (400) from the interior (SIN1) of the breeding material and insect separator (SEP1A) and route the hatched insects (400) to either one of a plurality of feeding chambers (FC1, FC2, FC3) via a separator hatched insect transfer line (O1). Specifically, separator insect output (1SEPC) is configured to discharge hatched insects (400) first feeding chamber (FC1), or to the second feeding chamber (FC2), or to the third feeding chamber (FC3). Hatched insects (400) transferred from the hatched insect separation module (5000) to the insect feeding module (2000) are made available to the first feeding chamber (FC1) via a first hatched insect output (DFC).

The breeding material tank (500) has an interior (501), a breeding material input (502), and a breeding material output (510). Breeding material, and remnants of an enhanced feedstock may be transferred from the breeding material and insect separator (SEP1A) interior (501) of the breeding material tank (500) through a breeding material input (502). Breeding material, and remnants of an enhanced feedstock may be substantially evenly distributed to the interior (501) of the breeding material tank (500) via a breeding material input distributor (502A).

The breeding material tank (500) also has a top section (503), a bottom section (506), and an interior (501) defined by at least one side wall (507). A breeding material screw conveyor (508) is located at the bottom section (506) and configured to transfer breeding material to either one of a plurality of feeding chambers (FC1, FC2, FC3) via a breeding material transfer line (511). The breeding material transfer line (511) is connected at one end to any one of a plurality of feeding chambers (FC1, FC2, FC3) and connected at another end to the breeding material screw conveyor (508) via a breeding material output (510). The breeding material screw conveyor (508) is equipped with a breeding material screw conveyor motor (512). The hatched insect separation module (5000) is equipped with a first access door (528), second access door (529), low voltage disconnect switch (530), and a computer (COMP).

FIG. 38

FIG. 38 shows a top view of one embodiment of a hatched insect separation module (5000, 5000A).

FIG. 39

FIG. 39 shows a first side view of one embodiment of a hatched insect separation module (5000, 5000A).

FIG. 40

FIG. 40 shows Table 1 with upper and lower ranges of feedstock mineral enhancers, feedstock vitamin enhancers, feedstock polymer enhancers, and other 'energy-Insect™' enhancers.

FIG. 41A

FIG. 41A shows one non-limiting embodiment of a method for raising Orthoptera order of insects. In embodiments, the present disclosure describes a method for raising Orthoptera order of insects, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing a portion of said egg-laying insects from said insect feeding chamber by applying a vacuum with a velocity pressure range from about 0.001 inches of water to about 400 inches of water and at velocity from about 0.05 feet per second to about 1500 feet per second. In embodiments, the insect feeding chamber may operate at a feedstock to insect ratio ranging from between about 1 ton of feedstock per ton of insects produced to about 5 tons of feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.

FIG. 41B

FIG. 41B shows one non-limiting embodiment of another method for raising Orthoptera order of insects. In embodiments, the present disclosure describes a method for raising Orthoptera order of insects, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing a portion of said egg-laying insects from said insect feeding chamber by vibrating at least a portion of said insect feeding chamber. In embodiments, the insect feeding chamber may operate at a feedstock to insect ratio ranging from between about 1 ton of feedstock per ton of insects produced to about 5 tons of feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.

FIG. 42A

FIG. 42A shows one non-limiting embodiment of a method for raising Orthoptera order of insects. In embodiments, the present disclosure describes a method for raising Orthoptera order of insects, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into said insect feeding chamber; (h) removing a portion of said egg-laying insects said insect feeding chamber by applying a vacuum with a velocity pressure range from about 0.001 inches of water to about 400 inches of water and at velocity from about 0.05 feet per second to about 1500 feet per second.

FIG. 42B

FIG. 42B shows one non-limiting embodiment of another method for raising Orthoptera order of insects. In embodiments, the present disclosure describes a method for raising Orthoptera order of insects, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into said insect feeding chamber; (h) removing a portion of said egg-laying insects from said insect feeding chamber by vibrating at least a portion of said insect feeding chamber.

FIG. 43A

FIG. 43A shows one non-limiting embodiment of a method for raising Orthoptera order of insects. In embodiments, the present disclosure describes a method for raising Orthoptera order of insects, the method comprising: (a) providing a plurality of insect feeding chambers having egg-laying insects present therein; (b) mixing feedstock with one or more additives from the group consisting of water, minerals, vitamins, and polymer to form an enhanced feedstock; (c) apportioning said enhanced feedstock into a plurality of enhanced feedstock streams; (d) introducing said plurality of enhanced feedstock streams into said plurality of insect feeding chambers to feed the egg-laying insects present therein; (e) removing at least a portion of eggs laid by the egg-laying insects; (f) incubating at least a portion of the removed eggs; (g) hatching at least a portion of incubated eggs; (h) introducing a portion of hatched insects into at least one of the plurality of insect feeding chambers; (i) removing a portion of said egg-laying insects from said plurality of insect feeding chambers by applying a vacuum with a velocity pressure range from about 0.001 inches of water to about 400 inches of water and at velocity from about 0.05 feet per second to about 1500 feet per second.

FIG. 43B

FIG. 43B shows one non-limiting embodiment of another method for raising Orthoptera order of insects. In embodiments, the present disclosure describes a method for raising Orthoptera order of insects, the method comprising: (a) providing a plurality of insect feeding chambers having egg-laying insects present therein; (b) mixing feedstock with one or more additives from the group consisting of water, minerals, vitamins, and polymer to form an enhanced feedstock; (c) apportioning said enhanced feedstock into a plurality of enhanced feedstock streams; (d) introducing said plurality of enhanced feedstock streams into said plurality of insect feeding chambers to feed the egg-laying insects present therein; (e) removing at least a portion of eggs laid by the egg-laying insects; (f) incubating at least a portion of the removed eggs; (g) hatching at least a portion of incubated eggs; (h) introducing a portion of hatched insects into at least one of the plurality of insect feeding chambers; (i) removing a portion of said egg-laying insects from said plurality of insect feeding chambers by vibrating at least a portion of said plurality of insect feeding chambers.

FIG. 44A

FIG. 44A shows one non-limiting embodiment of a method for raising Orthoptera order of insects. In embodiments, the present disclosure describes a method for raising Orthoptera order of insects, the method comprising: (a) providing a plurality of insect feeding chambers having egg-laying insects of said order present therein; (b) mixing feedstock with one or more additives from the group consisting of water, minerals, vitamins, and polymer to form an enhanced feedstock; (c) apportioning said enhanced feedstock into a plurality of enhanced feedstock streams; (d) introducing said plurality of enhanced feedstock streams into said plurality of insect feeding chambers to feed the egg-laying insects present therein; and, (e) removing a portion of said egg-laying insects from said plurality of insect feeding chambers by applying a vacuum with a velocity pressure range from about 0.001 inches of water to about 400 inches of water and at velocity from about 0.05 feet per second to about 1500 feet per second. In embodiments, the insect feeding chamber may operate at a feedstock to insect ratio ranging from between about 1 ton of feedstock per ton of insects produced to about 5 tons of feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.

FIG. 44B

FIG. 44B shows one non-limiting embodiment of another method for raising Orthoptera order of insects. In embodiments, the present disclosure describes a method for raising Orthoptera order of insects, the method comprising: (a) providing a plurality of insect feeding chambers having egg-laying insects of said order present therein; (b) mixing feedstock with one or more additives from the group consisting of water, minerals, vitamins, and polymer to form an enhanced feedstock; (c) apportioning said enhanced feedstock into a plurality of enhanced feedstock streams; (d) introducing said plurality of enhanced feedstock streams into said plurality of insect feeding chambers to feed the egg-laying insects present therein; and, (e) removing a portion of said egg-laying insects from said plurality of insect feeding chambers by vibrating at least a portion of said plurality of insect feeding chambers. In embodiments, the insect feeding chamber may operate at a feedstock to insect ratio ranging from between about 1 ton of feedstock per ton of insects produced to about 5 tons of feedstock per ton of insects produced. In embodiments, the feeding chamber operates at a temperature ranging from between 50 degrees Fahrenheit to about 120 degrees Fahrenheit. In embodiments, the feeding chamber operates at a pressure ranging from between 12 psia to about 16 psia.

FIG. 45A

FIG. 45A shows one non-limiting embodiment of a method for raising Orthoptera order of insects to generate a multifunctional alimentary flour composition. In embodiments, the present disclosure describes a method for raising Orthoptera order of insects to generate a multifunctional alimentary flour composition, the method comprising: (a) providing a plurality of insect feeding chambers having egg-laying insects present therein; (b) mixing feedstock with one or more additives from the group consisting of water, minerals, vitamins, and polymer to form an enhanced feedstock; (c) apportioning said enhanced feedstock into a plurality of enhanced feedstock streams; introducing said plurality of enhanced feedstock streams into said plurality of insect feeding chambers to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into at least one of the plurality of insect feeding chambers; (h) removing a portion of said egg-laying insects from said plurality of insect feeding chambers; (i) grinding a portion of the removed insects to form a stream of ground insects; (j) creation of a multifunctional alimentary flour composition by mixing ground insects of step (i) with one or more ingredients from the group consisting of fiber-starch materials, binding agents, density improving textural supplements, moisture improving textural supplements, and *cannabis* enhancers.

FIG. 45B

FIG. 45B shows one non-limiting embodiment of another method for raising Orthoptera order of insects to generate a multifunctional alimentary flour composition. In embodiments, the present disclosure describes a method for raising Orthoptera order of insects to generate a multifunctional alimentary flour composition, the method comprising: (a) providing a plurality of insect feeding chambers having egg-laying insects present therein; (b) mixing feedstock with one or more additives from the group consisting of water, minerals, vitamins, and polymer to form an enhanced feedstock; (c) apportioning said enhanced feedstock into a plurality of enhanced feedstock streams; introducing said plurality of enhanced feedstock streams into said plurality of insect feeding chambers to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into at least one of the plurality of insect feeding chambers; (h) removing a portion of said egg-laying insects from said plurality of insect feeding chambers; (i) removing pathogens from a portion of the removed insects to form a stream of pathogen-depleted insects; (j) creation of a multifunctional alimentary flour composition by mixing a portion of the stream of pathogen-depleted insects of step (i) with one or more ingredients from the group consisting of fiber-starch materials, binding agents, density improving textural supplements, moisture improving textural supplements, and *cannabis* enhancers.

FIG. 46

FIG. 46 shows one non-limiting embodiment of another method for raising Orthoptera order of insects to generate a multifunctional alimentary flour composition. In embodiments, the present disclosure describes a method for raising Orthoptera order of insects to generate a multifunctional alimentary flour composition, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into said insect feeding chamber; (h) removing a portion of said egg-laying insects from said insect feeding chamber; (i) grinding a portion of the removed insects to form a stream of ground insects; (j) creation of a multifunctional alimentary flour composition by mixing ground insects of step (i) with one or more ingredients from the group consisting of fiber-starch materials, binding agents, density improving textural supplements, moisture improving textural supplements, and *cannabis* enhancers.

FIG. 47

FIG. 47 shows one non-limiting embodiment of a method for raising Orthoptera order of insects for the separation of lipids contained within said insects. In embodiments, the present disclosure describes a method for raising Orthoptera order of insects to extract lipids contained within said insects, the method comprising: (a) providing an insect feeding chamber having egg-laying insects present therein; (b) mixing feedstock with one or more additives from the group consisting of water, minerals, vitamins, and polymer to form an enhanced feedstock; (c) introducing said enhanced feedstock into said insect feeding chamber to feed the egg-laying insects present therein; (d) removing at least a portion of eggs laid by the egg-laying insects; (e) incubating at least a portion of the removed eggs; (f) hatching at least a portion of incubated eggs; (g) introducing a portion of hatched insects into said insect feeding chamber; (h) removing a portion of said egg-laying insects from said insect feeding chamber; (i) extracting lipids from a portion of the removed insects.

Thus, specific systems and methods of an Insect Production Superstructure System (IPSS) have been disclosed. It should be apparent, however, to those skilled in the art that many more modifications besides those already described are possible without departing from the inventive concepts herein. The inventive subject matter, therefore, is not to be restricted except in the spirit of the disclosure.

Thus, the applicant(s) should be understood to have support to claim and make a statement of invention to at least: i) each of the process devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the inventive technology, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Although the foregoing text sets forth a detailed description of numerous different embodiments of the disclosure, it should be understood that the scope of the disclosure is defined by the words of the claims set forth at the end of this patent. The detailed description is to be construed as exemplary only and does not describe every possible embodiment of the disclosure because describing every possible embodiment would be impractical, if not impossible. Numerous alternative embodiments could be implemented, using either current technology or technology developed after the filing date of this patent, which would still fall within the scope of the claims defining the disclosure.

Thus, many modifications and variations may be made in the techniques and structures described and illustrated herein without departing from the spirit and scope of the present disclosure. Accordingly, it should be understood that the methods and apparatus described herein are illustrative only and are not limiting upon the scope of the disclosure.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

LISTING OF REFERENCE NUMERALS

Insect Production Superstructure System (IPSS)
enhanced feedstock transfer line (002)
first enhanced feedstock transfer line (004)
second enhanced feedstock transfer line (006)
feeding chamber transfer insect line (008)
first feeding chamber insect transfer line (010)
second feeding chamber insect transfer line (012)
combined collected insect transfer line (014)
ground insect transfer line (016)
pathogen-depleted insect transfer line (018)
first egg-laden breeding material transfer line (020)
second egg-laden breeding material transfer line (021)
combined egg-laden breeding material transfer line (022)
first feeding chamber hatched insect transfer line (024)
second feeding chamber hatched insect transfer line (026)
feedstock mixing (step A)
feedstock splitting (step B)
insect feeding chamber #1 (step C1)
insect feeding chamber #2 (step C2)
insect breeding (step D)
insect collection (step E)
insect grinding (step F)
pathogen removal (step G)
multifunctional flour mixing (step H)
lipid extraction (step J)
extracted lipids (028)
enhanced feedstock mixing module (1000)
feedstock distribution module (1A)
feedstock (1A1)
feedstock tank (1A2)
interior (1A3)
feedstock input (1A4)
feedstock conveyor (1A5)
feedstock conveyor output (1A6)
feedstock mass sensor (1A7)
signal (1A8)
feedstock conveyor motor (1A9)
controller (1A10)
signal (1A11)
feedstock moisture sensor (1A12A)
signal (1A13A)
enhanced feedstock moisture sensor (1A12B)
signal (1A13B)
feedstock transfer line (1A14)
supply access door (1A15)
supply access door opening/closing unit (1A16)
weather seal (1A17)
air inlet vent (1A18)
air (1A19)
enhanced feedstock transport screw (1A20)
enhanced feedstock transport screw connection (1A20A)
live floor screw (1A21)
motor (1A22)
feedstock module access door (1A23)
first enhanced feedstock stream (EF1)
second enhanced feedstock stream (EF2)
third enhanced feedstock stream (EF3)
mineral distribution module (1B)
minerals (1B1)
mineral tank (1B2)
interior (1B3)
mineral input (1B4)
mineral conveyor (1B5)
mineral conveyor output (1B6)
mineral mass sensor (1B7)
signal (1B8)
minerals conveyor motor (1B9)
controller (1B10)
signal (1B11)
mineral transfer line (1B12)
supply access door (1B13)
supply access door opening/closing unit (1B14)
weather seal (1B15)
air inlet vent (1B16)
air (1B17)
enhanced feedstock transport screw connection (1B18)
live floor screw (1B20)
motor (1B21)
mineral module access door (1B22)
vitamin distribution module (1C)
vitamins (1C1)
vitamin tank (1C2)
interior (1C3)
vitamin input (1C4)
vitamin conveyor (1C5)
vitamin conveyor output (1C6)
vitamin mass sensor (1C7)
signal (1C8)
vitamin conveyor motor (1C9)
controller (1C10)
signal (1C11)
vitamin transfer line (1C12)
supply access door (1C13)
supply access door opening/closing unit (1C14)
weather seal (1C15)
air inlet vent (1C16)
air (1C17)
enhanced feedstock transport screw connection (1C18)
live floor screw (1C20)
motor (1C21)
vitamin module access door (1C22)
polymer distribution module (1D)
polymer (1D1)
polymer tank (1D2)
interior (1D3)
polymer input (1D4)
polymer conveyor (1D5)
polymer conveyor output (1D6)
polymer mass sensor (1D7)
signal (1D8)
polymer conveyor motor (1D9)
controller (1D10)
signal (1D11)
polymer transfer line (1D12)
supply access door (1D13)
supply access door opening/closing unit (1D14)
weather seal (1D15)
air inlet vent (1D16)
air (1D17)
enhanced feedstock transport screw connection (1D18)
live floor screw (1D20)
motor (1D21)
polymer module access door (1D22)
dry enhanced feedstock (DEF)
low voltage disconnect switch (1000LV)
water distribution module (1E)
water (1E1)
first water pressure sensor (1E2)

signal (1E3)
water input line (1E4)
contaminant-laden water (1E5)
first water treatment unit (1E6)
first water treatment unit input (1E7)
first water treatment unit output (1E8)
first contaminant-depleted water (1E9)
first contaminant-depleted water transfer line (1E10)
second water treatment unit (1E11)
second water treatment unit input (1E12)
second water treatment unit output (1E13)
second contaminant-depleted water (1E14)
second contaminant-depleted water transfer line (1E15)
water tank (1E16)
interior (1E17)
water input (1E18)
water supply line (1E19)
water output (1E20)
water discharge line (1E21)
water supply pump (1E22)
water supply valve (1E23)
controller (1E24)
signal (1E25)
high water level sensor (1E26)
signal (1E27)
low water level sensor (1E28)
signal (1E29)
second water pressure sensor (1E30)
signal (1E31)
pressurized water supply (1E32)
pressurized water supply line (1E33)
water flow sensor (1E34)
signal (1E35)
water control valve (1E36)
controller (1E37)
signal (1E38)
third water pressure sensor (1E39)
signal (1E40)
water transfer line (1E41)
water quality sensor (1E42)
signal (1E43)
enhancers (1E44)
enhancer tank (1E45)
interior (1E46)
enhancer tank output (1E47)
enhancer transfer line (1E48)
enhancer input (1E49)
enhancer flow sensor (1E50)
signal (1E51)
water enhancer supply valve (1E52)
controller (1E53)
signal (1E54)
first access door (1E55)
second access door (1E56)
air vent (1E57)
air supply (1E58)
low voltage disconnect switch (1E59)
enhanced feedstock distribution module (1F)
enhanced feedstock transfer line (1F0)
wet enhanced feedstock (WEF)
enhanced feedstock splitter (1F1)
interior (1F2)
splitter input (1F3)
first splitter input (1F3A)
insertion distance (1F3A1)
second splitter input (1F3B)
third splitter input (1F3C)
top section (1F4)
bottom section (1F5)
side wall (1F6)
first splitter level sensor (1F7)
signal (1F8)
splitter first screw conveyor (1F9)
first output (1F10)
splitter first screw conveyor motor (1F11)
controller (1F12)
signal (1F13)
splitter second screw conveyor (1F14)
second output (1F15)
splitter second screw conveyor motor (1F16)
controller (1F17)
signal (1F18)
splitter third screw conveyor (1F19)
third output (1F20)
splitter third screw conveyor motor (1F21)
controller (1F22)
signal (1F23)
first weigh screw (1F24)
first weigh screw input (1F25)
first weigh screw output (1F26)
mass sensor (1F27)
signal (1F28)
first weigh screw motor (1F29)
controller (1F30)
signal (1F31)
first weighed enhanced feedstock stream (1F32)
second weigh screw (1F33)
second weigh screw input (1F34)
second weigh screw output (1F35)
mass sensor (1F36)
signal (1F37)
second weigh screw motor (1F38)
controller (1F39)
signal (1F40)
second weighed enhanced feedstock stream (1F41)
third weigh screw (1F42)
third weigh screw input (1F43)
third weigh screw output (1F44)
mass sensor (1F45)
signal (1F46)
third weigh screw motor (1F47)
controller (1F48)
signal (1F49)
third weighed enhanced feedstock stream (1F50)
first access door (1F51)
second access door (1F52)
air vent (1F53)
air supply (1F54)
low voltage disconnect switch (1F55)
insect feeding module (2000)
first insect feeding module (2000A)
second insect feeding module (2000B)
third insect feeding module (2000C)
feeding chamber (200)
first feeding chamber (FC1)
second feeding chamber (FC2)
third feeding chamber (FC3)
interior (201)
side wall (202)
first side wall (202A)
second side wall (202B)
third side wall (202C)
fourth side wall (202D)
first side wall length (202AL)

second side wall length (202BL)
third side wall length (202CL)
fourth side wall length (202DL)
first cube container side wall (CW-A)
second cube container side wall (CW-B)
third cube container side wall (CW-C)
fourth cube container side wall (CW-D)
cube container top wall (CW-T)
side wall length (SW-L)
top (203)
bottom (204)
insect evacuation output (205)
first feeding chamber insect evacuation output (205A)
second feeding chamber insect evacuation output (205B)
third feeding chamber insect evacuation output (205C)
first enhanced feedstock input (206A)
second enhanced feedstock input (206B)
third enhanced feedstock input (206C)
enhanced feedstock distributor (207)
humidity sensor (208)
signal (209)
first temperature sensor (210)
signal (211)
second temperature sensor (212)
signal (213)
vibration unit (214)
vibration unit motor (215)
controller (216)
signal (217)
first vibration unit connection (218A)
second vibration unit connection (218B)
cells (219)
network (220)
first end (221)
openings (222)
second end (223)
openings (224)
insects (225)
cell network differential pressure sensor (226)
signal (227)
first end impulse line (228)
first air purge flow sensor (229)
first air purge flow regulator (230)
first impulse line gas supply (231)
first end impulse line connection (232)
second end impulse line (233)
second air purge flow sensor (234)
second air purge flow regulator (235)
second impulse line gas supply (236)
second end impulse line connection (237)
cell length (C-L)
cell width (C-W)
network length (N-L)
network width (N-W)
first insect (1$i$)
first insect length (1$i$-L)
first insect width (1$i$-W)
first insect mass (1$i$-WT)
second insect (2$i$)
second insect length (2$i$-L)
second insect width (2$i$-W)
second insect mass (2$i$-WT)
Nth insect (Ni)
average insect length (Ni-L)
average insect width (Ni-W)
average insect mass (Ni-WT)
breeding chamber insect transfer line (238)
hatched insects (239)
hatched insects input (240)
feeding chamber transfer line (241)
egg-laying insects (242)
egg-laying insects input (243)
egg transfer system (244)
conveyor (245)
egg-depleted breeding material (246)
conveyor input (247)
first conveyor input (247A)
second conveyor input (247B)
breeding material (248)
conveyor output (249)
egg-laden breeding material (250)
conveyor motor (251)
controller (252)
signal (253)
first conveyor elevation unit (254)
first support (255)
second conveyor elevation unit (256)
second support (257)
first retracted height (H1)
second elevated height (H2)
screen floor (258)
eggs (259)
air input (260)
air supply entry conduit (261)
air supply (262)
inlet gas distributor (263)
air heater (264)
heat transfer medium input (265)
heat transfer medium output (266)
first humidity sensor (267)
signal (268)
second humidity sensor (269)
signal (270)
air supply fan (271)
air supply fan motor (272)
controller (273)
signal (274)
water (275)
water transfer line (276)
water input valve (278)
water flow sensor (279)
signal (280)
water and gas mixing section (281)
conveyor transfer bin (282A)
egg-laden breeding material conveyor (282B)
air vent (283)
first access door (284)
second access door (285)
low voltage disconnect switch (286)
heat exchanger inlet gas temperature sensor (T1)
signal (XT1)
heat exchanger outlet gas temperature sensor (T2)
signal (XT2)
heat exchanger heat transfer medium inlet temperature (T3)
signal (XT3)
heat exchanger heat transfer medium outlet temperature (T4)
signal (XT4)
first hatched insect input (AFC)
second hatched insect input (BFC)
third hatched insect input (CFC)
insect evacuation module (3000)
separator (300)

first separator (S1)
second separator (S2)
third separator (S3)
interior (301)
feeding chamber exit conduit (302)
first feeding chamber exit conduit (302A)
second feeding chamber exit conduit (302B)
third feeding chamber exit conduit (302C)
insect and gas mixture input (303)
insect and gas mixture (304)
insect portion (304A)
gas portion (304B)
entry section (305)
filter element (306)
exit section (307)
differential pressure sensor (308)
signal (309)
entry section impulse line (310)
exit section impulse line (311)
insect evacuation fan (312)
fan motor (314)
controller (316)
signal (318)
insect-depleted gas (320)
insect-depleted gas output (321)
insect-depleted gas exhaust line (322)
insect-depleted gas recycle line (323)
exhaust gas recycle input (324)
valve (325)
controller (326)
signal (327)
separated insect conveyor (328)
motor (329)
controller (330)
signal (331)
mass sensor (332)
signal (333)
separated insects (334)
egg-depleted breeding material input (335)
egg-depleted breeding material (336)
breeding material conveyor (337)
egg-laden breeding material output (338)
egg-laden breeding material (339)
egg-laden breeding material transfer line (340)
slats (341)
first closed state (341A)
second open state (341B)
upper egg-laying section (342)
lower egg transfer section (343)
slat motor (344)
controller (345)
signal (346)
egg-laden breeding material conveyor (347)
motor (348)
controller (349)
signal (350)
first breeding material mass sensor (351)
signal (352)
second breeding material mass sensor (353)
signal (354)
common entry conduit (CEC)
header vacuum vent valve (VV0)
controller (CV0)
signal (XV0)
common insect evacuation line reducer (VR0)
common insect evacuation vent line (VRL)
common insect evacuation pressure sensor (PT10)
signal (XT10)
chamber 2 to chamber 1 transfer line (TL21)
chamber 3 to chamber 1 transfer line (TL31)
chamber 1 breeding chamber transfer line (TLBC1)
chamber 1 to chamber 2 transfer line (TL12)
chamber 3 to chamber 2 transfer line (TL32)
chamber 2 breeding chamber transfer line (TLBC2)
chamber 1 to chamber 3 transfer line (TL13)
chamber 2 to chamber 3 transfer line (TL23)
chamber 3 breeding chamber transfer line (TLBC3)
feeding chamber 1 insect evacuation port (1FC)
feeding chamber 2 insect evacuation port (2FC)
feeding chamber 3 insect evacuation port (3FC)
feeding chamber 1 evacuation valve (VV1)
controller (CV1)
signal (XV1)
first feeding chamber evacuation line first diameter (D1A)
first feeding chamber evacuation line reducer (VR1)
first feeding chamber evacuation line second diameter (D1B)
feeding chamber 2 evacuation valve (VV2)
controller (CV2)
signal (XV2)
second feeding chamber evacuation line first diameter (D2A)
second feeding chamber evacuation line reducer (VR2)
second feeding chamber evacuation line second diameter (D2B)
feeding chamber 3 evacuation valve (VV3)
controller (CV3)
signal (XV3)
third feeding chamber evacuation line first diameter (D3A)
third feeding chamber evacuation line reducer (VR3)
third feeding chamber evacuation line second diameter (D3B)
first insect coarse separator (S1A)
second insect fine separator (S2A)
particulate separator (S3A)
first insect coarse separator input (S1A1)
second insect fine separator input (S2A1)
particulate separator input (S3A1)
first insect-depleted gas stream (355)
coarse separator gas and insect mixture output (356)
first dipleg (357)
first separator conveyor (358)
motor (358A)
controller (358B)
compression screw (359)
first separated insect stream (360)
first separator valve (361)
second insect-depleted gas stream (362)
fine separator gas and particulate mixture output (363)
second dipleg (364)
second separator conveyor (365)
motor (365A)
controller (365B)
compression screw (366)
second separated insect stream (367)
second separator valve (368)
particulate-depleted gas stream (369)
separated particulate stream (370)
first separated insect stream input (371)
second separated insect stream input (372)
first fine separated insect portion (373)
second fine separated insect portion (374)

breeding chamber fine separated insect portion input (375)
breeding chamber exhaust input (376)
exhaust (377)
differential pressure sensor (DPS)
feeding chamber 1 egg-laden breeding material transfer line (R1)
feeding chamber 2 egg-laden breeding material transfer line (R2)
feeding chamber 3 egg-laden breeding material transfer line (R3)
evacuated separated insect conveyor (378)
motor (378A)
first separator conveyor connection (379)
second separator conveyor connection (380)
combined first and second separator insect stream (381)
particulate separator conveyor (382)
entry section (383)
filter element (384)
exit section (385)
first access door (386)
second access door (387)
low voltage disconnect switch (388)
air vent (389)
air supply (390)
insect breeding module (4000)
first insect breeding module (4000A)
second insect breeding module (4000B)
third insect breeding module (4000C)
breeding chamber (BC)
breeding chamber 1 (BC1)
breeding chamber 2 (BC2)
breeding chamber 3 (BC3)
interior (BCIN)
feeding chamber 1 breeding chamber 1 input (BC1A)
feeding chamber 1 breeding chamber output (BC1B)
first conveyor transfer unit (XY1A)
first hatched insect detection sensor (OS1)
second hatched insect detection sensor (OS2)
third hatched insect detection sensor (OS3)
fourth hatched insect detection sensor (OS4)
fifth hatched insect detection sensor (OS5)
first conveyor (CY1A)
conveyor 1 to conveyor 2 transfer unit (XY2A)
first conveyor height (CH1A)
second conveyor (CY2A)
conveyor 2 to conveyor 3 transfer unit (XY3A)
second conveyor height (CH2A)
third conveyor (CY3A)
conveyor 3 to conveyor 4 transfer unit (XY4A)
third conveyor height (CH3A)
fourth conveyor (CY4A)
conveyor 4 to conveyor 5 transfer unit (XY5A)
fourth conveyor height (CH4A)
fifth conveyor (CY5A)
conveyor 5 to conveyor 6 transfer unit (XY6A)
fifth conveyor height (CH5A)
sixth conveyor (CY6A)
conveyor 6 to conveyor 7 transfer unit (XY7A)
sixth conveyor height (CH6A)
seventh conveyor (CY7A)
seventh conveyor height (CH7A)
breeding chamber 1 hatched egg and breeding material transfer line (U1)
breeding chamber 2 hatched egg and breeding material transfer line (U2)
breeding chamber 3 hatched egg and breeding material transfer line (U3)
fiberglass cable trays (FGT)
high density plastic ties (HDT)
hatched insects (400)
conveyor transfer bin (401)
hatched insect conveyor (402)
side wall (403)
first conveyor first roller (P1)
first conveyor second roller (P2)
second conveyor first roller (P3)
second conveyor second roller (P4)
third conveyor first roller (P5)
third conveyor second roller (P6)
fourth conveyor first roller (P7)
fourth conveyor second roller (P8)
fifth conveyor first roller (P9)
fifth conveyor second roller (P10)
roller chain support roller (P11)
drive unit (404)
motor (405)
sprocket (406)
roller (407)
roller chain (408)
first breeding chamber conveyor train (BCT1)
second breeding chamber conveyor train (BCT2)
third breeding chamber conveyor train (BCT3)
first conveyor first roller (P1B)
first conveyor second roller (P2B)
second conveyor first roller (P3B)
second conveyor second roller (P4B)
third conveyor first roller (P5B)
third conveyor second roller (P6B)
fourth conveyor first roller (P7B)
fourth conveyor second roller (P8B)
fifth conveyor first roller (P9B)
fifth conveyor second roller (P10B)
roller chain support roller (P11B)
drive unit (404B)
motor (405B)
sprocket (406B)
roller (407B)
roller chain (408B)
first conveyor first roller (P1C)
first conveyor second roller (P2C)
second conveyor first roller (P3C)
second conveyor second roller (P4C)
third conveyor first roller (P5C)
third conveyor second roller (P6C)
fourth conveyor first roller (P7C)
fourth conveyor second roller (P8C)
fifth conveyor first roller (P9C)
fifth conveyor second roller (P10C)
roller chain support roller (P11C)
drive unit (404C)
motor (405C)
sprocket (406C)
roller (407C)
roller chain (408C)
conveyor side view (CSV)
vertical lift conveyor (409)
lower conveyor unit (410)
upper conveyor unit (411)
first lower conveyor roller (412)
second lower conveyor roller (413)
third lower conveyor roller (414)
lower conveyor belt (415)

first upper conveyor belt roller (416)
second upper conveyor roller (417)
upper conveyor belt (418)
lift conveyor drive unit (419)
first access door (420)
second access door (421)
low voltage disconnect switch (422)
temperature sensor (423)
signal (424)
humidity sensor (425)
signal (426)
air vent (427)
air supply (428)
temperature control unit (429)
hatched insect separation module (5000)
first hatched insect separation module (5000A)
second hatched insect separation module (5000B)
third hatched insect separation module (5000C)
first hatched insect output (DFC)
second hatched insect output (EFC)
third hatched insect output (FFC)
breeding material and insect separator (SEP1A)
interior (SIN1)
separator input (1SEPA)
separator material output (1SEPB)
separator insect output (1SEPC)
separator hatched insect transfer line (O1)
separator feeding chamber 1 transfer line (O11)
separator feeding chamber 2 transfer line (O12)
separator feeding chamber 3 transfer line (O13)
breeding material tank (500)
interior (501)
breeding material input (502)
breeding material input distributor (502A)
top section (503)
bottom section (506)
side wall (507)
breeding material screw conveyor (508)
breeding material output (510)
breeding material transfer line (511)
breeding material screw conveyor motor (512)
controller (513)
signal (514)
hatched insect and breeding material input (515)
hatched insect output (516)
dipleg (517)
egg-depleted material (518)
egg-depleted material transfer conveyor (519)
motor (520)
controller (521)
material transfer line (522)
breeding material (523)
level sensor (524)
breeding material transfer conveyor (525)
motor (527)
first access door (528)
second access door (529)
low voltage disconnect switch (530)
grinder (1250)
ground separated insects (1500)
lipid extraction unit (1501)
decanter (1502)
weir (1503)
side wall (1504)
interior (1505)
first immiscible liquid (1506)
first density (RHO1)
first molecular weight (MW1)
second immiscible liquid (1507)
second density (RHO2)
second molecular weight (MW2)
separator insect input (1508)
diptube (1509)
first level sensor (1510)
signal (1511)
interface region (1512)
second level sensor (1513)
signal (1514)
first section (1515)
second section (1516)
first immiscible liquid and lipid mixture output (1517)
first immiscible liquid and lipid mixture (1518)
lipid transfer pump (1519)
second immiscible liquid and particulate mixture output (1520)
second immiscible liquid and particulate mixture (1521)
second immiscible liquid recirculation pump (1522)
particulate filter (1523)
second immiscible liquid input (1524)
second immiscible liquid output (1525)
particulate-depleted second immiscible liquid (1526)
particulate-depleted liquid input (1527)
interface layer protein take-off point (1528)
interface layer protein stream (1529)
interface layer protein pump (1530)
filtered protein stream (1531)
filtered protein output (1532)
temperature sensor (1533)
signal (1534)
pathogen removal unit (1550)
pathogen-laden insects (1560)
pathogen-depleted insects (1570)
conveyor (1580)
multifunctional flour mixing module (6000)
insect distribution module (6A)
insects (6A1)
insect tank (6A2)
interior (6A3)
insect input (6A4)
insect conveyor (6A5)
insect conveyor output (6A6)
insect mass sensor (6A7)
signal (6A8)
insect conveyor motor (6A9)
controller (6A10)
signal (6A11)
insect transfer line (6A12)
fiber-starch distribution module (6B)
fiber-starch (6B1)
fiber-starch tank (6B2)
interior (6B3)
fiber-starch input (6B4)
fiber-starch conveyor (6B5)
fiber-starch conveyor output (6B6)
fiber-starch mass sensor (6B7)
signal (6B8)
fiber-starch conveyor motor (6B9)
controller (6B10)
signal (6B11)
fiber-starch transfer line (6B12)
binding agent distribution module (6C)
binding agent (6C1)
binding agent tank (6C2)
interior (6C3)

binding agent input (6C4)
binding agent conveyor (6C5)
binding agent conveyor output (6C6)
binding agent mass sensor (6C7)
signal (6C8)
binding agent conveyor motor (6C9)
controller (6C10)
signal (6C11)
binding agent transfer line (6C12)
density improving textural supplement distribution module (6D)
density improving textural supplement (6D1)
density improving textural supplement tank (6D2)
interior (6D3)
density improving textural supplement input (6D4)
density improving textural supplement conveyor (6D5)
density improving textural supplement conveyor output (6D6)
density improving textural supplement mass sensor (6D7)
signal (6D8)
density improving textural supplement conveyor motor (6D9)
controller (6D10)
signal (6D11)
density improving textural supplement transfer line (6D12)
moisture improving textural supplement distribution module (6E)
moisture improving textural supplement (6E1)
moisture improving textural supplement tank (6E2)
interior (6E3)
moisture improving textural supplement input (6E4)
moisture improving textural supplement conveyor (6E5)
moisture improving textural supplement conveyor output (6E6)
moisture improving textural supplement mass sensor (6E7)
signal (6E8)
moisture improving textural supplement conveyor motor (6E9)
controller (6E10)
signal (6E11)
moisture improving textural supplement transfer line (6E12)
*cannabis* enhancer distribution module (6G)
*cannabis* enhancer (6G1)
*cannabis* enhancer tank (6G2)
interior (6G3)
*cannabis* enhancer input (6G4)
*cannabis* enhancer conveyor (6G5)
*cannabis* enhancer conveyor output (6G6)
*cannabis* enhancer mass sensor (6G7)
signal (6G8)
*cannabis* enhancer conveyor motor (6G9)
controller (6G10)
signal (6G11)
*cannabis* enhancer transfer line (6G12)
multifunctional flour mixing module (6F)
multifunctional flour transfer line (6F0)
multifunctional flour tank (6F1)
interior (6F2)
multifunctional flour tank input (6F3)
top section (6F4)
bottom section (6F5)
side wall (6F6)
level sensor (6F7)
signal (6F8)
screw conveyor (6F9)
multifunctional flour output (6F10)
multifunctional flour conveyor motor (6F11)
controller (6F12)
signal (6F13)
multifunctional flour weigh screw (6F14)
multifunctional flour weigh screw input (6F15)
multifunctional flour weigh screw output (6F16)
mass sensor (6F17)
signal (6F18)
weigh screw motor (6F19)
controller (6F20)
signal (6F21)
weighed multifunctional flour stream (6F22)

The invention claimed is:

1. An alimentary protein powder composition having a fat content having a range from 5 weight percent to 60 weight percent, the composition is comprised of:
   (i) ground insects; and
   (ii) ground *cannabis*.

2. The composition according to claim 1, further comprising caffeine.

3. The composition according to claim 1, wherein the ground *cannabis* includes tetrahydrocannabinol.

4. The composition according to claim 1, wherein the ground *cannabis* includes no tetrahydrocannabinol.

5. The composition according to claim 1, further comprising calcium, vitamin A, and L-phenylalanine.

6. The composition according to claim 1, wherein the ground *cannabis* is decarboxylated and includes tetrahydrocannabinol.

7. The composition according to claim 1, further comprising glucuronic acid.

8. The composition according to claim 1, further comprising fatty acids including one or more selected from the group consisting of palmitoleic acid, linoleic acid, alpha-linoleic acid, oleic acid, gamma-linoleic acid, and stearic acid.

9. The composition according to claim 1, further comprising vitamin B1.

10. The composition according to claim 1, further comprising vitamin B2.

11. The composition according to claim 1, further comprising vitamin E.

12. The composition according to claim 1, further comprising N-acetylglucosamine.

13. The composition according to claim 1, wherein the ground *cannabis* includes dried *cannabis*.

14. The composition according to claim 1, wherein the ground *cannabis* is decarboxylated and includes no tetrahydrocannabinol.

15. The composition according to claim 1, further comprising a moisture improving textural supplement comprised of one or more supplements selected from the group consisting of almonds, brazil nuts, cacao, cashews, chestnuts, coconut, filberts, hazelnuts, Indian nuts, macadamia nuts, nut butter, nut oil, nut powder, peanuts, pecans, pili nuts, pine nuts, pinon nuts, pistachios, soy nuts, sunflower seeds, tiger nuts, and walnuts.

16. The composition according to claim 1, further comprising a density improving textural supplement comprised of one or more supplements selected from the group consisting of extracted arrowroot starch, extracted corn starch, extracted lentil starch, extracted potato starch, and extracted tapioca starch.

17. The composition according to claim 1, further comprising minerals comprised of three or more minerals selected from the group consisting of potassium, chloride, sodium, calcium, phosphorous, magnesium, zinc, iron, manganese, copper, iodine, selenium, and molybdenum.

18. The composition according to claim 1, further comprising niacin.

19. The composition according to claim 1, further comprising N-acetyl L tyrosine.

20. The composition according to claim 1, further comprising vitamin B1, vitamin B2, vitamin E, and vitamin A.

21. The composition according to claim 1, further comprising a fiber-starch material comprised of one or more materials selected from the group consisting of a cereal-grain-based material, a grass-based material, a nut-based material, a powdered fruit material, a root-based material, a tuber-based material, and a vegetable-based material.

22. The composition according to claim 1, further comprising a binding agent comprised of one or more selected from the group consisting of agar, agave, alginin, arrowroot, carrageenan, collagen, cornstarch, egg whites, finely ground seeds, furcellaran, gelatin, guar gum, honey, katakuri starch, locust bean gum, pectin, potato starch, proteins, *psyllium* husks, sago, sugar, syrup, tapioca, vegetable gum, and xanthan gum.

23. The composition according to claim 1, further comprising water;
wherein:
the composition is included in a foodstuff;
wherein the foodstuff includes one or more selected from the group consisting of ada, bagels, baked goods, biscuits, bitterballen, bonda, breads, cakes, candies, cereals, chips, chocolate bars, chocolate, coffee, cokodok, confectionery, cookies, cooking batter, corn starch mixtures, crackers, crêpes, croissants, croquettes, croutons, dolma, dough, doughnuts, energy bars, flapjacks, french fries, frozen custard, frozen desserts, frying cakes, fudge, gelatin mixes, granola bars, gulha, hardtack, ice cream, khandvi, khanom buang, krumpets, meze, mixed flours, muffins, multigrain snacks, nachos, nian gao, noodles, nougat, onion rings, pakora, pancakes, panforte, pastas, pastries, pie crust, pita chips, pizza, poffertjes, pretzels, protein powders, pudding, rice krispie treats, sesame sticks, smoothies, snacks, specialty milk, tele-bhaja, tempura, toffee, tortillas, totopo, turkish delights, and waffles.

24. The composition according to claim 1, wherein the ground insects are selected from the group consisting of grasshoppers, crickets, cave crickets, Jerusalem crickets, katydids, weta, lubber, acrida, and locusts.

25. An alimentary protein powder composition having a fat content that ranges from between 5 weight percent to 60 weight percent, the composition is comprised of:
(i) ground insects;
(ii) ground *cannabis;*
(iii) fat;
(iv) L-phenylalanine; and
(v) cacao.

26. An alimentary protein powder composition having a fat content that ranges from between 5 weight percent to 60 weight percent, the composition is comprised of:
(i) ground crickets;
(ii) ground *cannabis;*
(iii) fat;
(iv) L-phenylalanine;
(v) powdered fruit;
(vi) xanthan gum;
(vii) sodium;
(viii) potassium;
(ix) calcium;
(x) iron; and
(xi) vitamin A.

* * * * *